US010973668B2

(12) United States Patent
Behan

(10) Patent No.: US 10,973,668 B2
(45) Date of Patent: Apr. 13, 2021

(54) VALVE DEVICE

(71) Applicant: Coloplast A/S, Humlebaek (DK)

(72) Inventor: Niall Behan, Kilcolgan (IE)

(73) Assignee: Coloplast A/S, Humlebaek (DK)

( * ) Notice: Subject to any disclaimer, the term of this patent is extended or adjusted under 35 U.S.C. 154(b) by 2 days.

(21) Appl. No.: 16/052,614

(22) Filed: Aug. 2, 2018

(65) Prior Publication Data

US 2018/0338849 A1     Nov. 29, 2018

Related U.S. Application Data

(63) Continuation of application No. 14/366,578, filed as application No. PCT/EP2012/076153 on Dec. 19, 2012, now Pat. No. 10,195,066.

(60) Provisional application No. 61/577,302, filed on Dec. 19, 2011, provisional application No. 61/577,308, filed on Dec. 19, 2011, provisional application No. 61/641,804, filed on May 2, 2012.

(30) Foreign Application Priority Data

Nov. 26, 2012   (IE) ..................................... 2012/0508

(51) Int. Cl.
| | |
|---|---|
| *A61F 5/00* | (2006.01) |
| *A61F 2/04* | (2013.01) |
| *A61F 2/966* | (2013.01) |
| *A61F 2/95* | (2013.01) |

(52) U.S. Cl.
CPC .............. *A61F 5/0079* (2013.01); *A61F 2/04* (2013.01); *A61F 2/966* (2013.01); *A61F 2002/044* (2013.01); *A61F 2002/045* (2013.01); *A61F 2002/9511* (2013.01); *A61F 2002/9528* (2013.01); *A61F 2220/0033* (2013.01); *A61F 2220/0075* (2013.01); *A61F 2230/001* (2013.01)

(58) Field of Classification Search
CPC ... A61M 39/22; A61F 2230/0091; A61F 2/07; A61F 2/90; A61F 2/95; A61F 2/2418; A61F 2/01; A61F 2/06; A61F 2/82; A61F 2210/0014; A61F 5/0079; A61F 5/0083; A61F 15/003; A61F 2250/0039; A61B 5/42; A61B 5/204
See application file for complete search history.

(56) References Cited

U.S. PATENT DOCUMENTS

| | | | | |
|---|---|---|---|---|
| 7,547,321 | B2 * | 6/2009 | Silvestri | .................. A61P 35/00 623/1.15 |
| 8,454,686 | B2 * | 6/2013 | Alkhatib | ............... A61F 2/2403 623/2.18 |
| 9,039,724 | B2 * | 5/2015 | Amplatz | .......... A61B 17/12172 606/191 |
| 9,375,338 | B2 * | 6/2016 | Baker | ....................... A61F 2/04 |

(Continued)

FOREIGN PATENT DOCUMENTS

| | | | | |
|---|---|---|---|---|
| WO | WO-2009153770 | A1 * | 12/2009 | ............... A61F 2/04 |
| WO | WO11132634 | A1 | 10/2011 | |

*Primary Examiner* — Seema Mathew
(74) *Attorney, Agent, or Firm* — Coloplast Corp., Coloplast A/S; Nick Baumann

(57) ABSTRACT

A valve device includes a valve, a scaffold connected coaxially to an external surface of the valve, a luminal prosthesis that is adapted to be implanted into a lumen of a patient, with the scaffold and the valve removably attachable inside of the luminal prosthesis.

10 Claims, 70 Drawing Sheets

(56) References Cited

U.S. PATENT DOCUMENTS

| | | | | |
|---|---|---|---|---|
| 2003/0040804 A1* | 2/2003 | Stack | A61F 2/04 | 623/23.7 |
| 2004/0093065 A1* | 5/2004 | Yachia | A61F 2/82 | 623/1.13 |
| 2004/0167605 A1* | 8/2004 | Elliott | A61F 2/90 | 623/1.13 |
| 2005/0049675 A1* | 3/2005 | Wallace | A61B 17/11 | 623/1.13 |
| 2005/0102018 A1* | 5/2005 | Carpenter | A61F 2/07 | 623/1.11 |
| 2007/0142906 A1* | 6/2007 | Figulla | A61F 2/2418 | 623/2.11 |
| 2007/0179590 A1* | 8/2007 | Lu | A61F 2/91 | 623/1.16 |
| 2008/0065136 A1* | 3/2008 | Young | A61F 5/0076 | 606/191 |
| 2008/0082165 A1* | 4/2008 | Wilson | A61F 2/2436 | 623/2.11 |
| 2008/0109087 A1* | 5/2008 | Durgin | A61F 5/0079 | 623/23.65 |
| 2008/0255678 A1* | 10/2008 | Cully | A61F 5/0076 | 623/23.65 |
| 2008/0275540 A1* | 11/2008 | Wen | A61F 2/2418 | 623/1.26 |
| 2009/0138071 A1* | 5/2009 | Cheng | A61F 2/90 | 623/1.15 |
| 2011/0040232 A1* | 2/2011 | Magal | A61F 5/0079 | 604/8 |
| 2011/0152998 A1* | 6/2011 | Berez | A61F 2/82 | 623/1.15 |
| 2011/0319980 A1* | 12/2011 | Ryan | A61F 2/07 | 623/1.16 |
| 2012/0010697 A1* | 1/2012 | Shin | A61F 2/2415 | 623/1.26 |
| 2012/0095384 A1* | 4/2012 | Babkes | A61F 5/0079 | 604/9 |
| 2012/0253260 A1* | 10/2012 | Belhe | A61F 5/0076 | 604/9 |
| 2012/0271337 A1* | 10/2012 | Figulla | A61B 17/12022 | 606/191 |
| 2012/0271403 A1* | 10/2012 | Gries | A61F 2/90 | 623/1.15 |
| 2012/0310138 A1* | 12/2012 | Behan | A61F 5/0079 | 604/9 |
| 2014/0243950 A1* | 8/2014 | Weiner | A61F 2/958 | 623/1.12 |
| 2014/0277573 A1* | 9/2014 | Gill | A61F 2/90 | 623/23.68 |
| 2015/0282922 A1* | 10/2015 | Hingston | A61L 31/048 | 623/23.7 |
| 2016/0081832 A1* | 3/2016 | Hingston | A61F 5/0083 | 623/23.65 |
| 2016/0331529 A1* | 11/2016 | Marchand | A61F 2/2436 | |

\* cited by examiner

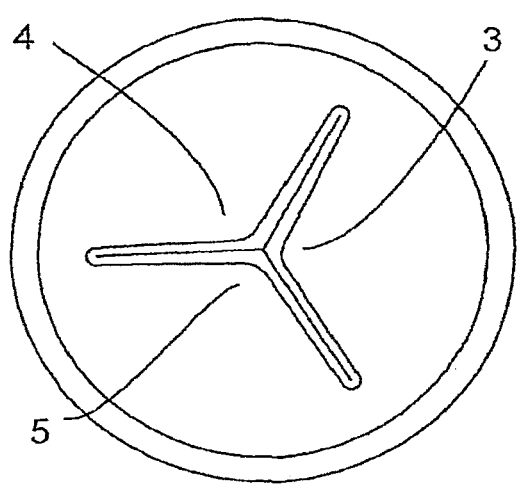
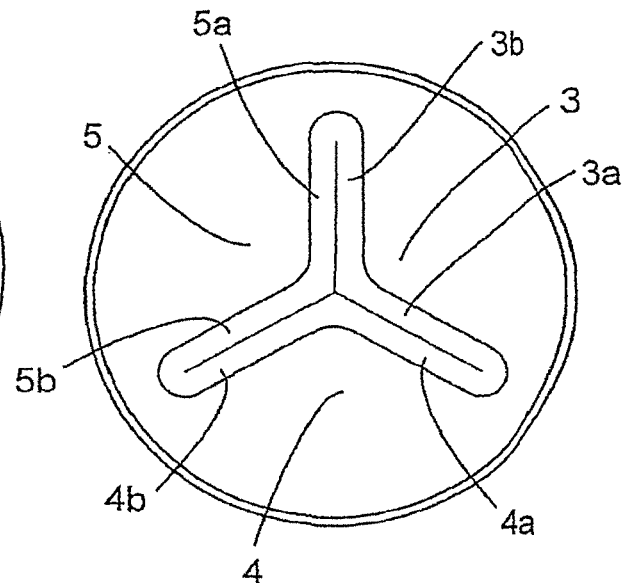
Fig. 3    Fig. 4
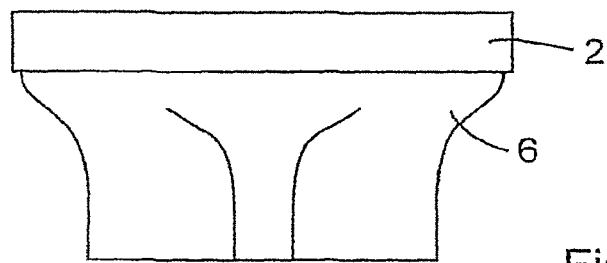
Fig. 5
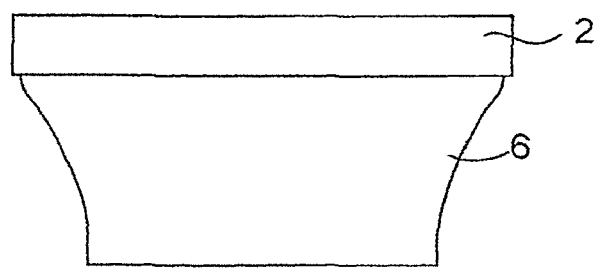
Fig. 6

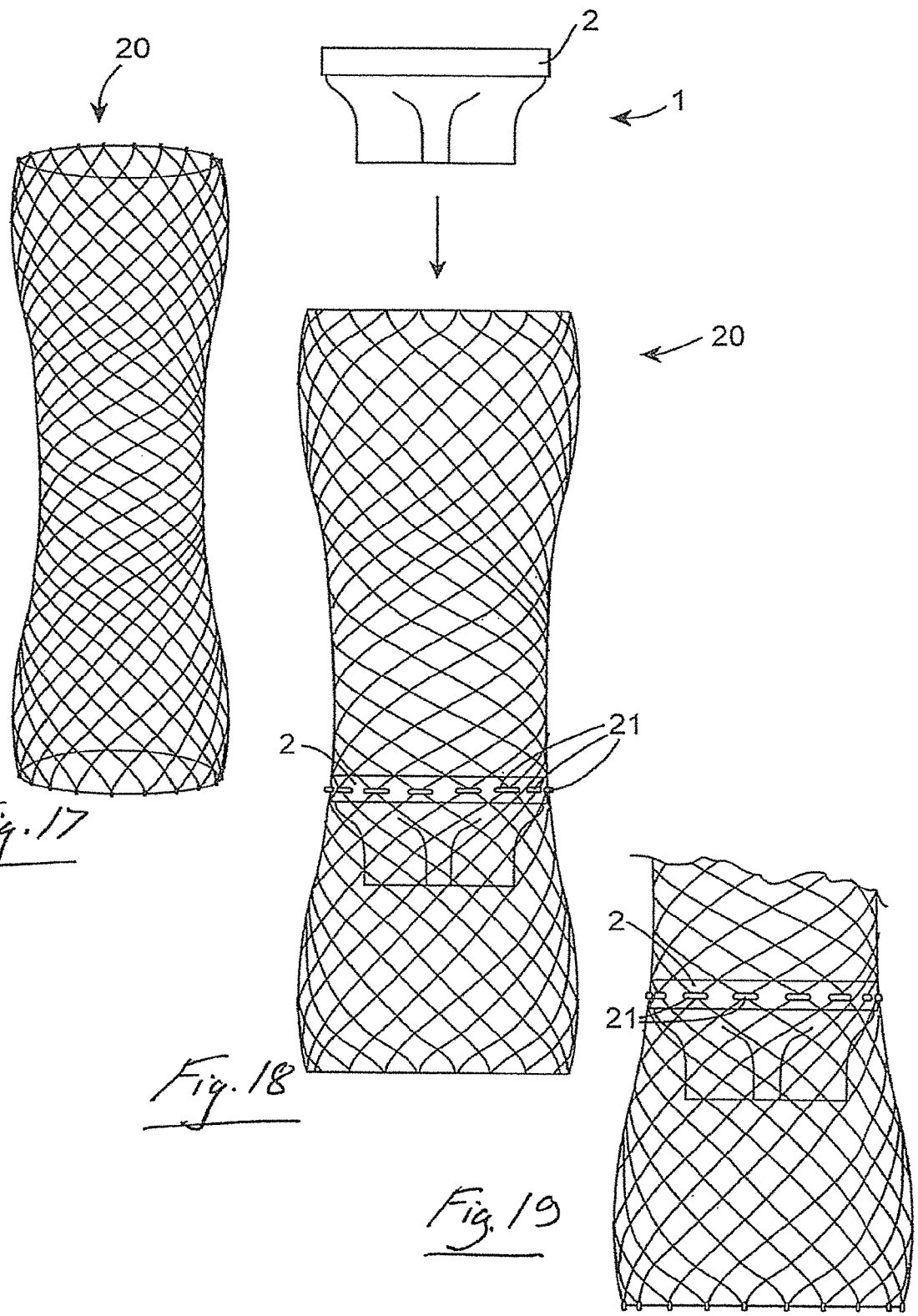

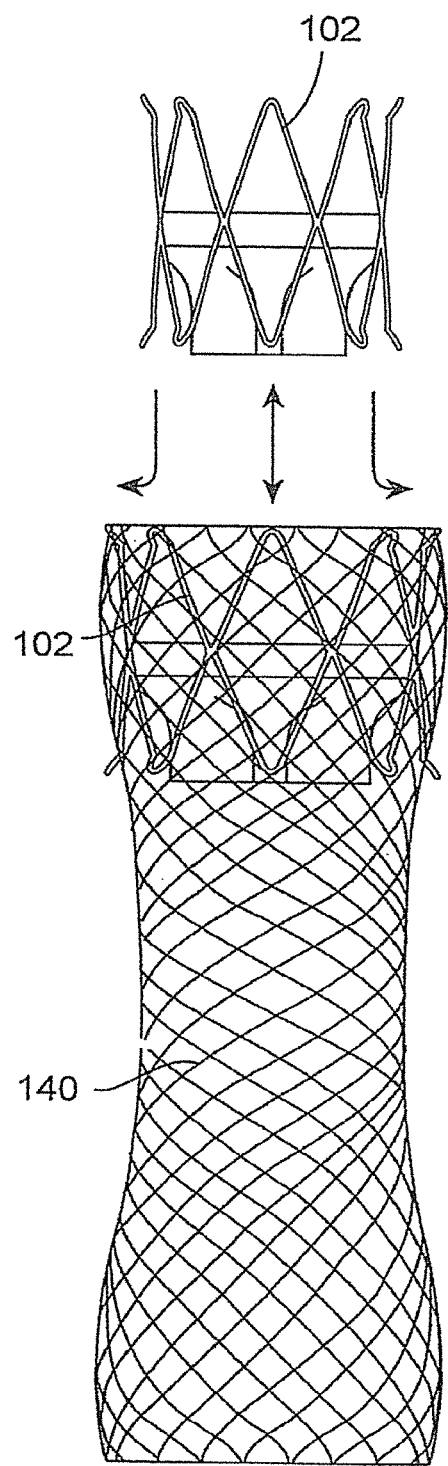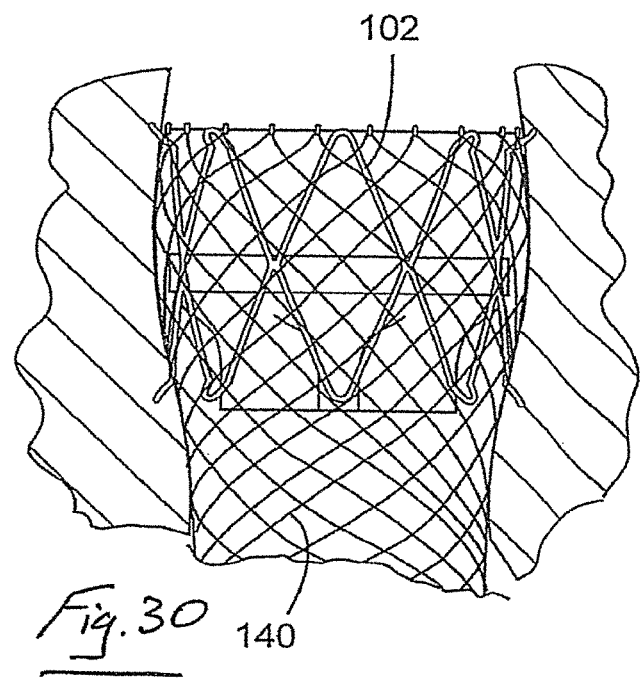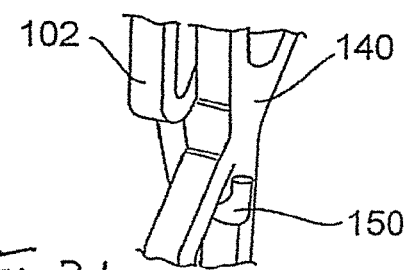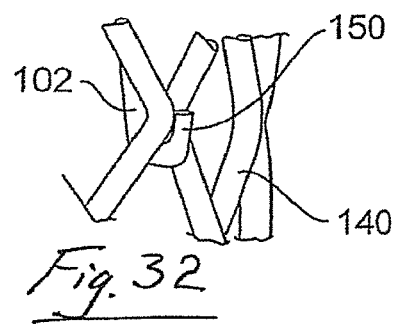
Fig. 29
Fig. 30
Fig. 31
Fig. 32

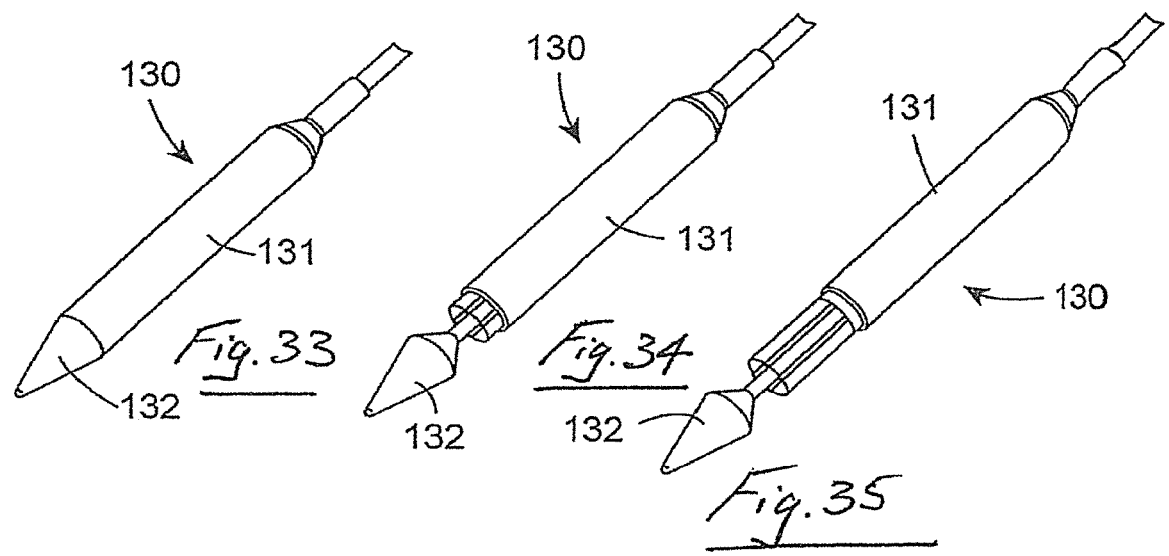
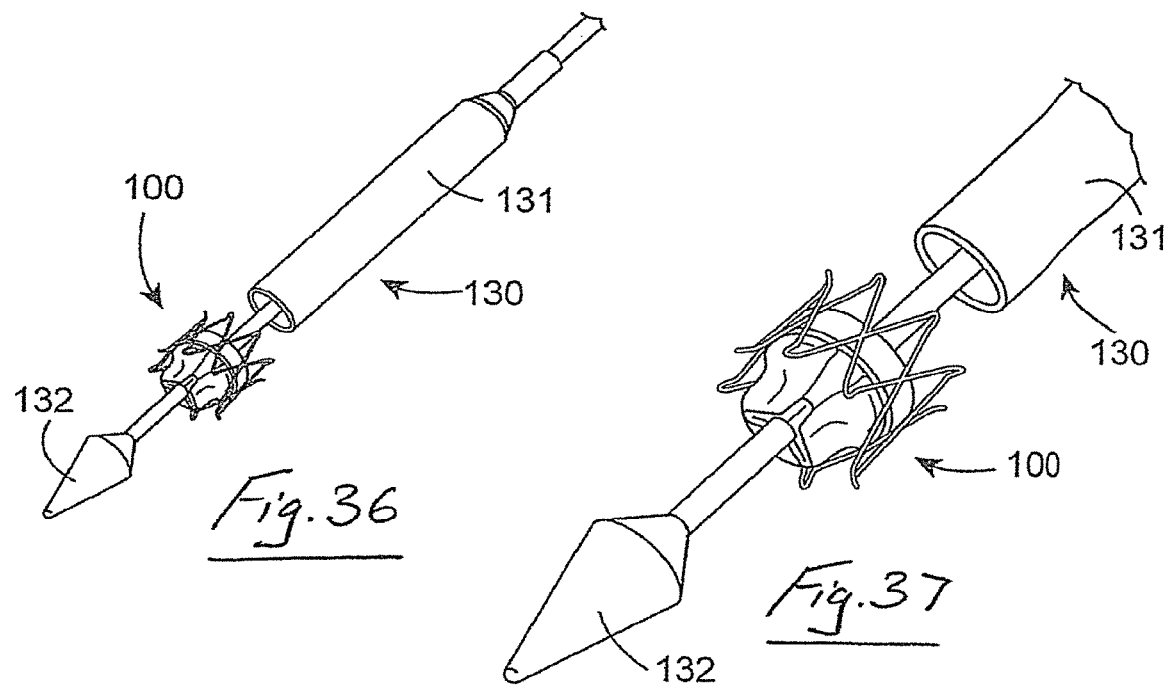

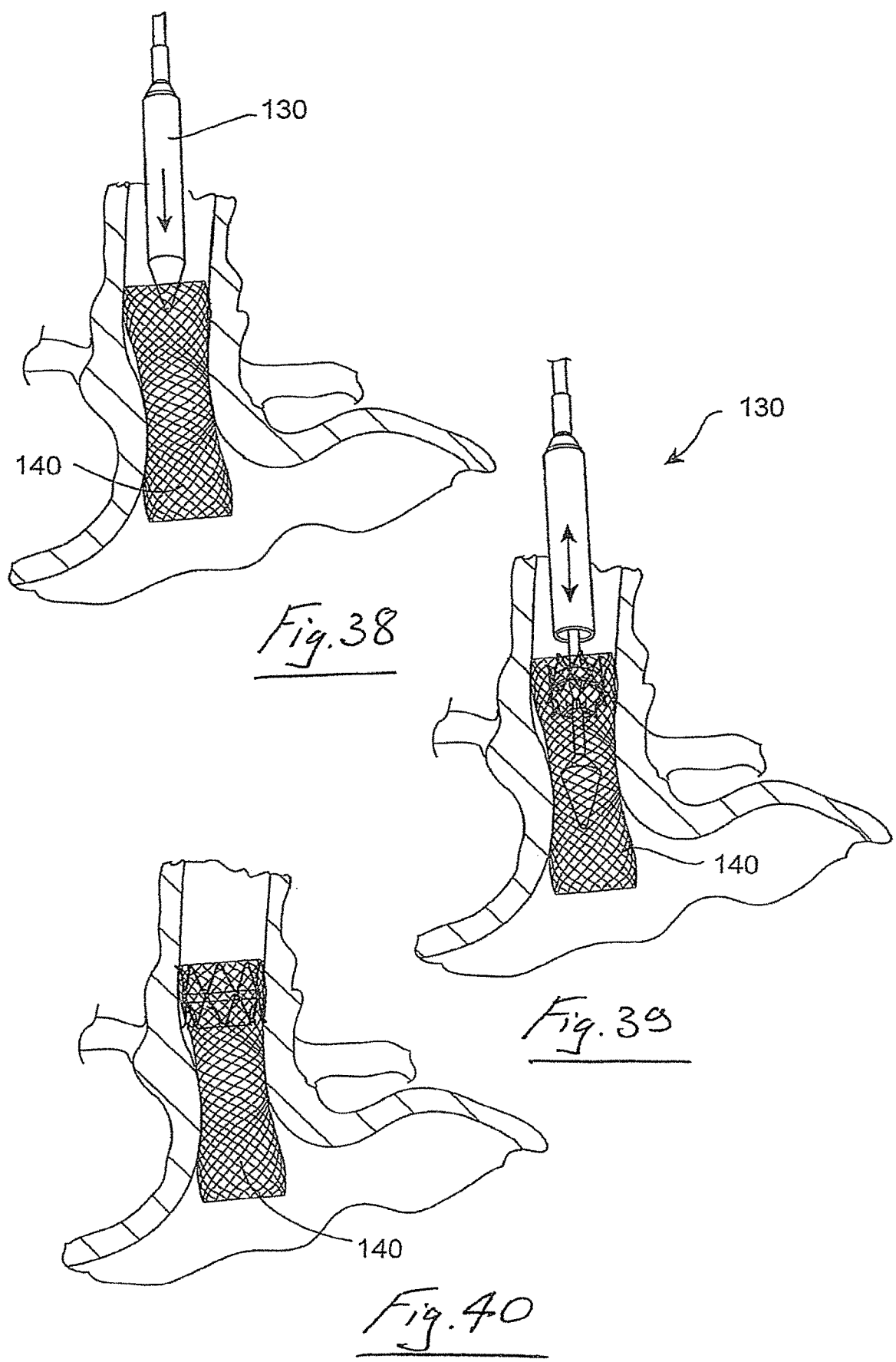

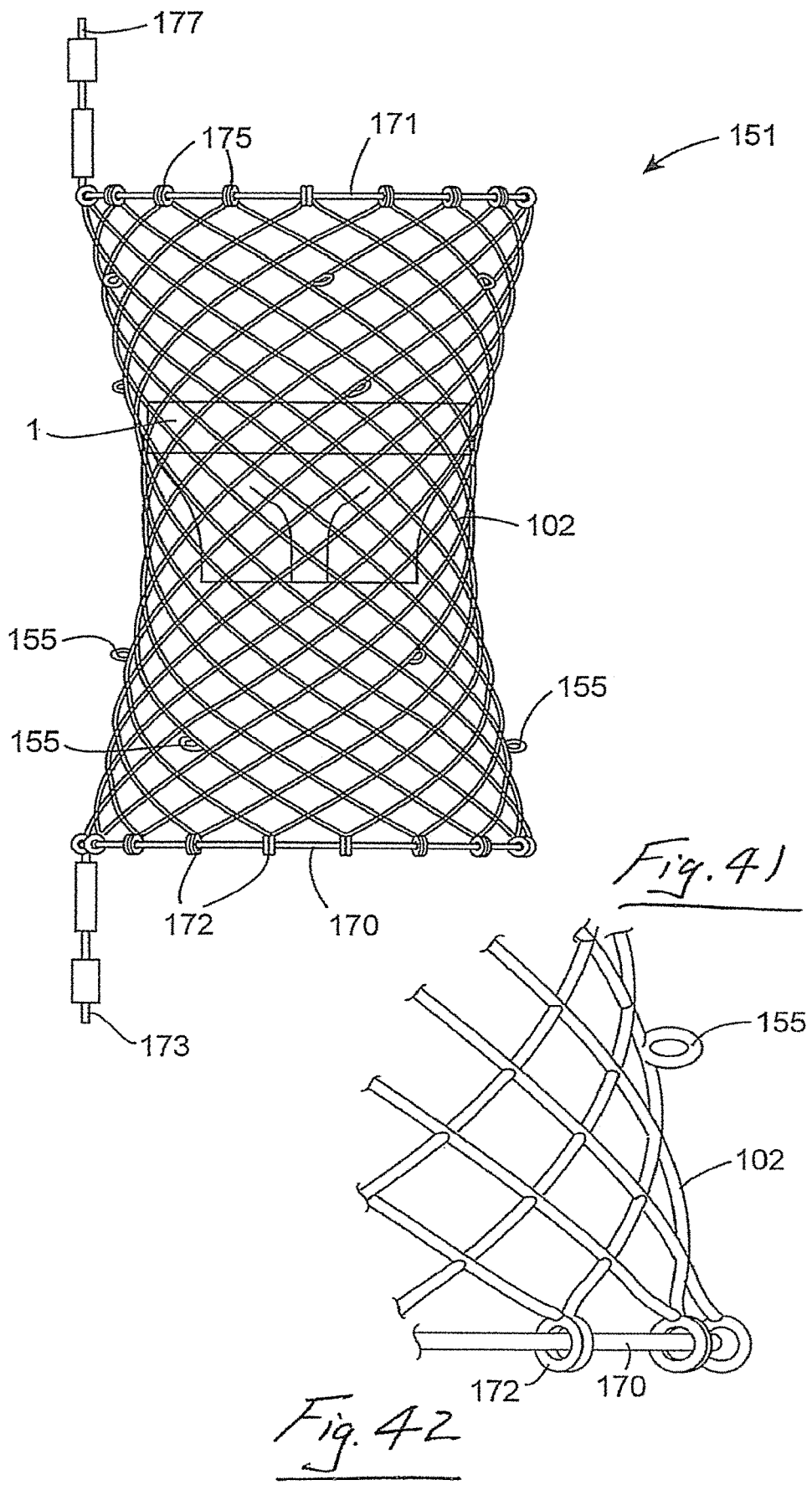

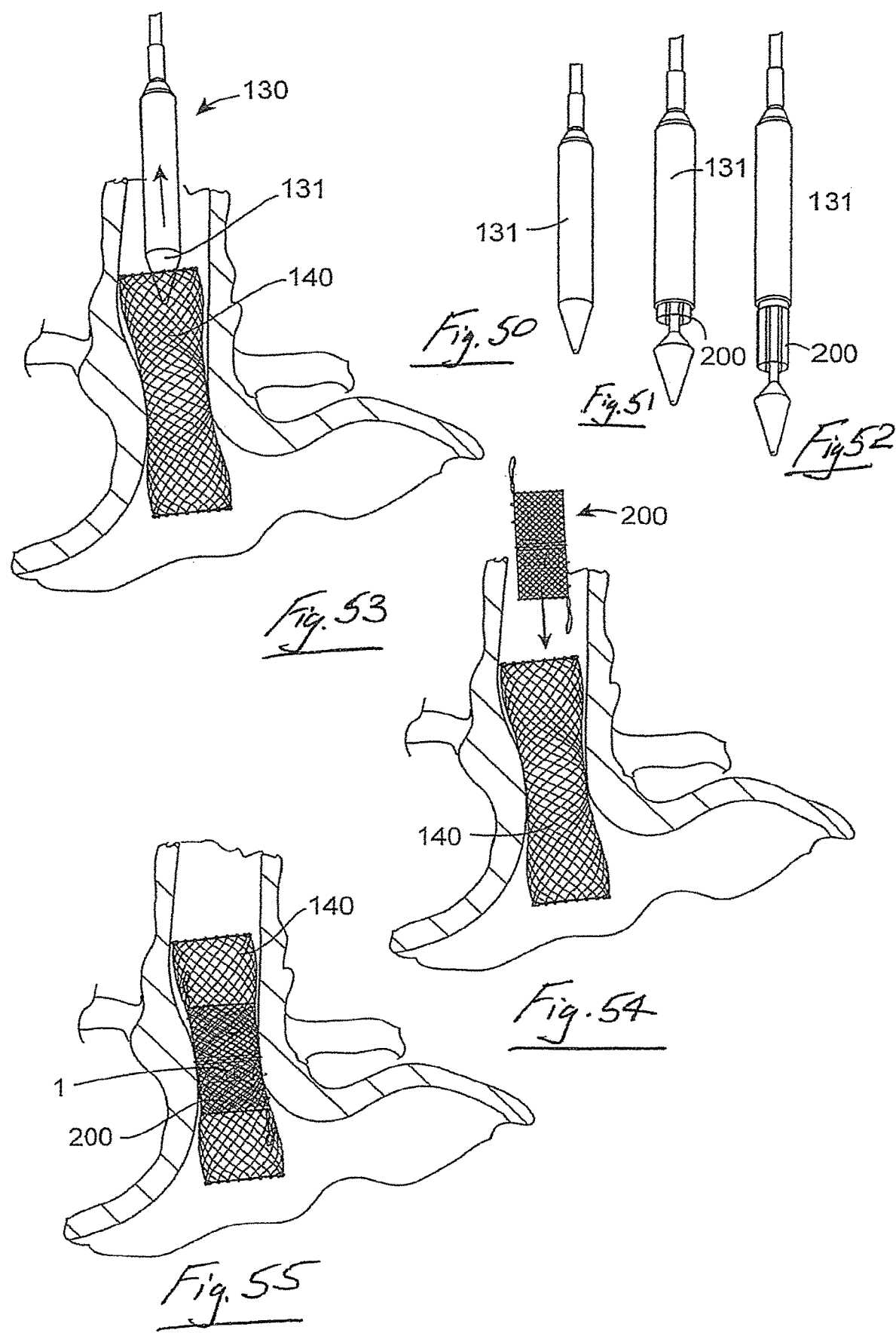

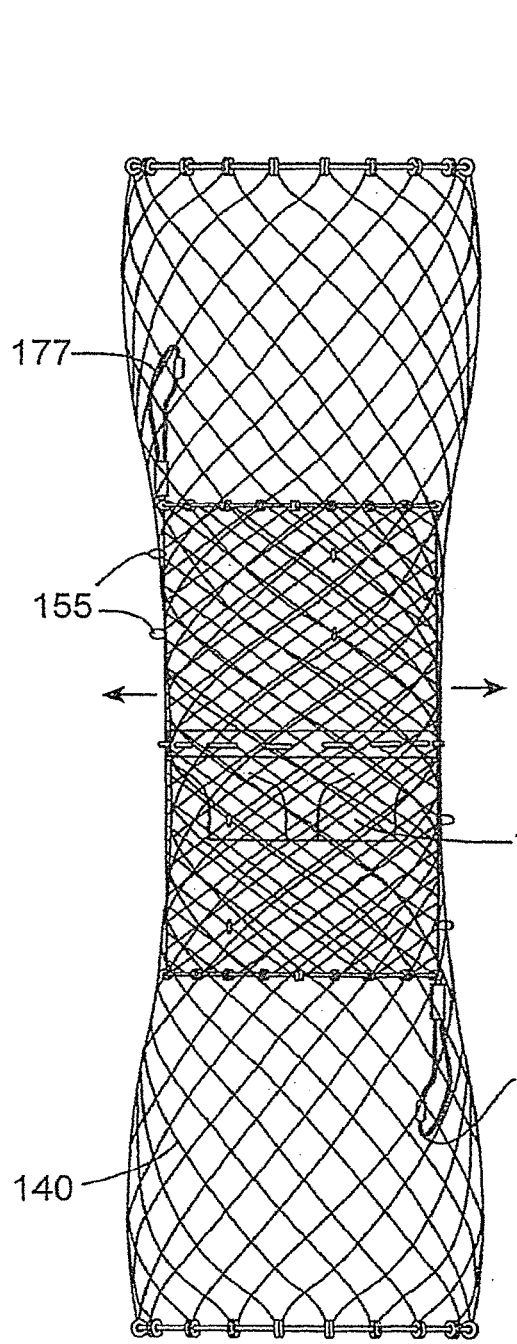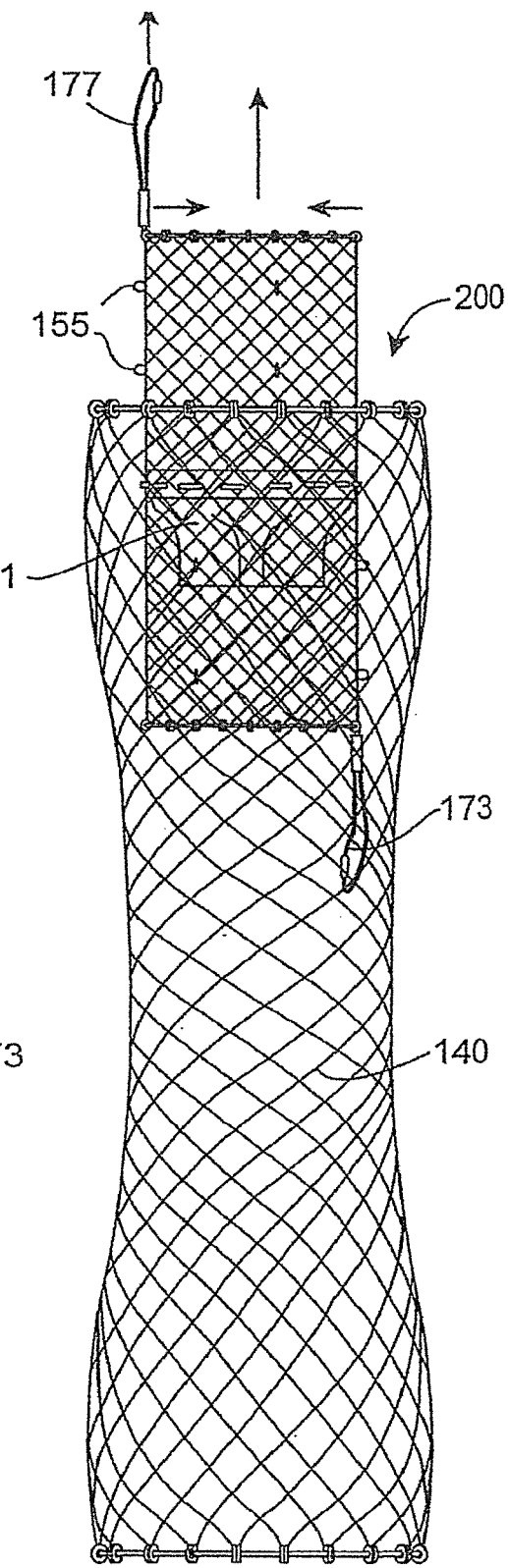

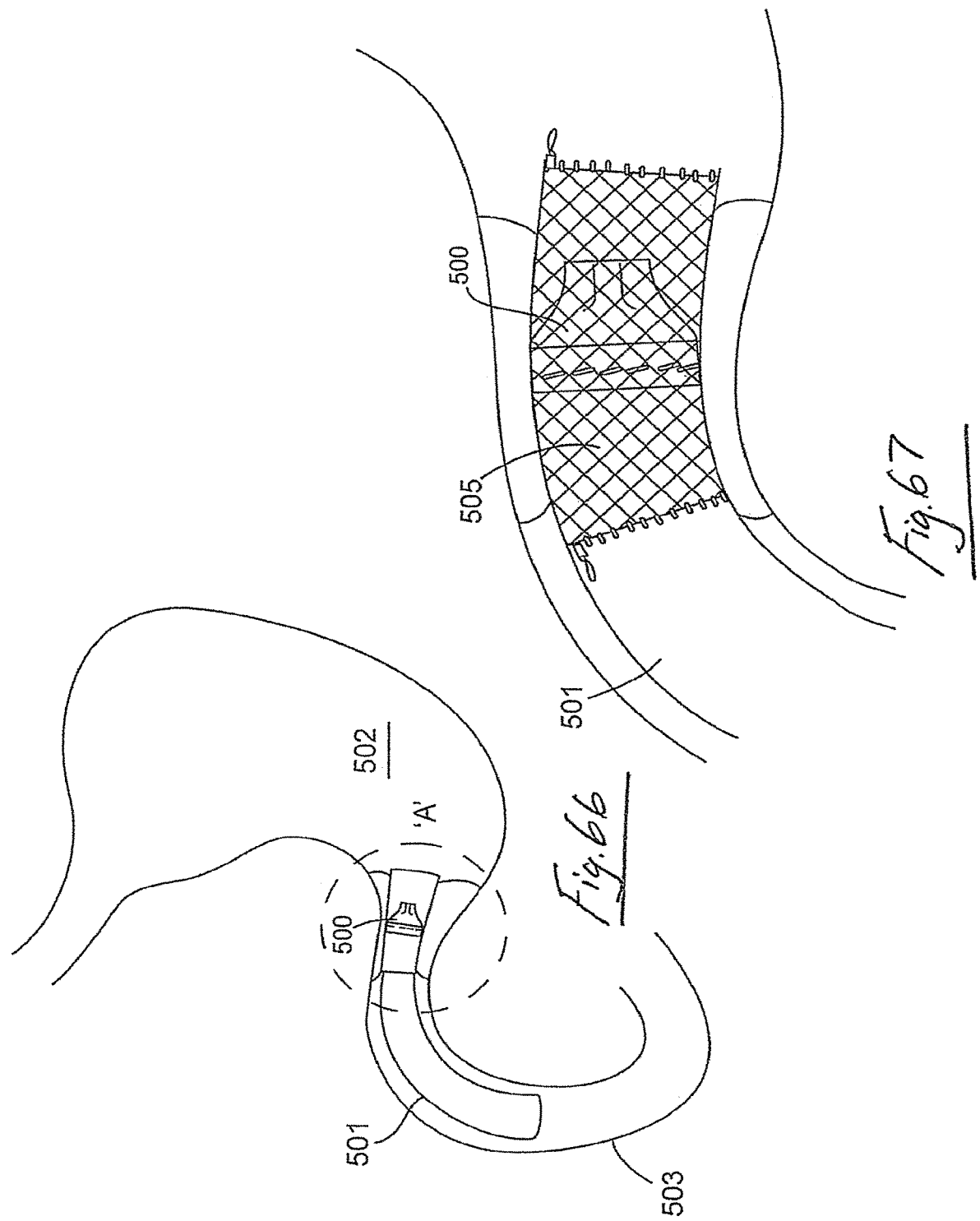

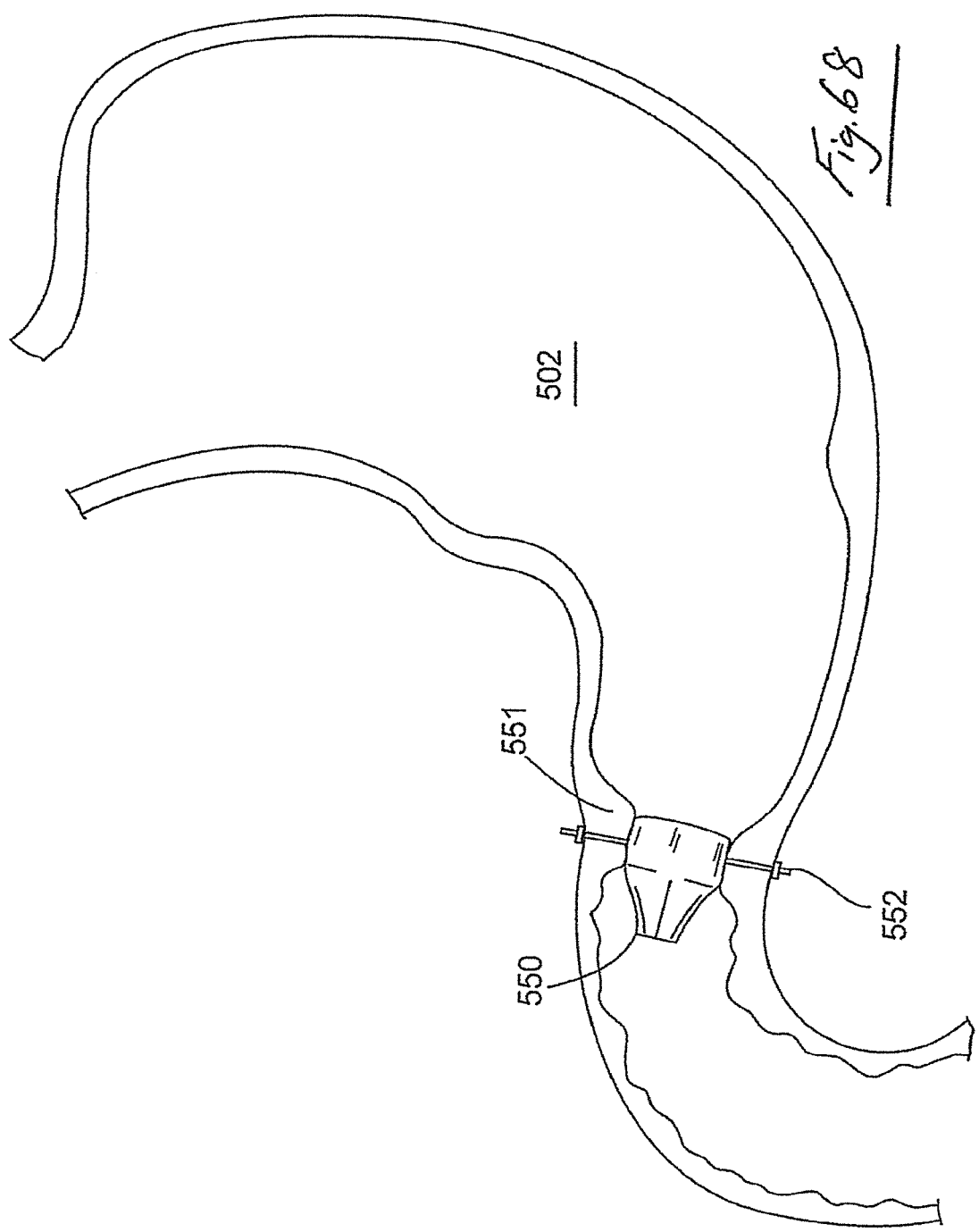

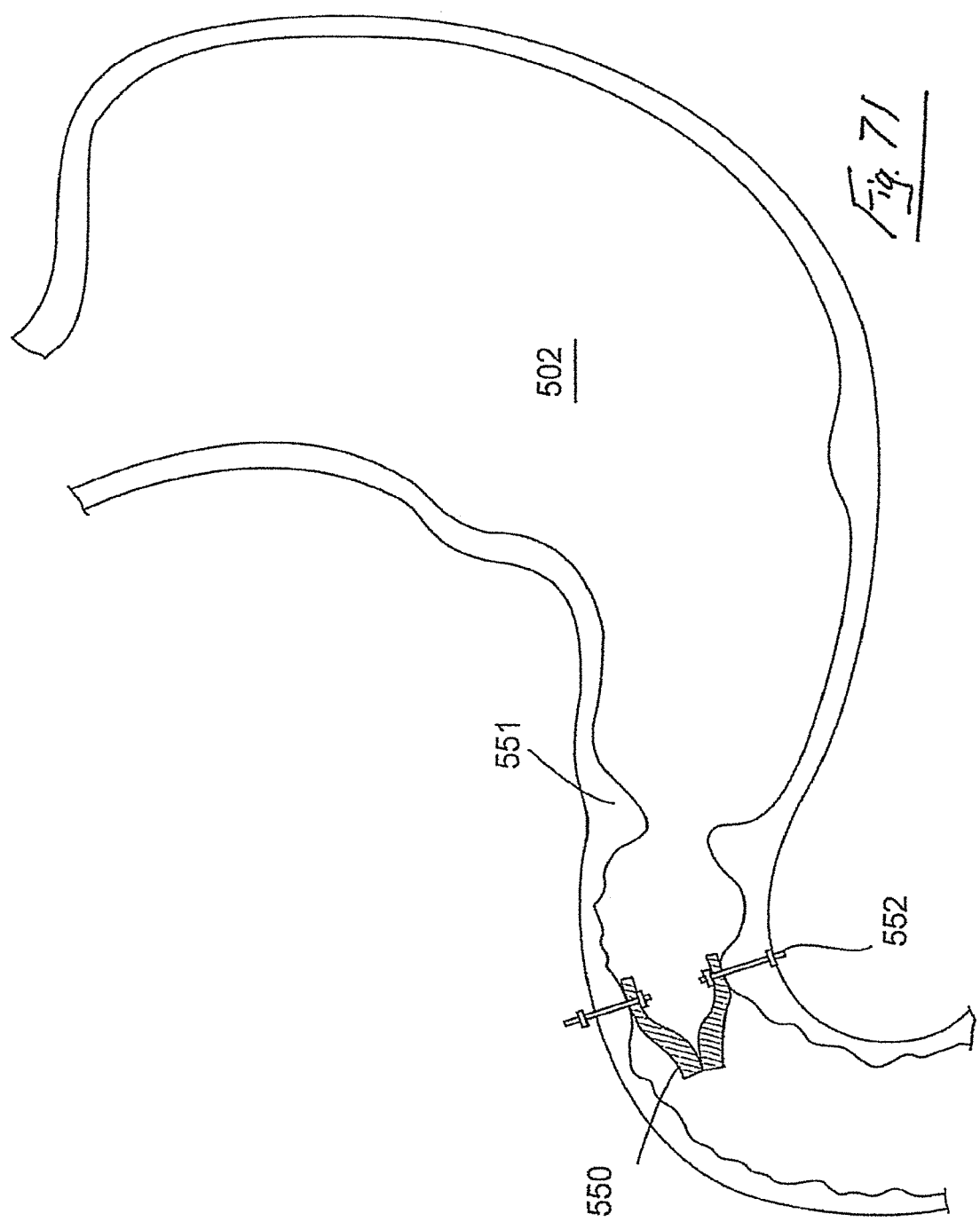

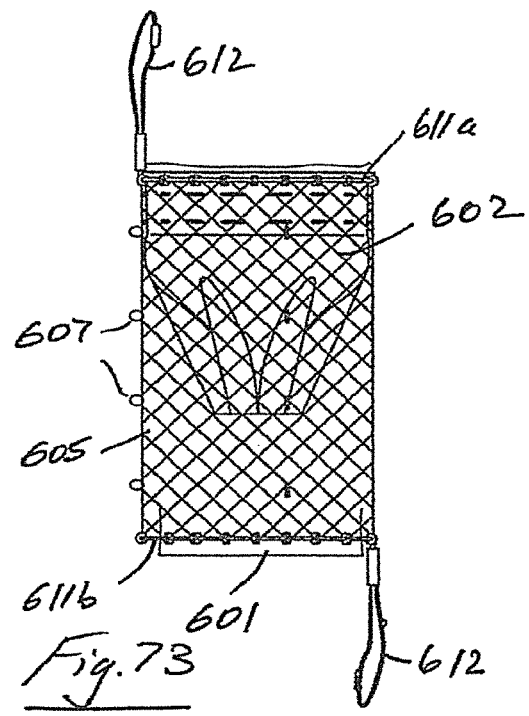
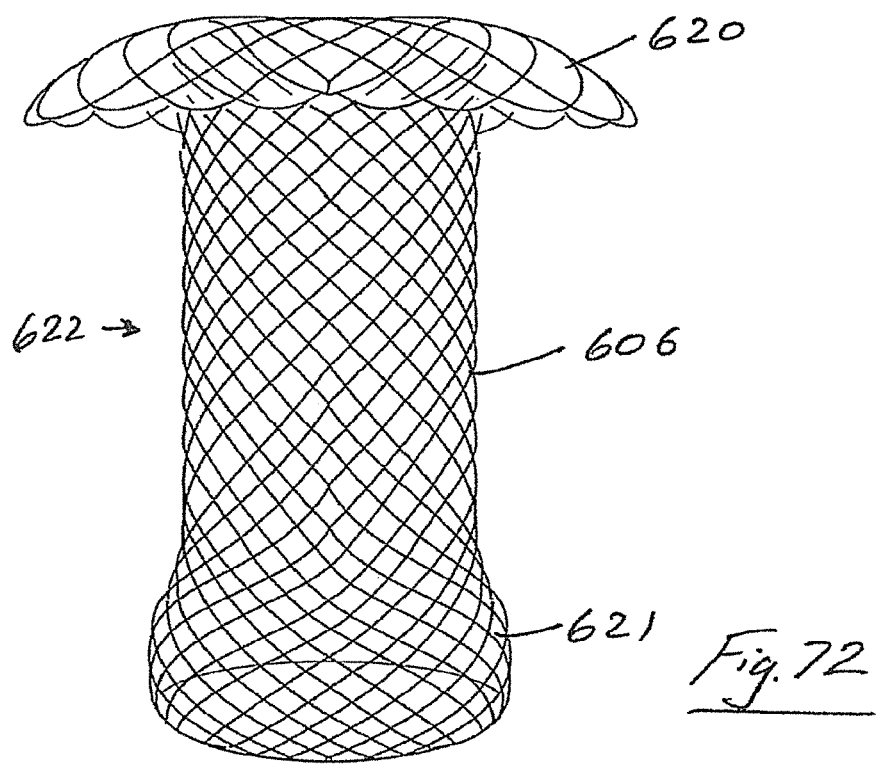

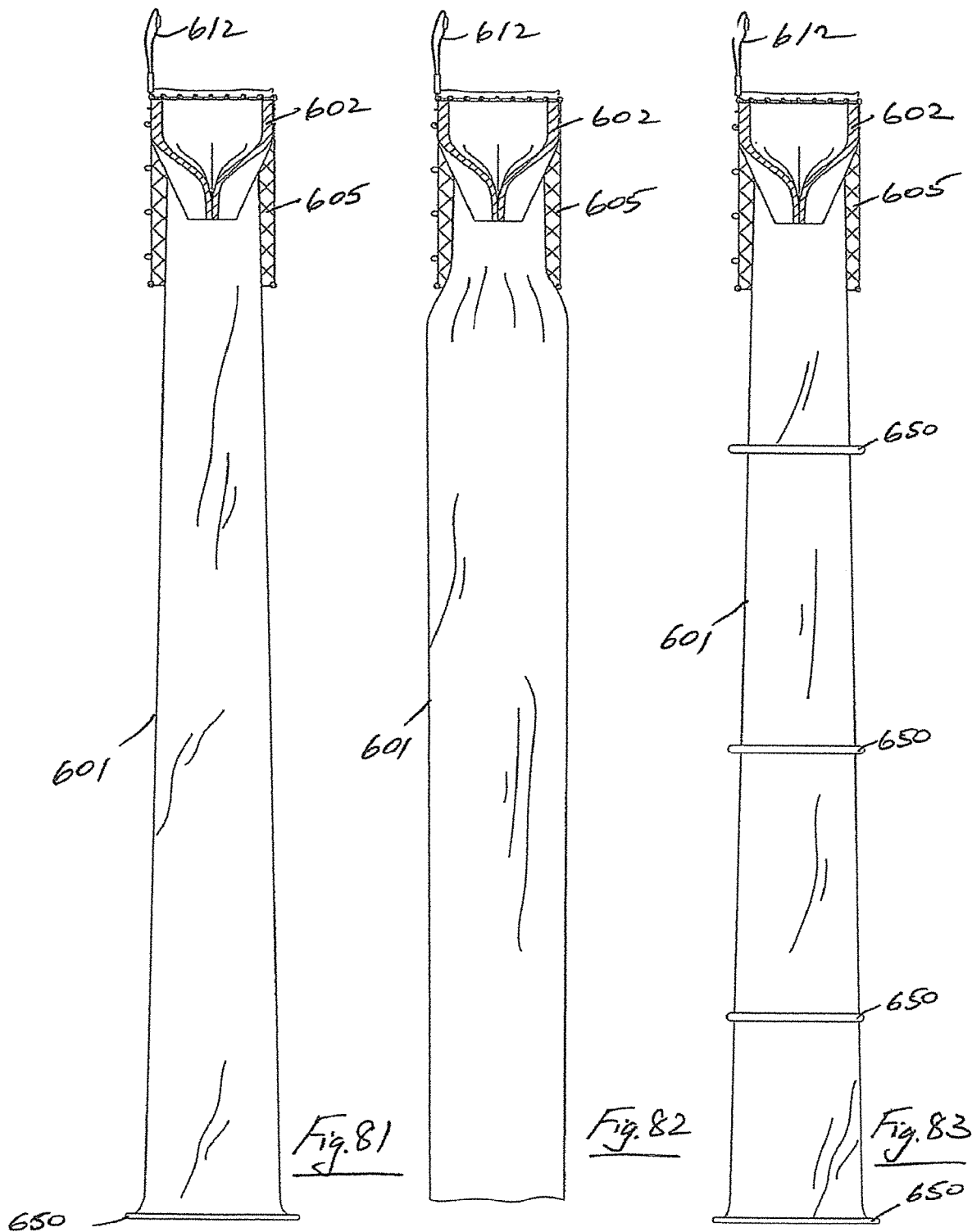

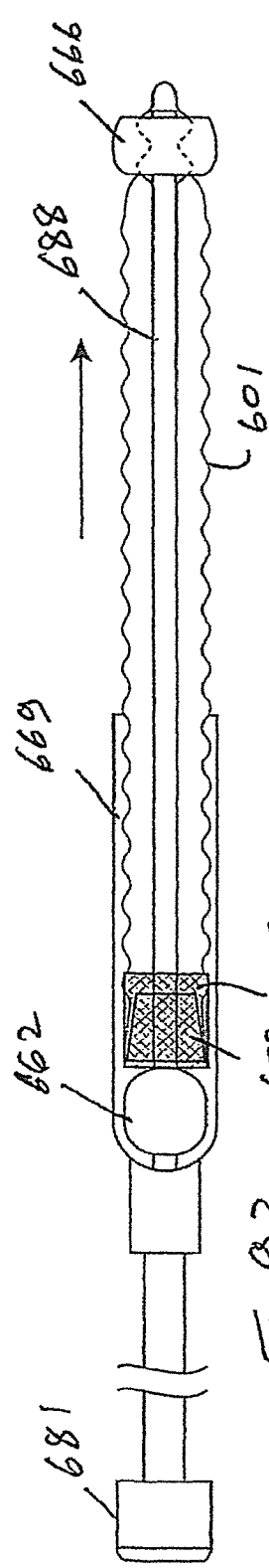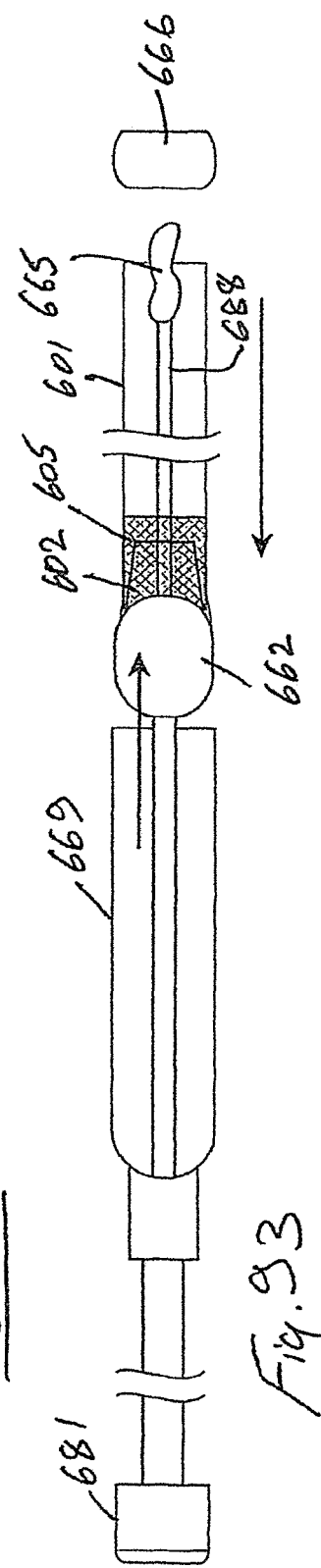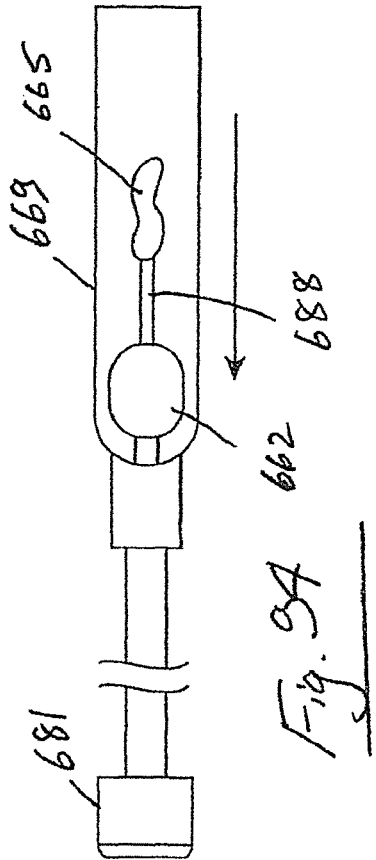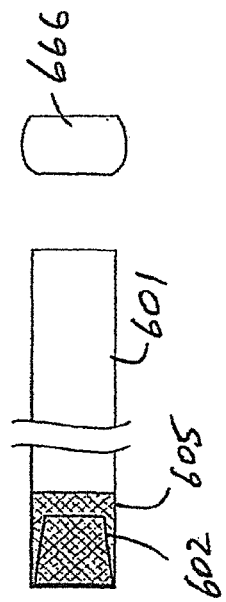
Fig. 92  Fig. 93  Fig. 94

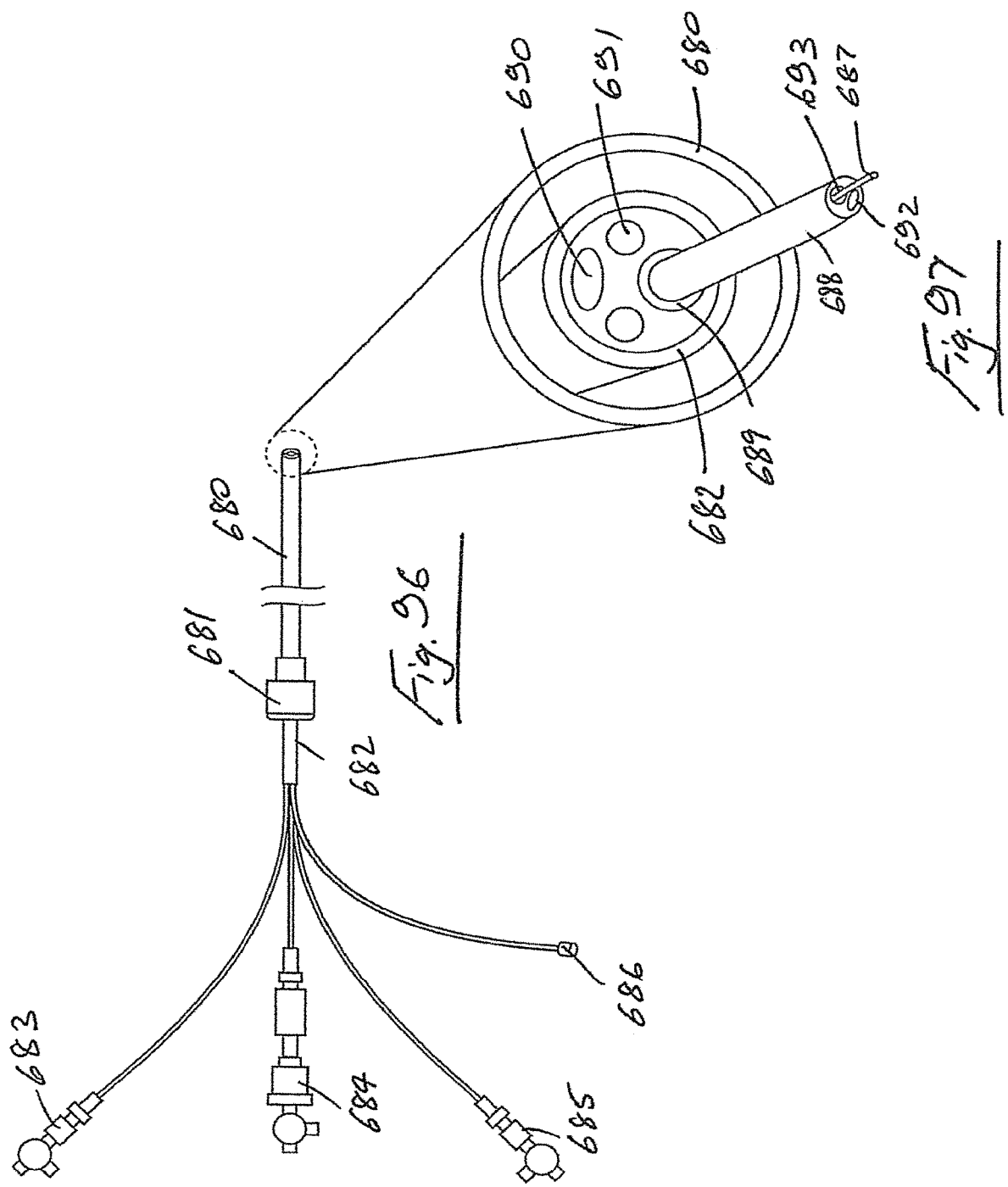

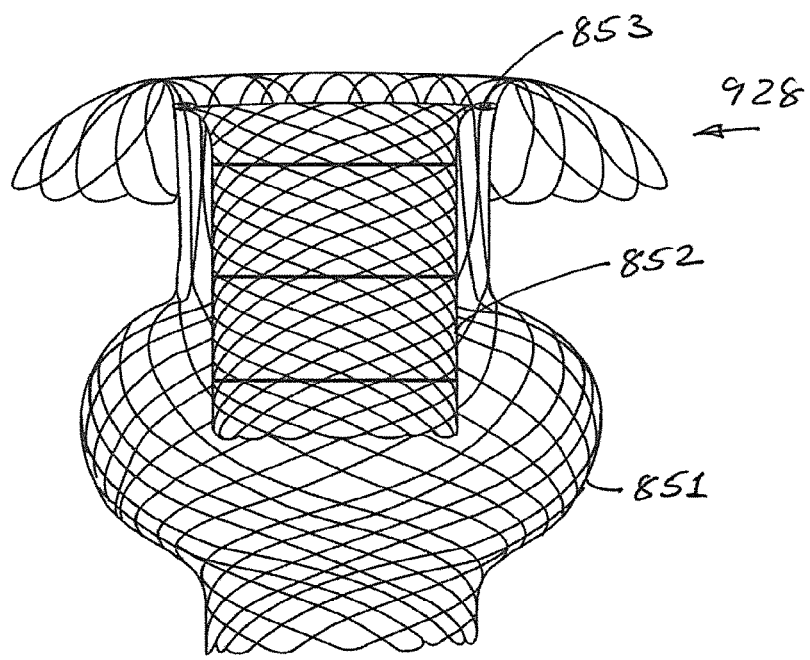
Fig. 123
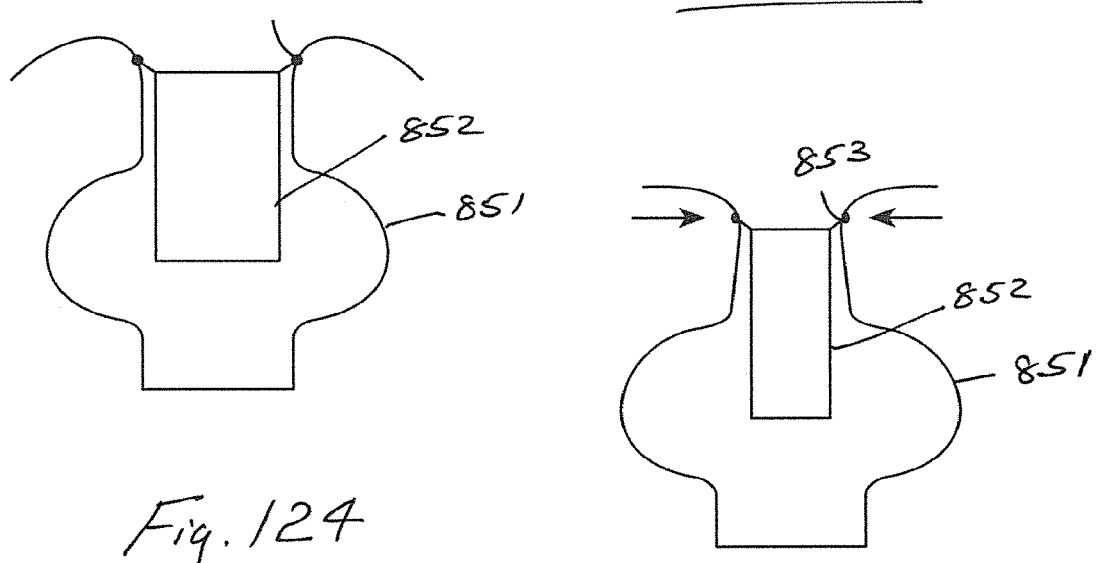
Fig. 124
Fig. 125

VALVE DEVICE

The invention relates to a device. In one aspect the invention relates to a gastrointestinal implant device.

There are several procedures and devices for treatment of obesity. Whilst many of these devices are successful in the short term various problems can arise because the patient does not achieve a feeling of satiety (fullness) after eating.

STATEMENTS OF INVENTION

According to the invention there is provided a luminal prosthesis comprising:
  a first part which is adapted to be retained in a lumen; and
  a second part which is connected to the first part such that a force applied to the second part is at least partially isolated from the first part.

The second part may be adapted for mounting of a device such as a valve.

The prosthesis may comprise a connector between the first part and the second part. The connector may comprise at least one tether. The connector may comprise at least one strut. The connector may comprise at least one wire.

In one case the first part and the second part are formed trout a single precursor.

The precursor may comprise one continuous stent which is folded to form the first part and the second part.

In one case the second part is radially inward of the first part.

The first part may comprise a bulbous region.

The second part may comprise a scaffold-receiving region.

The prosthesis may comprise a proximal flare. There may be a transition region between the bulbous region and the proximal flare.

In one case the prosthesis comprises a bulbous region, a proximal flare and a scaffold receiving region.

The proximal flare may be of open mesh construction. The proximal flare may be adapted to resist axial movement of the prosthesis. The proximal flare may be at least partially coated. In one case the proximal flare has a peripheral region which is coated.

In one embodiment the bulbous region is partially coated.

In one case the scaffold receiving region is stiff relative to the bulbous region.

The prosthesis may comprise a transition region between the proximal flare and the bulbous region. The transition region may be of open mesh soft construction.

The prosthesis may be of braided mesh construction.

In one aspect the invention provides a luminal prosthesis comprising an outer region and an inner region connected to the outer region, the inner region being adapted for mounting of a device such as a valve. The inner region may be connected to the outer region by a connecting means such as struts and/or wires. The inner region may be formed by an extension of the outer region. The inner region and the outer region are formed by one continuous stent folded to form inner and outer regions. In one case the luminal prosthesis comprises a proximal flare, a bulbous region, and a scaffold receiving region.

In one embodiment the prosthesis has a reinforcement to facilitate radial compression during loading and to limit radial expansion. The reinforcement may extend around at least part of the circumference of the stent. The reinforcement may comprise at least one loop.

In one case the reinforcement is non-distensible. The reinforcement may be of flexible material. In one case the reinforcement is of a polymeric or metallic thread. The reinforcement may be a material selected from one or more of the group comprising monofilament or braided polypropylene suture or a stainless steel wire.

The invention also provides luminal self expanding prosthesis having a reinforcement to facilitate radial compression during loading and to limit radial expression. In one case the reinforcement extends around at least part of the circumference of the stent. The reinforcement may comprise at least one loop. The reinforcement may be non-distensible. The reinforcement may be of a flexible material. The reinforcement may be of a polymeric or metallic thread. The reinforcement may be of a material selected from one or more of the group comprising monofilament or braided polypropylene suture or a stainless steel wire.

The invention also provides a gastrointestinal implant device comprising a prosthesis of the invention.

Also provided is a gastrointestinal implant device comprising:
  a sleeve for extending into the duodenum;
  an artificial valve for placement at the pylorus to control flow from the stomach into the duodenal sleeve; and
  a support structure for the valve, the support structure comprising a scaffold to which the valve is mounted and a luminal prosthesis of the invention.

According to the invention there is provided a luminal prosthesis comprising an outer region and an inner region connected to the outer region, the inner region being adapted for mounting of a device such as a valve.

In one embodiment the inner region is connected to the outer region by a connecting means such as struts and/or wires.

In another embodiment the inner region is formed by an extension of the outer region. The inner region and the outer region may be formed by one continuous stent folded to form inner and outer regions.

In one case the luminal prosthesis comprises a proximal flare, a bulbous region, and a scaffold receiving region The invention also provides a gastrointestinal implant device comprising a prosthesis of the invention.

The invention provides a gastrointestinal implant device comprising:
  a sleeve for extending into the duodenum;
  an artificial valve for placement at the pylorus to control flow from the stomach into the duodenal sleeve; and
  a support structure for the valve, the support structure comprising a scaffold to which the valve is mounted and a luminal prosthesis of the invention.

According to the invention there is provided a gastrointestinal implant device comprising:
  a sleeve for extending into the duodenum; and
  an artificial valve for placement at the pylorus to control flow from the stomach into the duodenal sleeve; and
  a support structure for the valve.

The invention also provides a gastrointestinal implant device comprising:
  a sleeve for extending into the duodenum;
  an artificial valve for placement at the pylorus to control flow from the stomach into the duodenal sleeve; and
  a support structure for the valve, the support structure comprising a scaffold to which the valve is mounted and a luminal prosthesis, the luminal prosthesis comprising a proximal flare, a bulbous region, and a scaffold receiving region.

In one embodiment the scaffold receiving region is located intermediate the proximal end and the distal end of the luminal prosthesis.

The scaffold receiving region may be located between the proximal flare and the bulbous region.

In one embodiment the valve is configured to open only when a pre-set back pressure on the valve has been overcome.

In one embodiment the support structure comprises a scaffold to which the valve is mounted. The support structure may comprise a luminal prosthesis.

In one case the support structure comprises a scaffold to which the valve is mounted and a luminal prosthesis. The scaffold may be releasably mountable to the luminal prosthesis.

In one embodiment the sleeve is mounted to the support structure. In one case The sleeve is releasably mountable to the support structure. In one case the support structure comprises a scaffold and the sleeve is mounted to the scaffold.

In one embodiment the support structure comprises a stent-like structure.

In one case the support structure comprises a stent-like scaffold.

In one embodiment the support structure comprises a luminal prosthesis for deployment at the pylorus and a scaffold to which the valve is mounted, the scaffold being releasably mountable to the pre-deployed luminal prosthesis. The scaffold may be releasably engagable with the luminal prosthesis. The scaffold may comprise engagement elements which are releasably engagable with the luminal prosthesis. In one case the engagement elements comprise protrusions which are releasably engagable with the luminal prosthesis.

In one embodiment the luminal prosthesis comprises a mesh. The mesh may be coated with a coating. The protrusions may engage with the mesh. The protrusions may penetrate the mesh.

In one embodiment the device comprises a release means for releasing the scaffold from engagement with a pre-deployed luminal prosthesis. The release means may comprise means for reducing the diameter of at least a portion of the scaffold. The release means may comprise a drawstring extending around the scaffold.

There may be a first drawstring extends around a proximal end of the support structure. There may be a second drawstring extends around a distal end of the support structure.

In one embodiment the valve is mounted to the support structure. The valve may be sutured to the support structure. The valve may be bonded to the support structure. The valve may be adhesively bonded to the support structure.

In one case a proximal end of the sleeve is mounted to the support structure. The sleeve may be sutured to the support structure. The sleeve may be bonded to the support structure. The sleeve may be adhesively bonded to the support structure.

In one embodiment the support structure comprises a scaffold which is of substantially uniform diameter.

In one case the support structure comprises a luminal prosthesis.

The luminal prosthesis may comprise a proximal flare. The luminal prosthesis may comprise a distal bulbous region. The luminal prosthesis may comprise a scaffold receiving region. The scaffold receiving region may be intermediate the proximal and distal ends of the luminal prosthesis.

In one embodiment the sleeve is of substantially uniform diameter along the length thereof.

In another embodiment the sleeve has a first diameter at a proximal end and a second diameter at the distal end which is larger than the first diameter. The sleeve may be tapered.

In one embodiment the sleeve comprises a retaining means to assist in retaining the sleeve at a desired location. The retaining means may comprise a retaining ring. A retaining ring may be located at or adjacent to a distal end of the sleeve.

There may be a plurality of retaining rings which are axially spaced-apart along the sleeve.

In one case the retaining ring comprises a biasing means. The biasing means may comprise a flexible material which is biased into an expanded configuration.

In one embodiment the retaining ring is oversized with respect to the sleeve.

The device may comprise release means for releasing the retaining ring from engagement. The release means may comprise a drawstring.

In one embodiment the sleeve has a retracted delivery configuration and an expanded deployed configuration. The sleeve may be folded in the retracted delivery configuration.

In one embodiment the valve has a normally closed configuration and an open configuration in which the valve is opened for stomach emptying.

In one case the valve is adapted to open automatically for stomach emptying and to return automatically to the closed configuration.

The valve may be of a viscoelastic polymeric foam which may be biomimetic.

In one embodiment the valve comprises an outer support region, at least three valve leaflets, and a main body region extending between the support region and the valve leaflets. The valve may have a region of co-aption of the valve leaflets in the closed configuration. The region of co-aption may extend for an axial length of at least 1 mm.

In one embodiment the device is adapted for placement in the pyloric sphincter or valve.

In another embodiment the device is adapted for placement distal of the pyloric sphincter.

In one embodiment the support is adapted for mounting to a pre-deployed sleeve which extends into the duodenum.

The invention also provides a delivery system for a gastrointestinal implant device, the implant device comprising an artificial valve, a duodenal sleeve and a support structure for the valve and the sleeve, the device having a retracted delivery configuration and an expanded deployed configuration, the delivery system comprising a delivery catheter having a distal pod for the implant device in the retracted configuration; and a sleeve deployment system.

In one case the sleeve deployment system comprises:
a distal cap;
a fluid delivery lumen for extending through the sleeve;
a distal seal between the distal cap and the lumen; and
a proximal seal,
whereby delivery of fluid through the lumen and into the sleeve causes the sleeve to expand from an axially retracted delivery configuration to an axially expanded deployed configuration.

The proximal seal may be sealingly engagable with the pod for deployment of the sleeve.

The proximal seal may be sealingly engagable with the valve for deployment of the sleeve.

In one case the pod is detachable from the delivery catheter.

The proximal seal may comprise an inflatable balloon.

The distal seal may comprise an inflatable balloon. The delivery system may include a flexible tube for inflating the distal balloon.

The delivery system in one embodiment comprises a deployer for deploying the support structure and the valve to which the support structure is mounted. In one case the deployer comprises an abutment. The abutment may be provided by a balloon. The deployer balloon may comprise the proximal balloon.

In one embodiment the distal cap or olive is releasably mounted to the fluid delivery lumen.

The invention also provides a gastrointestinal implant comprising a sleeve for extending into the duodenum, the sleeve having a pocket containing a radiopaque marker. The pocket may extend at least partially along the length of the sleeve.

In one embodiment the sleeve has a plurality of pockets for reception of a radiopaque marker.

The radiopaque marker may comprise a fluid or gel. The fluid may comprise a silicon resin filled with a radiopaque material such as barium sulphate.

The invention also provides a method for treating obesity and/or diabetes comprising the steps of:
  providing a luminal prosthesis;
  providing a valve mounted to a support scaffold, the valve having a retracted delivery configuration and an expanded deployed configuration;
  providing a liner sleeve for lining the duodenum;
  delivering the luminal prosthesis to a location at or distal of the pylorus;
  deploying the luminal prosthesis at the location in the pylorus;
  delivering the valve and support scaffold to the location; and
  deploying the sleeve so that the sleeve extends from the valve and into the duodenum.

In one embodiment the method comprises deploying the valve and support structure so that the support structure engages with the predeployed luminal prosthesis.

In one embodiment the luminal prosthesis is deployed in the pyloric sphincter.

In another embodiment the luminal prosthesis is deployed distal of the pyloric sphincter.

The method may comprise releasing the valve support structure from engagement with the luminal prosthesis; and withdrawing the valve support structure, the valve, and the sleeve from the location. The method may comprise repeating the appropriate steps to deploy a valve, a support structure for the valve, and a sleeve at the desired location.

The invention further provides a method for treating obesity and/or diabetes comprising the steps of:
  providing a valve mounted to a support structure;
  delivering the valve mounted to the support structure to a pre-deployed sleeve which extends into the duodenum; and
  deploying the valve so that the valve is mounted to the sleeve.

The step of deploying the valve may comprise engaging the valve support with the pre-deployed luminal prosthesis.

In one case the valve support is an expandable support and the method comprises loading the support onto a delivery catheter in a retracted form and the valve support is expandable on deployment. The support may be self expandable. The support may be expanded by an expanding means such as a balloon.

In one case the method comprises the step of releasing the valve support from engagement with the luminal prosthesis.

The method may comprise repositioning the valve support within the sleeve. The valve may be removed from the sleeve.

The invention also provides a gastrointestinal implant device comprising a pyloric valve for placement at the pylorus to control flow from the stomach into the duodenum, the valve being of a viscoelastic foam and comprising at least three valve leaflets,
  the valve having a normally closed configuration and an open configuration,
  the valve leaflets being movable from the closed configuration to the open configuration for flow from the stomach.

In one embodiment the valve is adapted to open automatically for stomach emptying and to return automatically to the closed configuration. The valve may comprise an outer support region and a main body region extending between the support region and the valve leaflets. The valve may have a region of co-aption of the valve leaflets in the closed configuration.

In one case the device comprises an anchor for anchoring the valve at the pylorus.

In one case the anchor comprises a support structure for the valve. The anchor may comprise a support scaffold for the valve and a luminal prosthesis to which the scaffold is mountable.

In one case the device comprises a sleeve for extending into the duodenum. The sleeve may be mounted to the valve or to an anchor for the valve. The device may be adapted for placement in the pyloric sphincter or may be adapted for placement distal of the pyloric sphincter.

According to the invention there is provided a gastrointestinal implant device comprising a valve for placement at the pylorus to control the rate of stomach emptying.

In one embodiment the valve has a normally closed configuration and an open configuration in which the valve is opened for stomach emptying.

There may be a support for the valve. The support may be adapted for mounting to a pre-deployed sleeve which extends into the duodenum.

In one embodiment the implant device is adapted for placement in the pyloric valve.

In a further embodiment the implant device is adapted for placement distal of the pyloric valve.

The valve support may comprise a support structure. The support structure may taper outwardly.

The support structure may taper inwardly.

In another case the support structure is of generally uniform diameter along the length hereof.

The support structure may comprise a scaffold.

The support structure may comprise a stent-like structure.

In one case the device comprises mounting means for mounting the valve support to a pre-deployed luminal prosthesis.

The mounting means may be releasably engagable with a pre-deployed host support.

The device may comprise release means for releasing the valve from engagement with a pre-deployed host support. The release means may comprise means for reducing the diameter of at least portion of the valve support structure. The release means may comprise a drawstring extending around the valve support structure. There may be a first drawstring which extends around a proximal end of the support structure. There may be a second drawstring which extends around a distal end of the support structure.

In one case the valve is mounted to the support structure. The valve may be sutured to the support structure.

The valve may be bonded to the support structure. The valve may be adhesively bonded to the support structure.

In one embodiment the valve is adapted to open automatically in the one direction.

The invention also provides a method for treating obesity and/or diabetes comprising the steps of:
 providing a valve mounted to a support structure;
 delivering the valve mounted to the support structure to a pre-deployed sleeve which extends into the duodenum; and
 deploying the valve so that the valve is mounted to the sleeve.

The step of deploying the valve may comprise engaging the valve support with the pre-deployed luminal prosthesis.

In one case the valve support an expandable support and the method comprises loading the support onto a delivery catheter in a retracted form and the valve support is expandable on deployment.

The support may be self expandable. Alternatively the support is expanded by an expanding means. The expanding means may comprise a balloon.

In one embodiment the method comprises the step of releasing the valve support from engagement with the luminal prosthesis. The method may comprise repositioning the valve support within the sleeve.

In one case the method comprises removing the valve from the sleeve.

In one embodiment the valve comprises a polymeric valve body having an outer support rim, at least three valve leaflets, and a main body region extending between the support rim and the valve leaflets.

The invention also provides a valve comprising at least four valve leaflets, the valve having a normally closed configuration in which the leaflets are engaged and an open configuration in which the leaflets are open. There may be at least five valve leaflets. There may be six valve leaflets.

The valve may comprise a valve body of polymeric material. The valve may comprise an outer support region. The valve may also have a main body region extending between the support region and the valve leaflets.

In one case the main body region is generally concave between the outer support rim and a region of co-aption of the valve leaflets.

In one case the valve leaflets have a region of co-aption and the valve body is reinforced at the region of co-aption. The valve body may be thickened at the region of co-aption.

The region of co-aption may extend for an axial length of at least 1 mm. The region of co-aption may extend for a depth of from 1 mm to 5 mm.

In one embodiment the support rim of the valve body is reinforced. The support rim of the valve may be thickened.

In one embodiment the valve comprises three valve leaflets.

In another embodiment the valve comprises six valve leaflets.

The valve may be mounted to the support structure.

In one case the valve rim is sutured to the support structure. Alternatively or additionally the valve rim is bonded to the support structure.

In one embodiment the support structure comprises a luminal prosthesis.

In one case the luminal prosthesis extends proximally of the valve.

In another case the luminal prosthesis extends distally of the valve.

In one embodiment the luminal prosthesis extends proximally and distally of the valve.

The luminal prosthesis may have a coating and/or a sleeve thereon. The coating or sleeve may be on the outside of the luminal prosthesis. Alternatively the coating or sleeve is on the inside of the luminal prosthesis.

In one embodiment the polymeric material is stable to gastric fluid for at least 3 months, for at least 4 months, for at least 5 months, for at least 6 months, for at least 7 months, for at least 8 months, for at least 9 months, for at least 10 months, for at least 11 months, or for at least one year.

In one case the polymeric material takes up less than about 5%, less than about 10%, less than about 15%, less than about 20%, less than about 25%, or less than about 30% by weight of water at equilibrium.

In one case the polymeric material of the valve body has a % elongation of from 50% to 3000% or 200% to 1200%.

In one case the polymeric material of the valve body has a tensile strength of from 0.01 to 5 MPa or about 0.1 to 1.0 MPa, or about 0.25 to 0.5 MPa.

In one embodiment the polymeric material has a Young's Modulus of about 0.01 to 0.6 MPa, or about 0.1 to about 0.5 MPa.

In one embodiment the polymeric material of the valve body has a density of from 0.1 g/cm$^3$ to 1.5 g/cm$^3$, or 0.3 to 1.2 g/cm$^3$, or 0.8 to 0.9 g/cm$^3$, or 0.5 to 0.6 g/cm$^3$.

In one embodiment the distance between the proximal end of the support region of the valve body and the distal end of the valve leaflets is less than 50 mm, or less than 40 mm, or less than 30 mm, or less than 25 mm, or less than 20 mm, or less than 15 mm.

In one case the polymeric material of the valve body is of an elastic material.

In another case the polymeric material of the valve body is of a viscoelastic material.

In one embodiment the polymeric material of the valve body comprises a foam. The polymeric material of the valve body may comprise an open cell foam.

In one embodiment the polymeric material of the valve body comprises a polyurethane foam.

In one embodiment the valve is adapted to be mounted to a pre-deployed support structure, for example an esophageal luminal prosthesis such as a stent.

The invention also provides a valve having:
 a normally closed configuration in which the valve is closed;
 an open configuration in which the valve is opened for flow through the valve; and
 a support for the valve, the support being adapted for mounting to a pre-deployed luminal prosthesis intermediate a proximal end and a distal end of the predeployed luminal prosthesis.

In one case the luminal prosthesis has a coating and/or sleeve thereon. The coating or sleeve may be on the outside of the luminal prosthesis. Alternatively or additionally the coating or sleeve is on the inside of the luminal prosthesis.

The mounting means may be provided by the support structure. In one case the mounting means comprises protrusions extending from the support structure. The protrusions may be adapted to engage with a pre-deployed host esophageal luminal prosthesis.

In one embodiment the protrusion comprises a loop.

In one case the apicial tip of the protrusion is rounded.

There may be release means for releasing the valve from engagement with a pre-deployed host luminal prosthesis. The release means may comprise means for reducing the diameter of at least portion of the valve support structure.

In one case the release means comprises a drawstring extending around the valve support structure. A first drawstring may extend around a proximal end of the support structure. A second drawstring may extend around a distal end of the support structure.

In one embodiment the valve is mounted to the support structure. The valve may be sutured to the support structure. The valve may be bonded to the support structure. The valve may be adhesively bonded to the support structure.

In another case the mounting means comprises a surgical adhesive.

The invention also provides a method for providing a valve in a body passageway comprising the steps of:
providing a valve mounted to a support structure;
delivering the valve mounted to the support structure to a pre-deployed luminal prosthesis in the body passageway; and
deploying the valve so that the valve is mounted to the luminal prosthesis.

In one embodiment the step of deploying the valve comprises engaging the valve support with the pre-deployed luminal prosthesis.

The valve support may be mechanically engaged with the pre-deployed luminal prosthesis.

In one case the valve support comprises a protrusion and the method comprises aligning the protrusion with an aperture in the endoluminal prosthesis and engaging the protrusion in the aperture.

In one embodiment the valve support is an expandable support and the method comprises loading the support onto a delivery catheter in a retracted form and the valve support is extendable on deployment.

The support may be self expandable or the support is expanded by an expanding means such as a balloon.

In one embodiment the method comprises the step of releasing the valve support from engagement with the luminal prosthesis.

The method may involve repositioning the valve support within the prosthesis. The method may comprise removing the valve from the prosthesis.

In one embodiment the luminal prosthesis extends proximally of the valve. The prosthesis may comprise a self expanding plastics mesh. The prosthesis may apply a radial force of less than 1.9 kPa.

In one embodiment there are anchors for mounting the prosthesis in situ. The anchors may be adapted to extend through the mesh of the prosthesis.

In one embodiment the length of the valve from the proximal end of the support region to the distal end of the valve leaflets is less than 50 mm, less than 40 mm, less than 30 mm. The length of the valve may be approximately the same as the outer diameter of the support region of the valve. The length of the valve may be approximately 23 mm.

BRIEF DESCRIPTION OF THE DRAWINGS

The invention will be more clearly understood from the following description thereof given by way of example only, in which:
FIG. 3 is a top plan view of the valve;
FIG. 4 is an underneath plan view of the valve;
FIGS. 5 and 6 are elevational views of the valve;
FIG. 17 is an isometric view of a prosthesis;
FIG. 18 is an elevational view of the valve of FIGS. 1 to 16 being mounted to and in position on the prosthesis of FIG. 17;
FIG. 19 is another view of the valve mounted in a prosthesis;
FIG. 29 is an elevational view of a luminal prosthesis with a valve and associated support structure in place;
FIG. 30 is an enlarged view of the luminal prosthesis and valve support structure of FIG. 29;
FIGS. 31 and 32 are enlarged views of one mounting detail of a valve support structure to a luminal prosthesis;
FIGS. 33 to 37 are views of a valve being deployed from a delivery catheter;
FIGS. 38 to 40 are views of a luminal prosthesis in situ with a valve being deployed in the lumen of the luminal prosthesis.
FIG. 41 is an elevational view of a valve according to another embodiment of the invention;
FIG. 42 is an enlarged view of a detail of the support structure of the valve of FIG. 41;
FIGS. 50 to 55 are elevational views of steps involved in deploying the valve of FIG. 49 into a pre-deployed luminal prosthesis of FIG. 48;
FIG. 56 is an elevational view of the valve of FIG. 49 deployed in the luminal prosthesis of FIG. 55;

FIG. 57 is an elevational view similar to FIG. 56 with the valve being removed from the deployed prosthesis;

FIG. 66 is an illustration of a gastrointestinal implant device according to one embodiment of the invention;

FIG. 67 is an enlarged view of detail A of FIG. 66;

FIGS. 68 and 69 are illustrations of another gastrointestinal implant device located in the pyloric sphincter;

FIGS. 70 and 71 are illustrations similar to FIGS. 66 and 67 with the device located distal of the pyloric sphincter;

FIG. 72 is an isometric view of a luminal prosthesis of an implant device of the invention;

FIG. 73 is an elevational view of a valve, sleeve and scaffold part of an implant device;

FIG. 81 is an elevational, partially cross sectional view of an implant device including a retaining ring for a sleeve;

FIG. 82 is a view similar to FIG. 81 of another sleeve;

FIG. 83 is a view similar to FIG. 81 with a sleeve having a plurality of retaining rings;

FIGS. 92 to 94 are views showing the delivery system at various stages;

FIG. 96 is an elevational view of part of the delivery system;

FIG. 97 is an exploded view of part of delivery system of FIG. 96;

FIG. 123 an isometric view of a further luminal prosthesis according to the invention;

FIGS. 124 and 125 are diagrams illustrating different configurations of the prosthesis of

FIG. 123;

DETAILED DESCRIPTION

Figure 2:
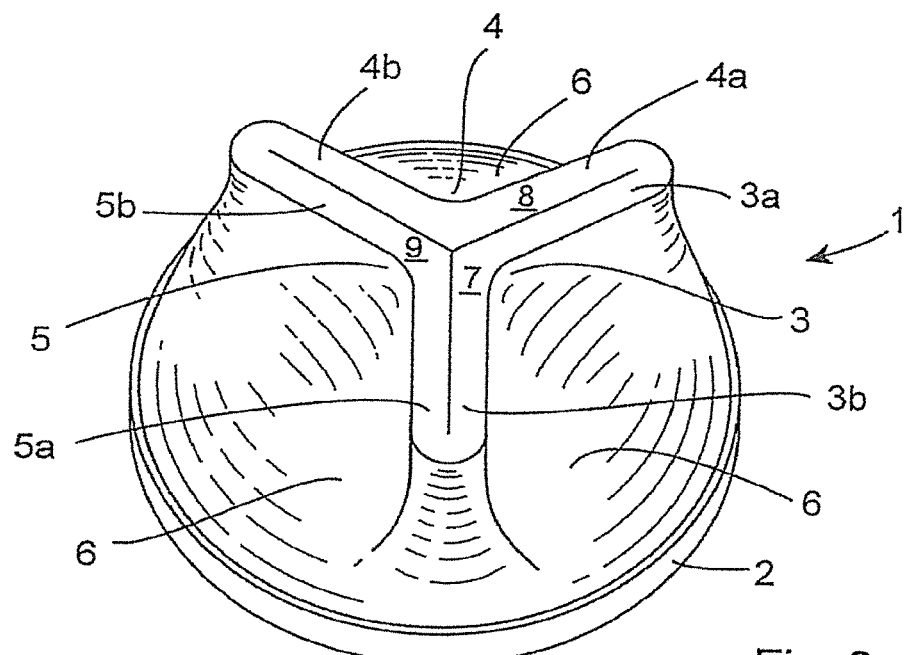
FIG. 2 is an isometric view (from below) of the valve.

Referring to the drawings and initially to FIGS. 1 to 16 thereof there is illustrated a valve 1 which can open automatically in one direction.

The valve 1 comprises a polymeric valve body having a proximal outer support region with a rim 2, at least three valve leaflets 3, 4, 5, and a main body region 6 extending between the support rim 2 and the valve leaflets 3, 4, 5. The valve leaflets 3, 4, 5 extend inwardly and distally and terminate at distal end faces 7, 8, 9 respectively. The leaflets each 3, 4, 5 have legs a, b which extend at an included angle of 120° to each other. The adjacent pairs of legs 3a; 4a; 4b; 5b; 5a; 3b; co-apt to close the gap between the valve leaflets when the valve is in the normally closed configuration.

The valve 1 has two configurations. The first configuration is a normally closed configuration in which the valve leaflets 3, 4, 5 co-apt to close the valve. The second configuration is an open configuration in which the valve leaflets 3, 4, 5 are opened such that the leaflet leg pairs 3a; 4a; 4b; 5b; 5a; 3b are opened and spaced-apart in response to a force F1 to allow flow through the valve.

Figures 11, 12:
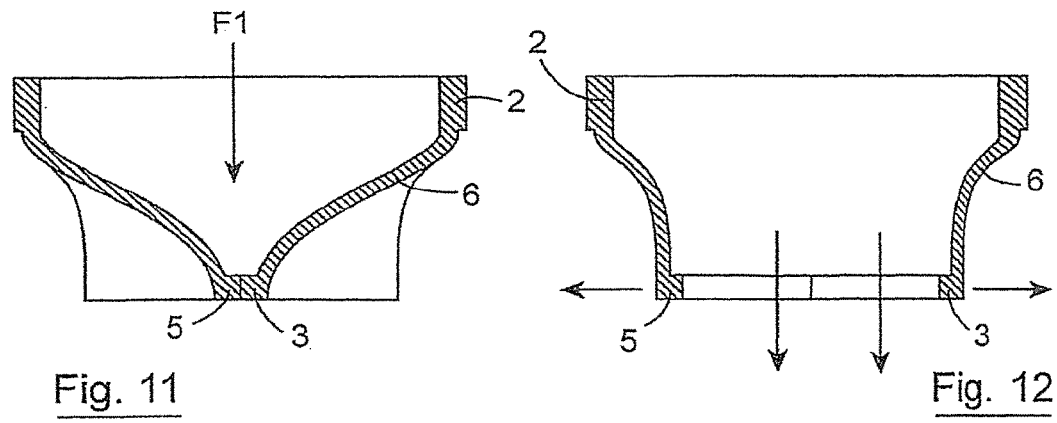
FIG. 11 is a cross sectional view of the valve in a normally closed configuration.
FIG. 12 is a cross sectional view of the valve in an open configuration in response to a force.
Figures 13, 14:
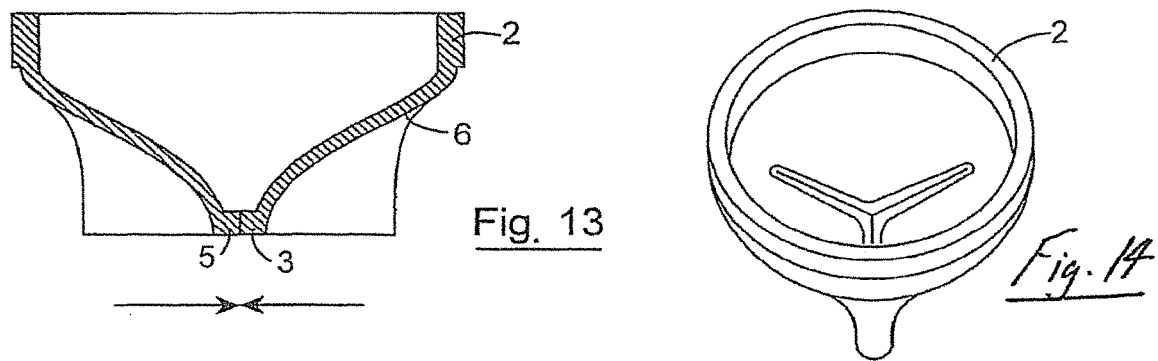
FIG. 13 is a cross sectional view of the valve returned to the closed configuration after opening to flow.
FIG. 14 is an isometric view (from above) of the valve in a normally closed configuration.
Figures 15, 16:
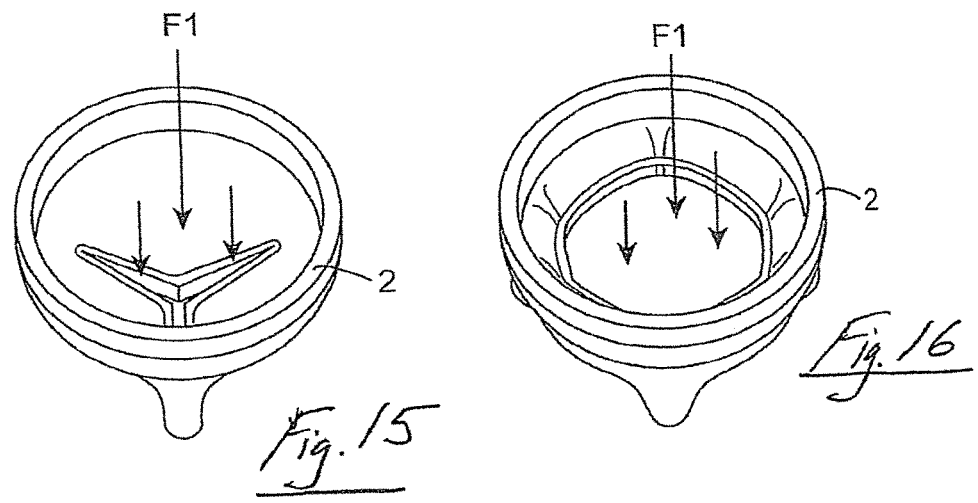
FIG. 15 is an isometric view of the valve in a partially open configuration in response to a force.
FIG. 16 is an isometric view of the valve in a fully open configuration in response to a force.
Figures 20, 21, 23:
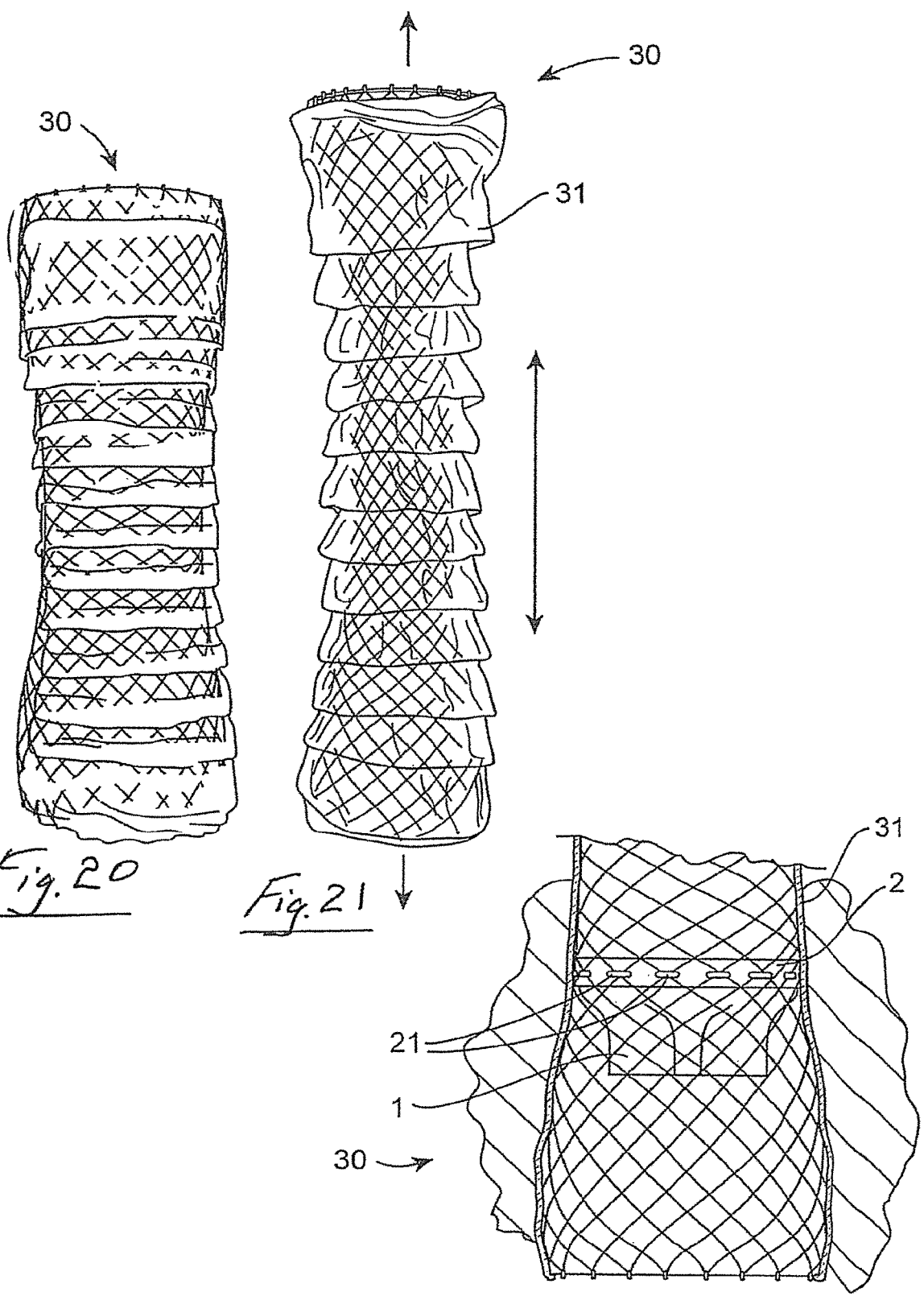
FIGS. 20 and 21 are isometric views of a sleeved or coated prosthesis.
FIG. 23 is an elevational view of part of the prosthesis of FIG. 22 in position.
Figure 22:
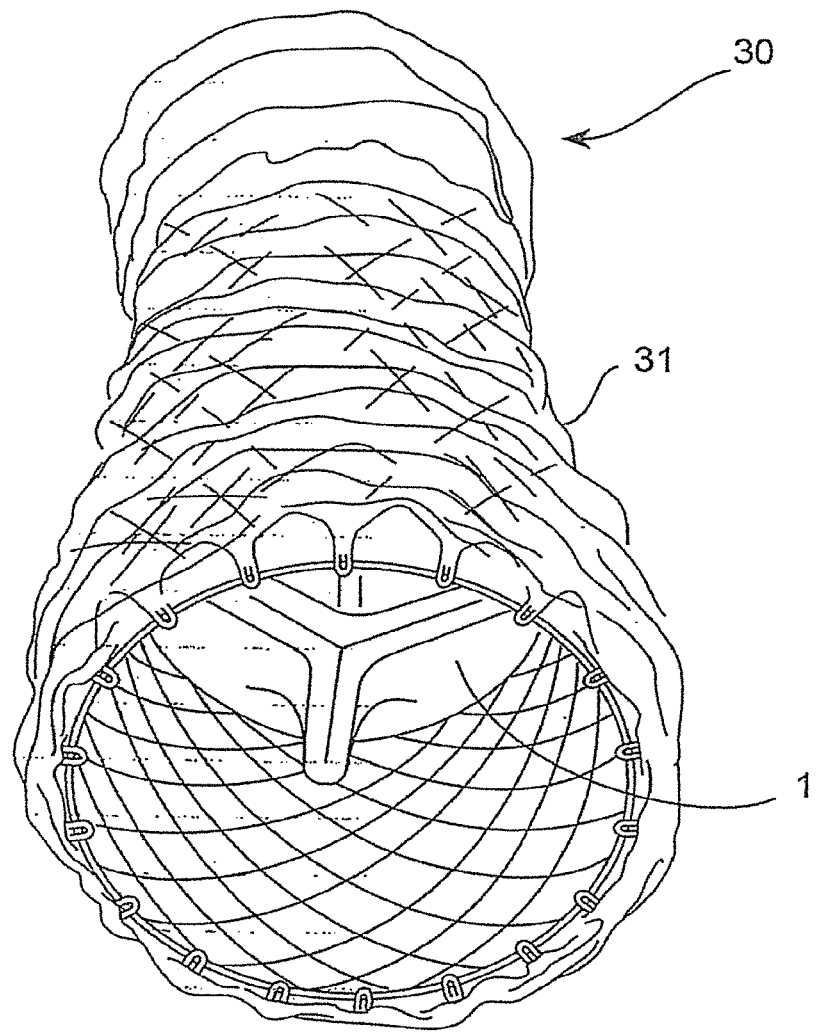
FIG. 22 is an isometric view of the prosthesis of FIGS. 20 and 21 with a valve of FIGS. 1 to 16 in position.

The various configurations of the valve 1 are illustrated in FIGS. 11 to 16. In the first or normally closed configuration (FIGS. 11, 14) the valve leaflets 3, 4, 5 co-apt. When a force F1 is applied to the valve leaflets 3, 4, 5 the leaflet legs pairs 3a; 4a; 4b; 5b; and 5a; 3b open to allow antegrade flow to pass (FIGS. 12, 16). FIG. 15 illustrates a partially open configuration in response to flow. When the force F1 is removed the leaflets 3, 4, 5 return to the closed position under the inherent biasing of the polymeric material of the valve body (FIG. 13).

The valve leaflets 3, 4, 5 are reinforced in the region of co-aption. In this case, this is achieved by a local thickening of the polymeric material in this region. Similarly the support rim 2 is reinforced by a local thickening of the polymeric material.

The region of co-aption of the valve leaflets 3, 4, 5 has an axial extent which is typically from 1 to 5 mm. This ensures positive co-aption of the leaflets across a significant interfacial area when the valve is in the normally closed configuration. The thickness of the leaflets at the region of co-aption is typically between 0.1 mm and 10 mm.

The valve body has a generally concave outer face and a generally convex inner face.

The valve 1 of the invention returns to its original working position after being fully opened. This is accomplished without damaging the working valve.

When the valve is opened by stomach emptying the leaflets open.

One important characteristic influencing the functioning of the valve is the leaflet legs that impinge on one another. By varying the geometry and length of the leaflets 3, 4, 5 the valve 1 can be made to open at different pressures. Opening is also dependant on the elasticity and density of the material the device is made from. Additionally, the overall diameter and the diameter to which the leaflets open influence the opening force.

The valve may be of any suitable biocompatible polymeric material. It may be of a biocompatible polymeric material having properties which allow the valve to function as described.

The materials used for the production of this valve have a % elongation between 50% and 3000%. The material also has a tensile strength of between 0.01 and 5 MPa. Additionally the material could have an antimicrobial action to prevent colonisation when in-vivo. Additionally the material can be elastic or viscoelastic and can optionally be an open cell foam. The density of the material should be between 0.1 g/cm3 to 1.5 g/cm3.

The valve of the invention may be mounted to any suitable luminal prosthesis, especially a prosthesis or stent. The rim 2 of the valve provides a mounting ring for mounting within the stent 20, for example, the valve 1 may be mounted to the stent by suturing the rim 2 to the stent mesh using sutures 21 as illustrated in FIGS. 18 and 19.

The stent may be of any suitable type. An uncoated or unsleeved stent 20 is illustrated in FIGS. 17 to 19. Alternatively, if it is desired to prevent tissue ingrowth a stent 30 having a sleeve 31 may be used (FIGS. 20 to 23). In this case the sleeve 31 is external of the stent. In other cases there may alternatively or additionally be an internal sleeve. Further, the stent may have a coating.

A valve such as described above may also be placed into a pre-deployed luminal prosthesis.

Figure 25:
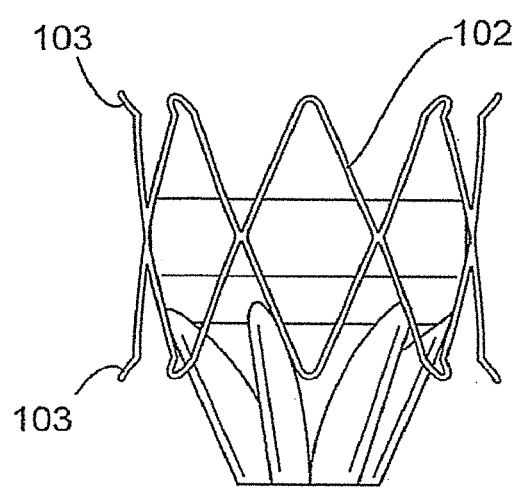
FIG. 25 is an elevational view of the valve of FIG. 24.
Figure 24:
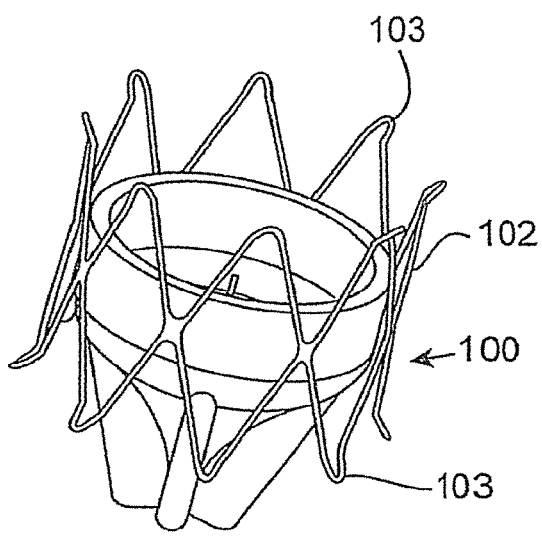
FIG. 24 is an isometric view of a valve according to another embodiment of the invention.

In one case a valve 100 may have a co-axial support structure or scaffold 102 is shown in FIGS. 24 and 25. The scaffold 102 is designed to engage with any suitable esophageal stent 140 as illustrated in FIG. 29. The mechanism of engagement can be by protrusions which may for example be proximal and/or distal apices 103 of the scaffold 102 which engage into the mesh of the existing pre-deployed stent 140. Alternatively or additionally, the scaffold 102 may have features 150 designed to hook onto the inside of the struts of an esophageal stent as illustrated in FIGS. 31 and 32.

Figure 27:
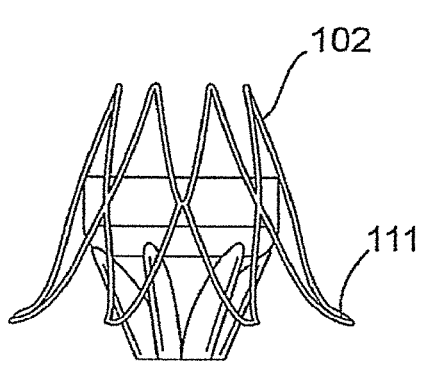
FIG. 27 is an elevational view of the valve of FIG. 26.
Figure 26:
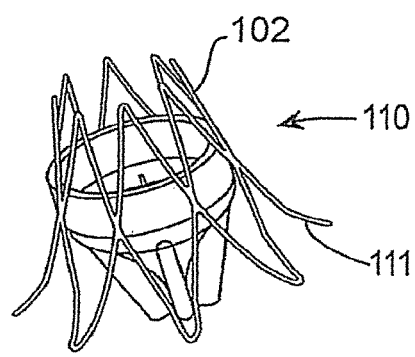
FIG. 26 is an isometric view of another valve according to the invention with a distally outward tapering support structure.

Referring to FIGS. 26 and 27 there is illustrated a valve 110 according to another embodiment of the invention in which the support structure or scaffold 102 tapers distally outwardly so that distal apices 111 of the scaffold engage with the mesh of the existing pre-deployed host stent 140.

Figure 28:
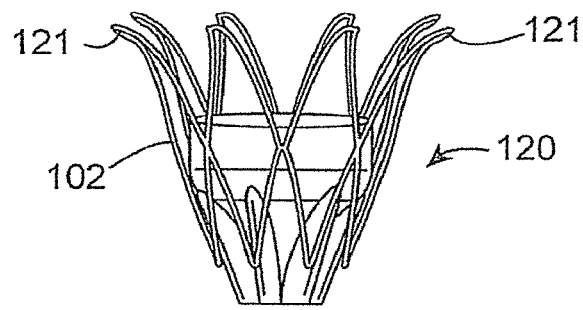
FIG. 28 is an isometric view of another valve according to the invention with a distally inward tapering support structure.

Referring to FIG. 28 there is illustrated another valve 120 according to the invention in which the support structure or scaffold 102 tapers distally inward so that proximal apices 121 of the scaffold 102 engage with the mesh of an existing pre-deployed stent 140.

The radial force of the scaffold 102 may exert enough friction to hold the valve in place without the necessity for protrusion. In another embodiment a surgical adhesive may be used to secure the retrofitted valve into place.

Referring to FIGS. 33 to 37 a valve 100 is loaded into a delivery system 130 for deployment. The outer diameter of the delivery system 130 is smaller than the inner diameter of a pre-deployed esophageal stent 140. The delivery system 130 in this case comprises a delivery catheter having a distal pod 131 in which a valve is housed in a contracted configuration. The catheter has a tapered distal tip 132 to avoid snagging on a pre-deployed stent 140. The pod 131 is axially movable relative to the tip 132 to release the valve from the pod 131.

The delivery system 130 is used to deliver the valve to a pre-deployed stent 140 as illustrated in FIG. 38. The stent 140 has a mesh and the scaffold of the valve is adapted to engage with the mesh of the pre-deployed stent 140 on release of the valve from the delivery catheter as illustrated particularly in FIGS. 39 and 40.

Referring to FIGS. 29 to 32 there is illustrated an idealised stent 140 with a valve support scaffold 102 in situ. Details of a valve are omitted from these drawings for clarity. In this case the scaffold 102 is located at the upper proximal end of the stent. In this case the scaffold 102 has hook-like members 150 for engagement with the mesh of the stent 140 as illustrated in FIGS. 31 and 32. The interengagement between the stent 140 and the scaffold 102 ensures that the scaffold 102 and hence the valve which is fixed to it is retained in position and provides an anti-proximal migration mechanism.

In the cases illustrated the valve supporting scaffold 102 is of a self expanding material such as a shape memory material, for example Nitinol. The valve and scaffold are loaded into the delivery catheter pod 131 in a compressed/reduced diameter configuration. When the constraint of the pod 131 is removed at the deployment site, the scaffold and valve self expand to the normal configuration in which the scaffold is engaged with the pre-deployed host stent 140. In some arrangements the scaffold may be of an expensile material which is expanded by an expander such as a balloon or the like.

Figures 43, 44:
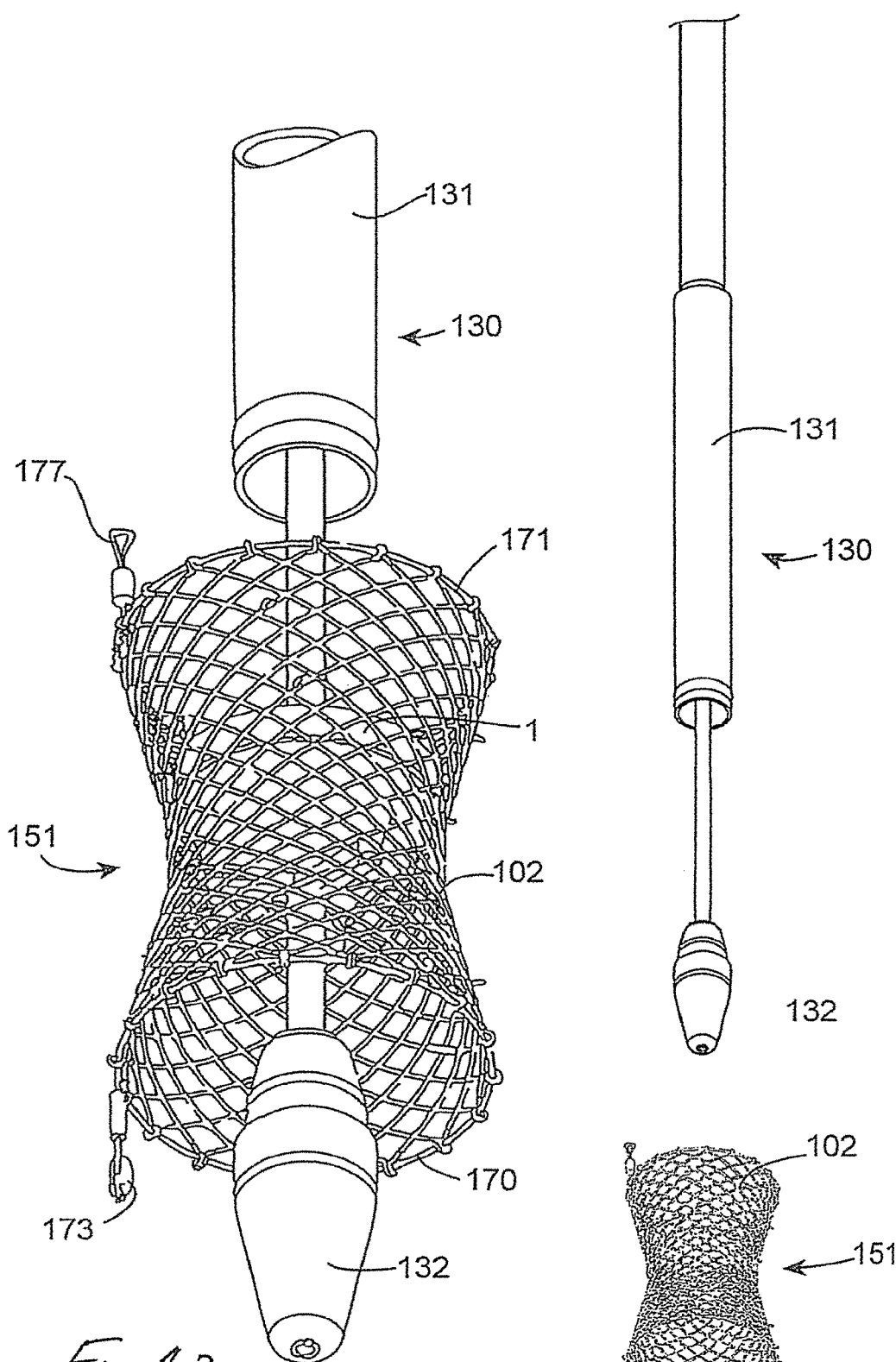
FIGS. 43 and 44 are isometric views of the valve of FIGS. 41 and 42 being deployed from a delivery catheter.
Figure 45:
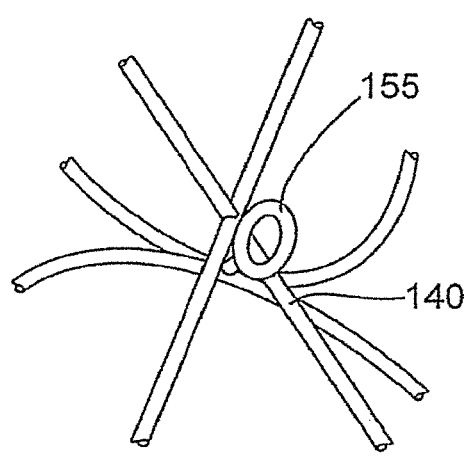
FIG. 45 is an elevational view of a prosthesis with the valve of FIGS. 43 and 44 in situ.
Figure 46:
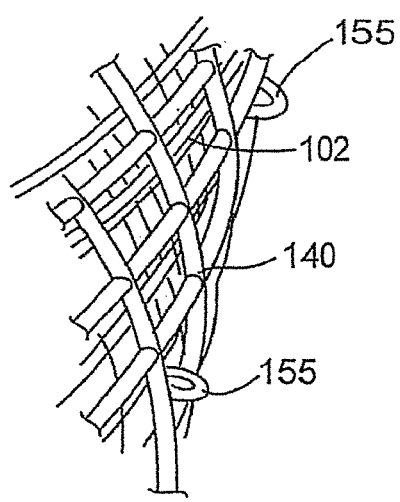
FIG. 46 is an enlarged view of a detail of the engagement of the valve support structure of FIGS. 41 to 45 engaged in the mesh of the prosthesis.
Figure 47:
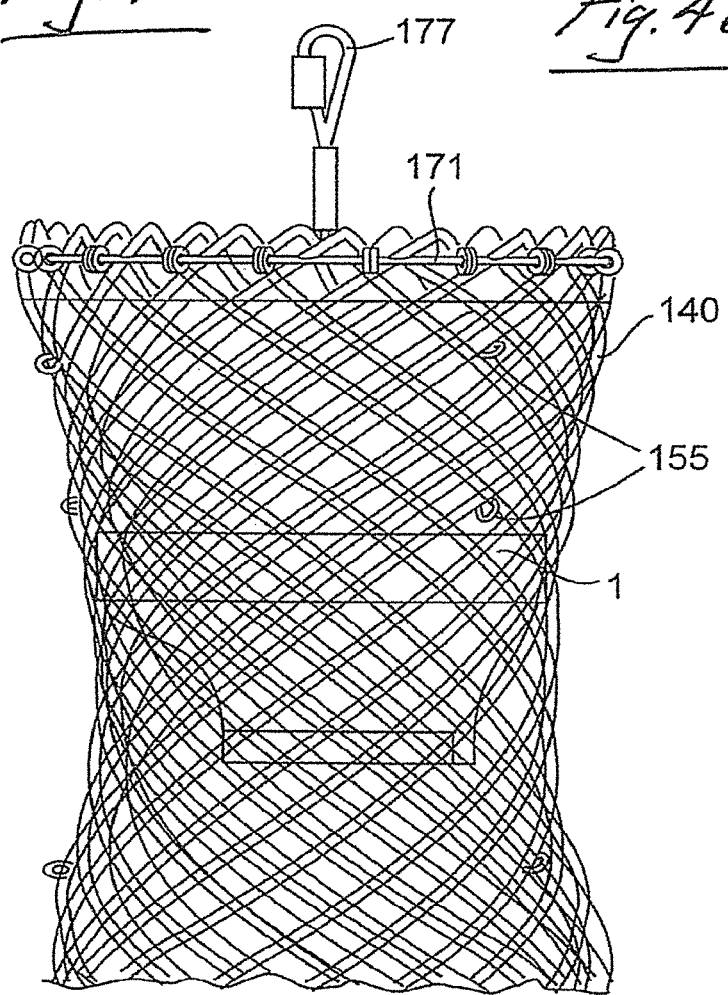
FIG. 47 is an enlarged view of part of the luminal prosthesis and valve support structure of FIG. 46.
Figures 48, 49:
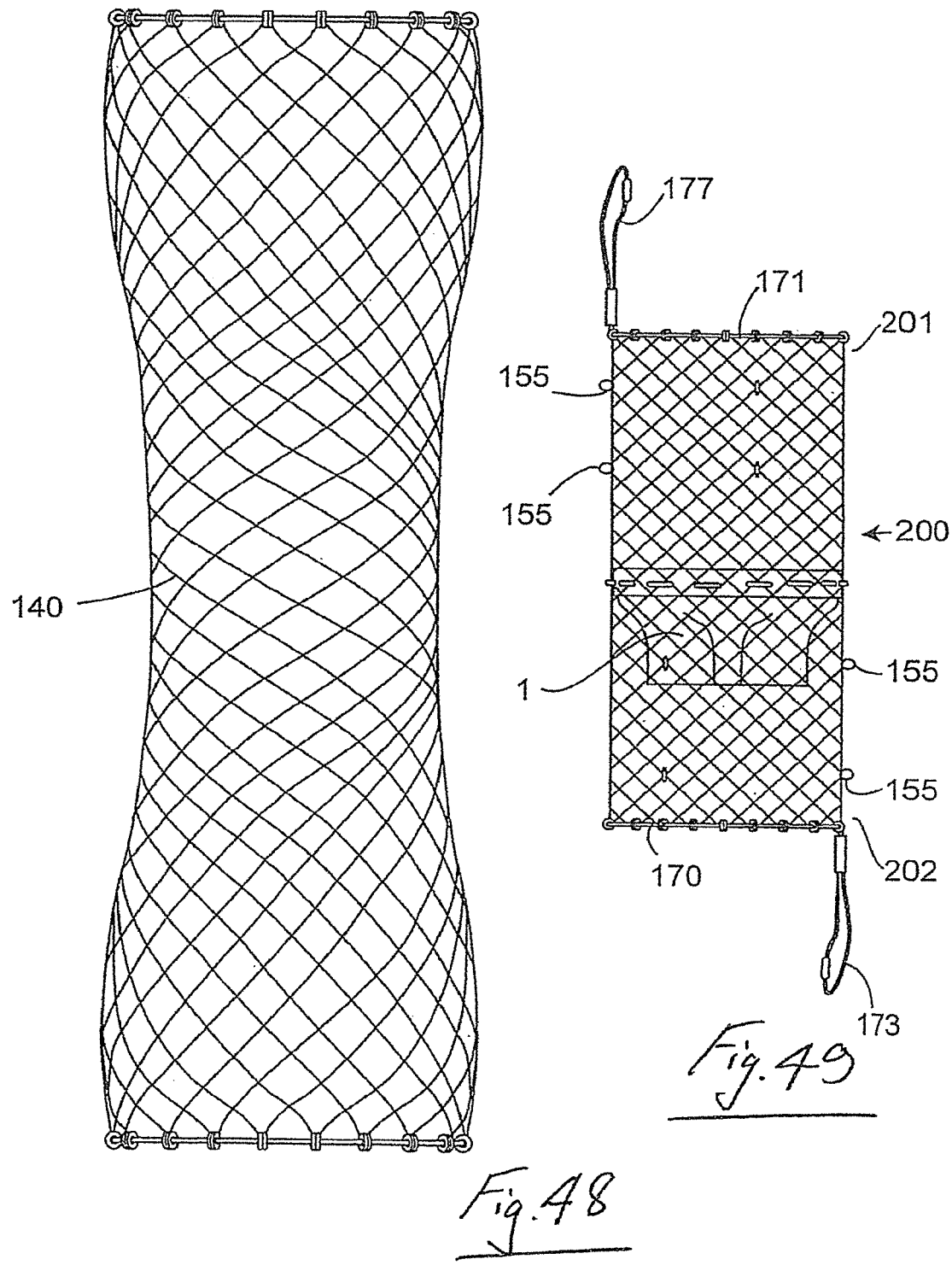
FIG. 48 is an elevational view of a luminal prosthesis.
FIG. 49 is an elevational of an esophageal valve of the invention.
Figure 58:
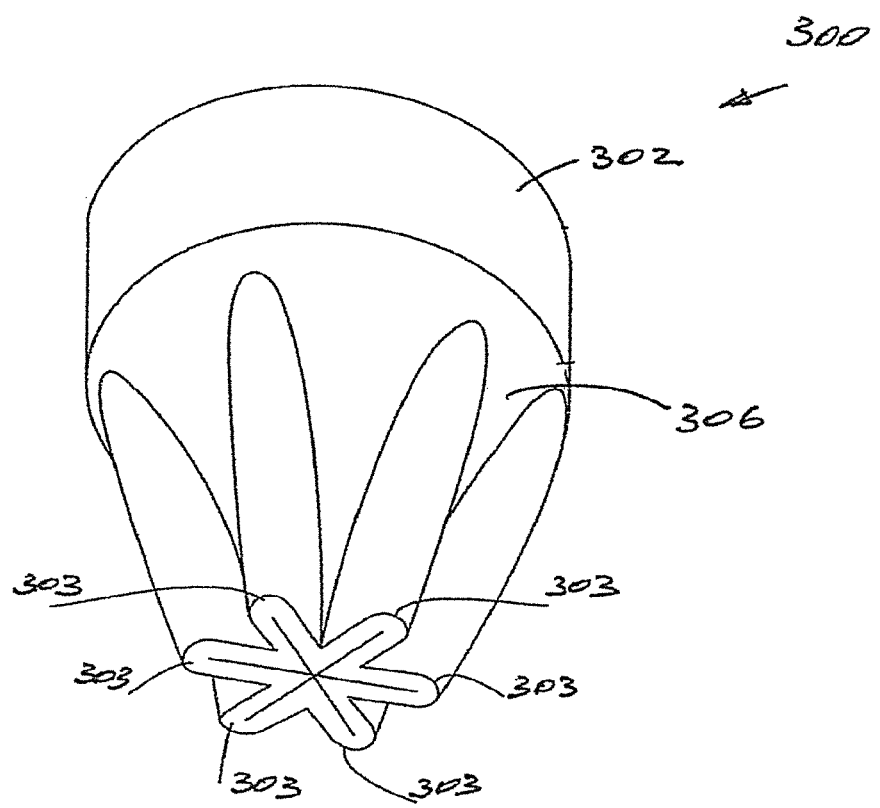
FIG. 58 is an isometric view of a valve according to the invention.
Figure 59:
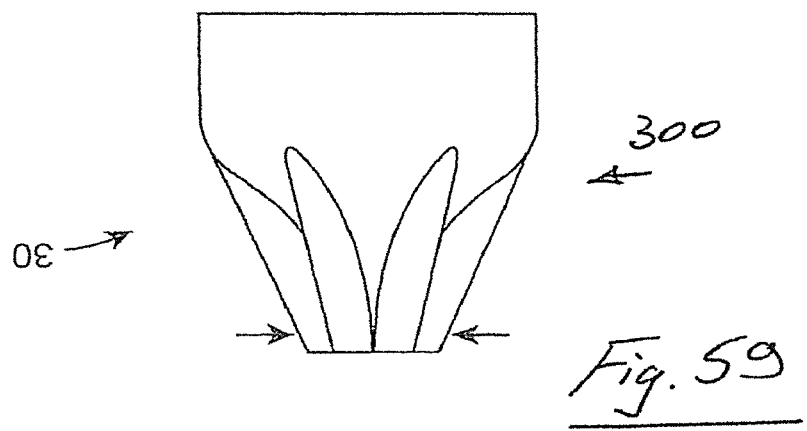
FIG. 59 is an elevational view of the valve of FIG. 56.
Figure 60:
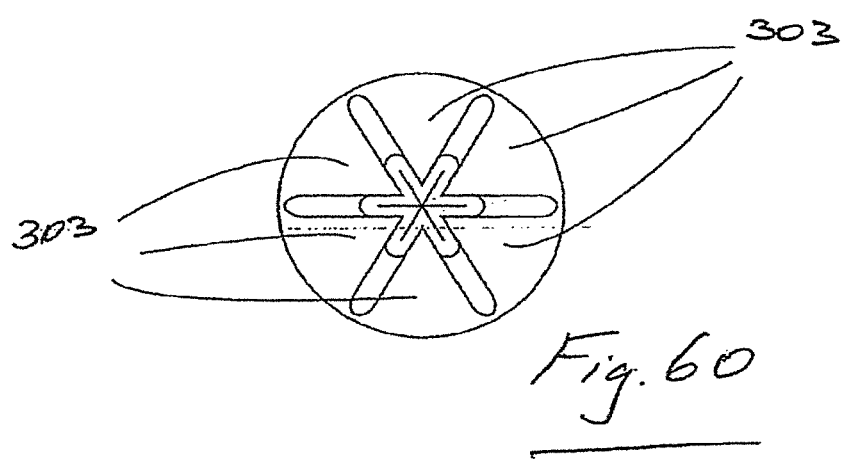
FIG. 60 is a plan view of the valve of FIGS. 58 and 59 with the valve in a closed configuration.
Figure 61:
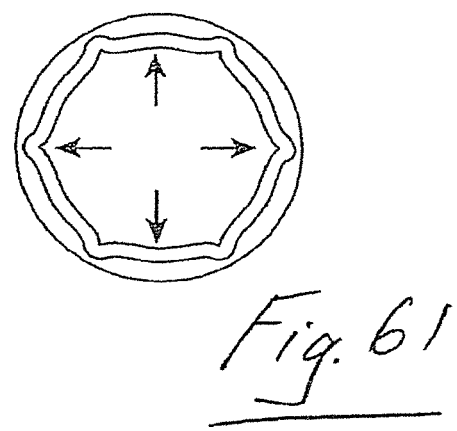
FIG. 61 is a plan view similar to FIG. 60 with the valve in an open configuration.
Figure 62:
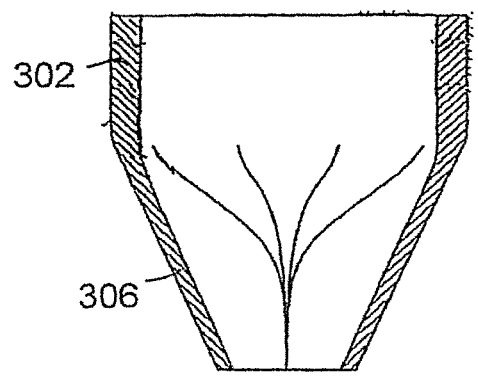
FIGS. 62 and 63 are side views of the device of FIG. 60 with the valve in a closed configuration.
Figure 64:
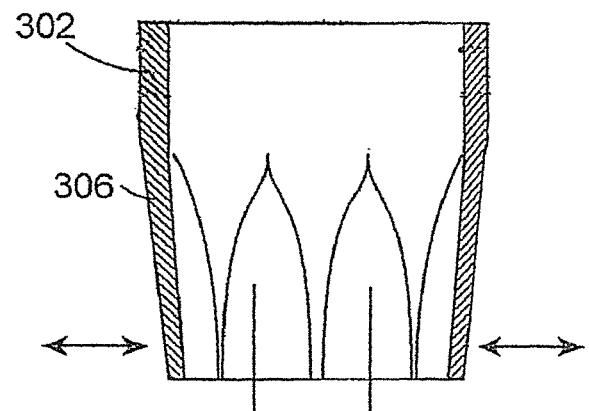
FIGS. 64 and 65 are side views of the device of FIG. 60 with the valve in the open configuration.
Figure 63:
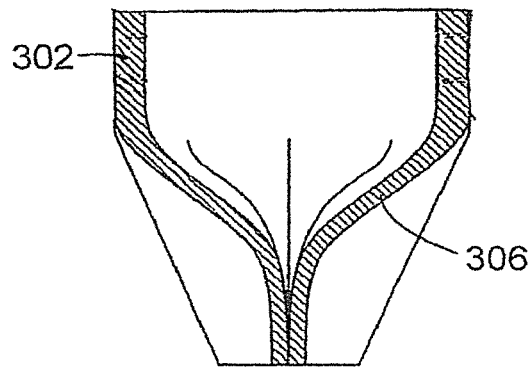
Figure 65:
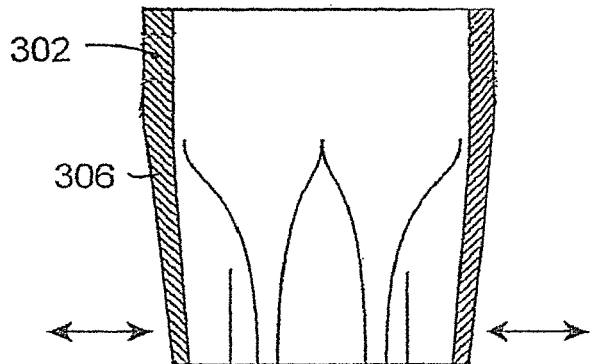

Referring to FIGS. 41 to 44 there is illustrated another valve device 151 according to the invention which is similar to that described above and like parts are assigned the same reference numerals. In this case the valve 1 is housed within a support structure or scaffold 102 and is placed into the lumen of a stent 140 as illustrated in FIGS. 45 to 47. The support structure may comprise a relatively short length (typically 40 mm) of a mesh made from a shape memory material such as Nitinol. The mesh may be formed by laser cutting and/or may be of woven construction. Deployment into the lumen of the host stent 140 is via self expansion from a radially collapsed state within a delivery catheter 130 as shown in FIGS. 43 and 44. The device 151 is held in place within the stent 140 by means of specific interaction mechanisms that increase the axial friction of the support structure 102. FIGS. 45 to 47 illustrate the interaction with the host stent 140. In this embodiment the support structure 102 has a series of loops or protrusions 155 extending perpendicularly from its surface. These protrusions 155 engage with the structure of any host stent 140 by interlocking with the existing mesh as shown in FIGS. 52 and 53. The apical tip of each protrusion 155 is in this case rounded or designed so as to be non-traumatic to any tissue that may come into contact with the protrusion 155. The intrinsic radial force of the support structure 102 as well as the flexural strength of the protrusions 155 interact to effect the retention performance of the support structure 102. Thus the stiffness or flexural strength of the protrusion 155 and the radial force of the support structure 102 may be modified to change the interlocking capability and retention performance of the device.

The valve device 151 is also readily radially collapsible by distal and proximal drawstrings 170, 171. The distal drawstring 170 passes through eyelets 172 mounted to the support structure 102 at the distal end of the valve device 151. The distal drawstring 170 has an accessible pull string 173 which, on pulling, pulls the drawstring 171 inwardly and thus reduces the diameter of the distal end of the support structure 102. Similarly the proximal drawstring 171 passes through eyelets 175 mounted the support structure 102 at the proximal end of valve device 151. The proximal drawstring 171 has an accessible pull string 177 which, on pulling, pulls the drawstring 171 inwardly and thus reduces the diameter of the proximal end of the support structure 102. The pull strings 173, 177 can be readily gripped using a suitable instrument such as a grasper to draw the proximal and distal ends of the support structure 102 inwardly for ease of removal of the valve device 151.

Referring to FIGS. 48 to 57 there is illustrated another valve device 200 according to the invention which is similar to that described above and like parts are assigned the same reference numerals. In this case the valve 1 is housed within a support structure or scaffold 102 and is placed into the lumen of a stent 140 as illustrated in FIGS. 53 to 56. The support structure 102 may comprise a relatively short length (typically 40 mm) of a mesh made from a shape memory material such as Nitinol. The mesh may be formed by laser cutting and/or may be of woven construction. Deployment into the lumen of the host stent 140 is via self expansion from a radially collapsed state within a delivery catheter 130 as shown in FIGS. 50 to 55. The device 200 is held in place within the stent 140 by means of specific interaction mechanisms that increase the axial friction of the support structure 102. FIG. 56 illustrates the interaction with the host stent 140. In this embodiment the support structure 102 has a series of loops or protrusions 155 extending perpendicularly from its surface. These protrusions 155 engage with the structure of any host stent 140 by interlocking with the existing mesh as shown in FIG. 56. The apical tip of each protrusion 155 is in this case rounded or designed so as to be non-traumatic to any tissue that may come into contact with the protrusion 155. The intrinsic radial force of the support structure 102 as well as the flexural strength of the protrusions 155 interact to effect the retention performance of the support structure 102. Thus the stiffness or flexural strength of the protrusion 155 and the radial force of the support structure 102 may be modified to change the interlocking capability and retention performance of the device.

The valve device 200 is also readily radially collapsible by distal and proximal drawstrings 170, 171. The distal drawstring 170 passes through eyelets 172 mounted to the support structure 102 at the distal end of the valve device 200. The distal drawstring 170 has an accessible pull string 173 which, on pulling, pulls the drawstring 171 inwardly and thus reduces the diameter of the distal end of the support structure 102. Similarly the proximal drawstring 171 passes through eyelets 175 mounted the support structure 102 at the proximal end of valve device 200. The proximal drawstring 171 has an accessible pull string 177 which, on pulling, pulls the drawstring 171 inwardly and thus reduces the diameter of the proximal end of the support structure 102. The pull strings 173, 177 can be readily gripped using a suitable instrument such as a grasper to draw the proximal and distal ends of the support structure 102 inwardly for ease of removal of the valve device 200.

It will be noted that in the case of this device 200 the diameter of the support scaffold is relatively uniform and the proximal and distal ends 201, 202 of the device 200 are not tapered. We have found that the interengagement of the rounded protrusions 155 in interstices defined in the mesh structure of the stent 140 is sufficient to retain the device 200 in position in the stent 140. Typically, the diameter of the expanded support structure 102 will be slightly larger, for example 1 to 5% larger than that of the host stent 140 at the desired deployment location to assist in maintaining the scaffold 102 in situ.

In some cases, as illustrated in FIG. 57 the devices of the invention such as the device 200 may be a radially collapsed state if it is described to re-position the valve device 200 with the stent 140 or to withdraw the device 200, for example for replacement and/or for replacement of the host stent 140.

Thus, the collapsibility of the valves enables its optional removal by disengagement of the protrusions 155 from the host stent 140, thus eliminating any axial friction associated with the host stent 140.

Figure 1:
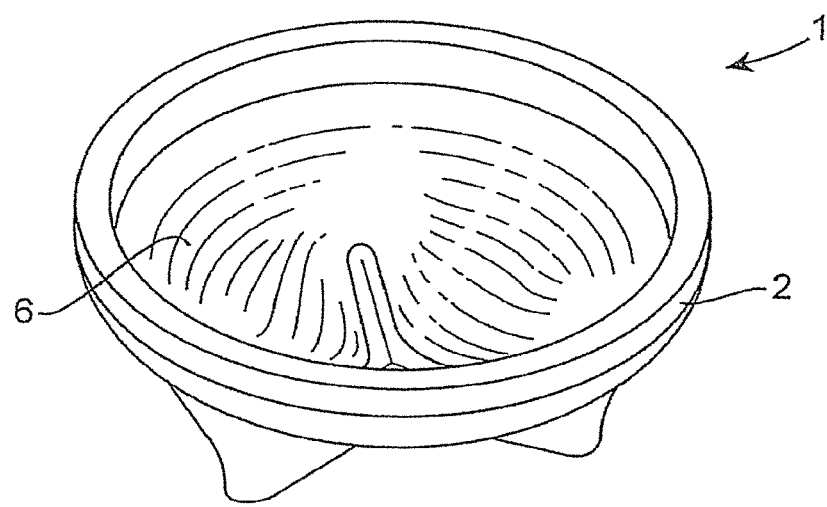
FIG. 1 is an isometric view (from above) of a valve according to the invention.
Figure 9:
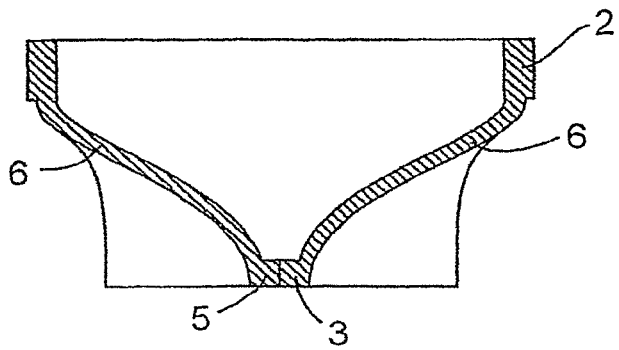
FIGS. 9 and 10 are cross sectional views of the valve.
Figure 10:
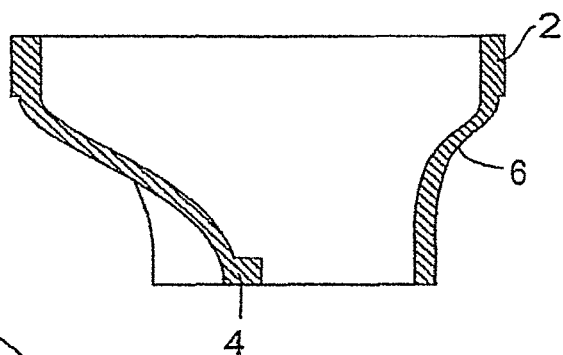
Figure 7:
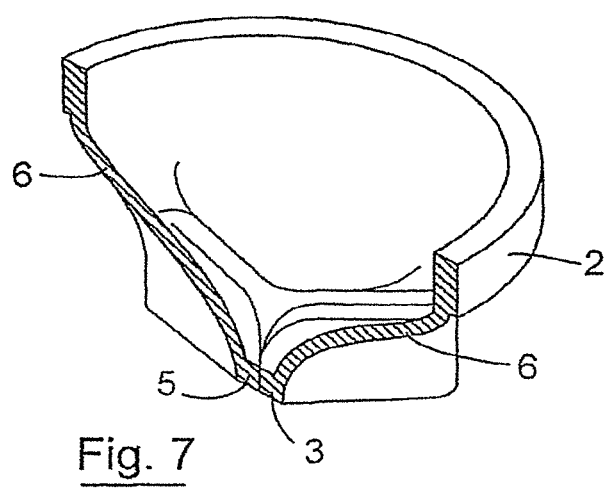
FIGS. 7 and 8 are isometric, partially cut-away sectional, views of the valve.
Figure 8:
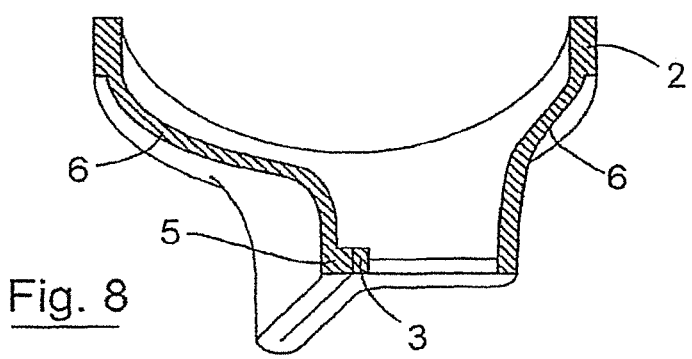

The valve of FIGS. 1 to 57 may be relatively short and is typically less than 30 mm, less than 25 mm, less than 20 mm, less than 15 mm and is typically about 10.6 mm long with an outer rim diameter of 18 mm or about 11 mm long for an outer rim diameter of 20 mm.

The valve may have any desired number of leaflets, for example the valve 300 illustrated in FIGS. 58 to 65 has six valve leaflets 333. These leaflets 333 are oriented perpendicular to direction of food flow to additionally allow greater distensibility of the valve aperture.

Referring to FIGS. 58 to 65 there is illustrated another valve device according to the invention. The device 300 comprises a valve 301 which can open automatically in one direction.

The valve 300 comprises a polymeric valve body having a proximal outer support region with a rim 302, six valve leaflets 303, and a main body region 306 extending between the support rim 302 and the valve leaflets 303. The valve leaflets 303 extend inwardly and distally and terminate at distal end faces 303 respectively. The leaflets each 303 have legs which extend at an included angle of 60° to each other. The adjacent pairs of legs co-apt to close the gap between the valve leaflets 303 when the valve is in the normally closed configuration.

The valve 300 has two configurations. The first configuration is a normally closed configuration in which the valve leaflets 303 co-apt to close the valve. The second configuration is an open configuration in which the valve leaflets 303 are opened such that the leaflet leg pairs are opened and spaced-apart in response to a force F1 to allow flow through the valve 300.

The various configurations of the valve 1 are illustrated in FIGS. 58 to 65. In the first or normally closed configuration the valve leaflets 303 co-apt. When a force F1 is applied to the valve leaflets 303 the leaflet legs pairs open to allow flow to pass. When the force F1 is removed the leaflets 303 return to the closed position under the inherent biasing of the polymeric material of the valve body.

The valve leaflets 303 are reinforced in the region of co-aption. In this case, this is achieved by a local thickening of the polymeric material in this region. Similarly the support rim 302 is reinforced by a local thickening of the polymeric material.

The region of co-aption of the valve leaflets 303 has an axial extent which is typically from 1 to 5 mm. This ensures positive co-aption of the leaflets across a significant interfacial area when the valve is in the normally closed configuration. The thickness of the leaflets at the region of co-aption is typically between 0.1 mm and 10 mm.

The valve body 306 has a generally concave outer face and a generally convex inner face.

The valve 300 of the invention returns to its original working position after being fully opened. This is accomplished without damaging the working valve.

An important characteristic influencing the functioning of the valve 300 is the leaflet legs that impinge on one another. By varying the geometry and length of the leaflets 303 the valve 300 can be made to open at different pressures. Opening is also dependant on the elasticity and density of the material the device is made from. Additionally, the overall diameter and the diameter to which the leaflets open influence the opening force.

The valve may be of any suitable biocompatible polymeric material. It may be of a biocompatible polymeric material having properties which allow the valve to function as described.

The materials used for the production of this valve have a % elongation between 50% and 3000%. The material also has a tensile strength of between 0.01 and 5 MPa. Additionally the material could have an antimicrobial action to prevent colonisation when in-vivo. Additionally the material can be elastic or viscoelastic and can optionally be an open cell foam. The density of the material should be between 0.1 g/cm3 to 1.5 g/cm3.

The valve 300 of the invention may be mounted to any suitable luminal prosthesis. The rim 302 of the valve provides a mounting ring for mounting within the prosthesis, for example, the valve 300 may be mounted to the stent by suturing the rim 2 to the stent mesh using sutures.

Many emerging obesity treatments involve the placement of a tube into the duodenum, which restricts the absorption of certain nutrients at this point in the body. The resulting calorific deficit then results in weight loss. Some of these devices can cause the pyloric valve to be opened for prolonged periods thus causing rapid stomach emptying. During episodes of rapid stomach emptying the feeling of fullness is shortened and thus the patient eats more.

We have found that by placing a valve device at or near the pylorus that can controllably restrict the rate of stomach emptying then a feeling of fullness or satiety can be gained.

Referring to FIGS. 66 and 67 there is illustrated a valve device 500 that can be retrospectively placed into an existing obesity treatment device such as a sleeve 501 which extends from a stomach 502 into the duodenum 503. One such sleeve device is described in US2005/0125075A, the entire contents of which are incorporated herein by reference. The valve 500 functions to restrict the rate of stomach emptying. The positioning of the valve 500 within a pre-positioned sleeve 501 is illustrated in FIGS. 66 and 67. The valve 500 may be of the type described above and may be attached to a scaffold 505 as described above.

Figure 69:
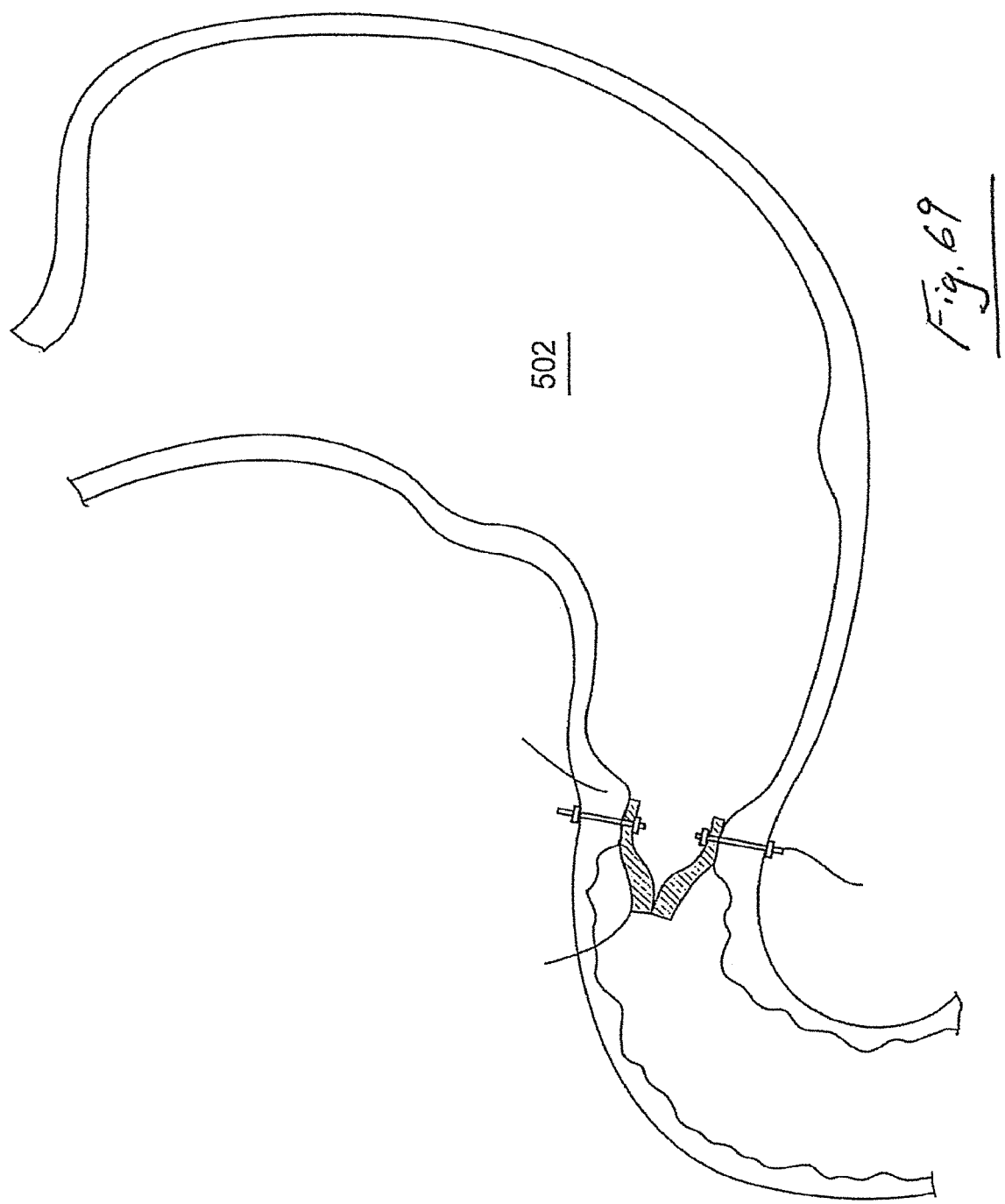

Referring to FIGS. 68 and 69 there is illustrated a valve 550 of the invention which in this case is placed in a pyloric sphincter 551 in order to control the rate of stomach emptying and thereby provide an enhanced feeling of satiety. This approach may be used, if example in association with gastric banding or other obesity treatment system. The valve 550 may be retained in situ by any suitable means such as anchors 552.

Figure 70:
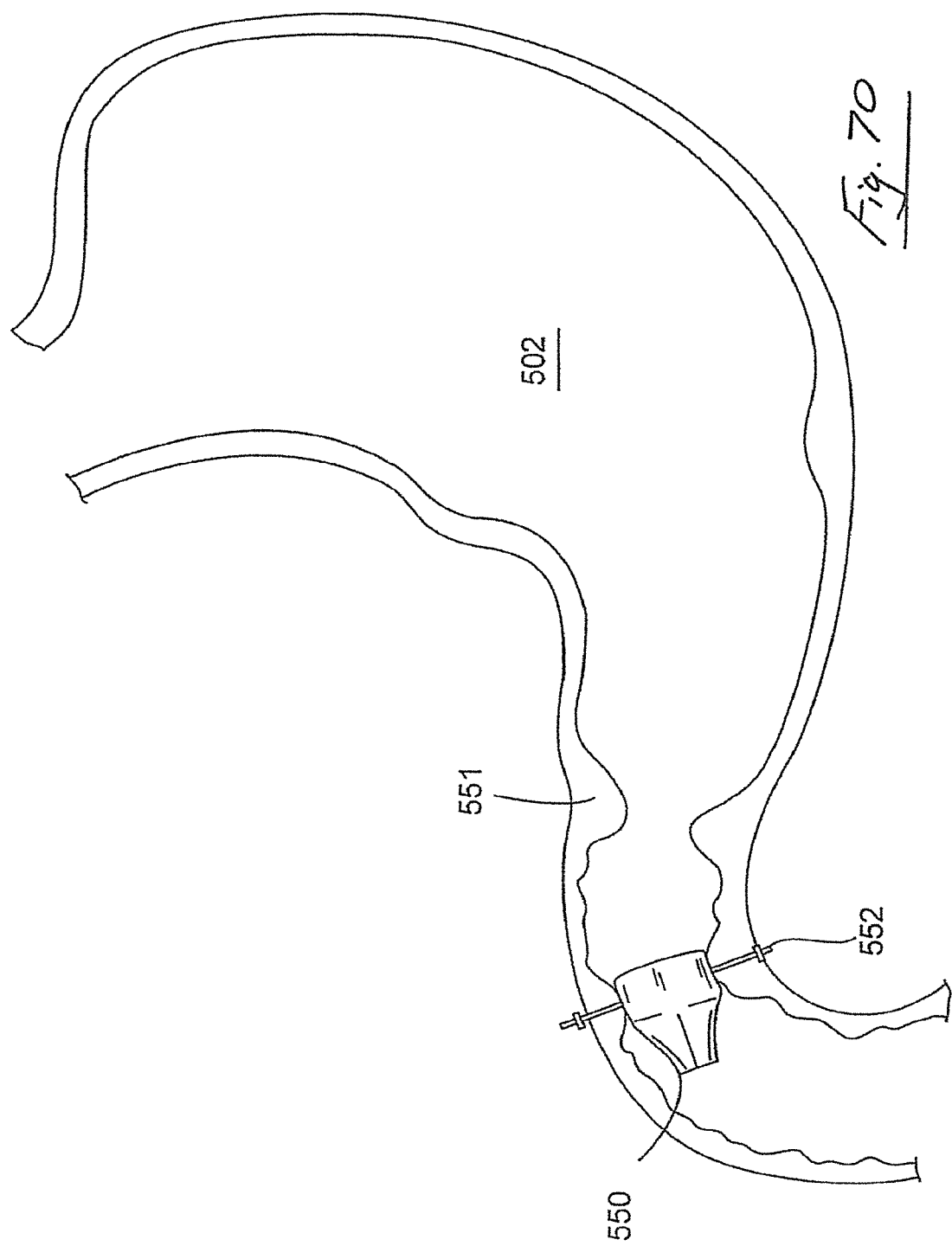

Alternatively, as illustrated in FIGS. 70 and 71 the valve 550 may be located distal of the pyloric sphincter 551 to provide a further valve acting in series with the pyloric valve or sphincter.

Referring to FIGS. 72 to 77 there is illustrated a gastrointestinal implant device 600 which comprises a sleeve 601 for extending into the duodenum and an artificial valve 602 for placement at the pylorus 603 to control flow from the stomach 604 into the duodenum which is lined by duodenal sleeve 601. The device 601 also comprises a support structure for the valve. In this case the support structure comprises a scaffold 605 to which the valve 602 is mounted. The support structure also comprises a luminal prosthesis 606 to which the scaffold is mounted. In this instance, the scaffold 605 is releasably mountable to the luminal prosthesis 606. The sleeve 601 is mounted to the support structure and in this case to the valve and/or the scaffold 605.

In this case the support structure comprises a stent-like scaffold 605 and the luminal prosthesis 606. The prosthesis 606 is for deployment at the pylorus and the scaffold 605 to which the valve 602 is mounted is releasably mountable to the pre-deployed luminal prosthesis 606. The scaffold comprises engagement elements which are releasably engagable with the luminal prosthesis 606. The engagement elements may comprise protrusions 607 which are releasably engagable with the luminal prosthesis. The luminal prosthesis 606 in this case comprises a mesh which may have a coating thereon. The protrusions 609 may engage with and in some cases penetrate the mesh. In the case of a coating on the mesh the protrusions 607 may penetrate the coating.

In this embodiment at least a part of the implant device is removable for complete removal, re-positioning, or replacement. There is a release means for releasing the scaffold 605 from engagement with the prosthesis 606. The release means in this case comprises means for reducing the diameter of at least portion of the scaffold. The release means may comprise a drawstring 611 extending around the scaffold 605. In this case there is a first drawstring 611a extending around a proximal end of the support structure and a second drawstring 611b extending around a distal end of the support structure. For removal, the drawstrings are tightened by pulling on the loops 612 using a suitable instrument such as a grasper.

Both the prosthesis 606 and the scaffold 605 may be of a shape memory material such as Nitinol and have a reduced diameter delivery configuration and an expanded deployed configuration.

The prosthesis 606 in this case comprises a proximal flare 620 for location, in the expanded configuration at the antrum of the pylorus. The flare 620 assists in anchoring the prosthesis in position. The prosthesis 606 in this case also has a distal bulbous region 621 which assists in anchoring the prosthesis in position. The prosthesis 606 has a scaffold receiving region 622 which in this case is intermediate the proximal and distal ends of the prosthesis 606.

The scaffold 605 has a proximal region 630 to accommodate the valve 602 and a distal region 631 to accommodate the sleeve 601 in a retracted delivery configuration. The valve 602 may be attached to the scaffold 605 by sutures 632 and/or may be bonded, for example by adhesive bonding to the scaffold 605.

The sleeve 601 in this case is also attached to the scaffold 605 and/or to the valve 602, for example by bonding and/or sutures.

The valve 602 has a normally closed configuration and an open configuration in which the valve is opened for stomach emptying. The valve 602 is adapted to open automatically for stomach emptying and to return automatically to the closed configuration. The valve may be of a viscoelastic foam material such as the foam materials described in detail in this specification. The valve 602 is in this case similar to the valves described earlier and comprises an outer support region 640, at least three valve leaflets 641, and a main body region 642 extending between the support region and the valve leaflets 641. The valve 602 has a region 643 of co-aption of the valve leaflets in the closed configuration to maintain the valve in the normally closed configuration. The region 643 of co-aption may extend for an axial length of at least 1 mm.

Figure 74:
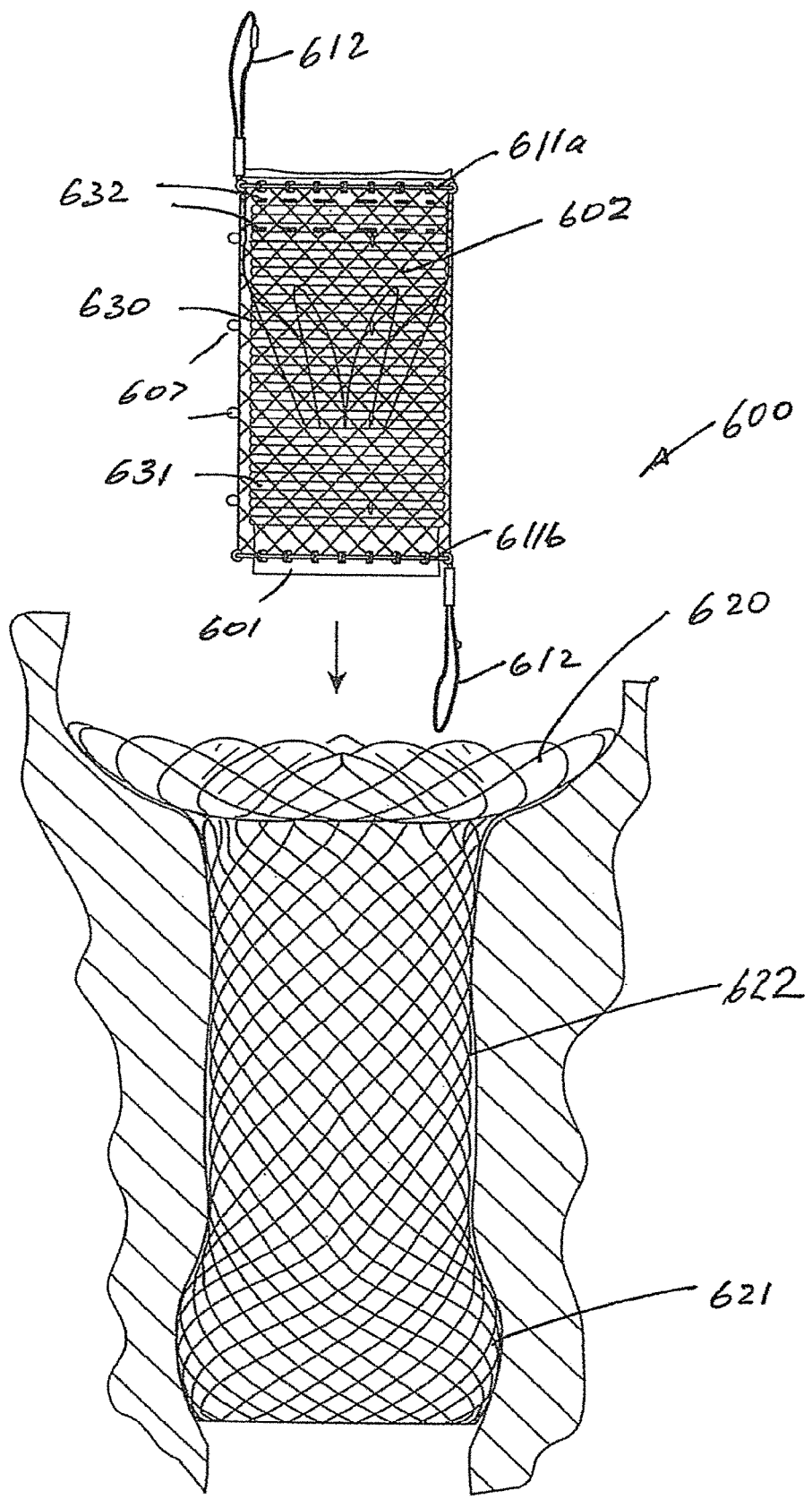
FIG. 74 is an elevational, partially cross sectional view of an implant device with a prosthesis located in a lumen such as the pylorus and a valve, sleeve and scaffold for mounting to the prosthesis.
Figure 75:
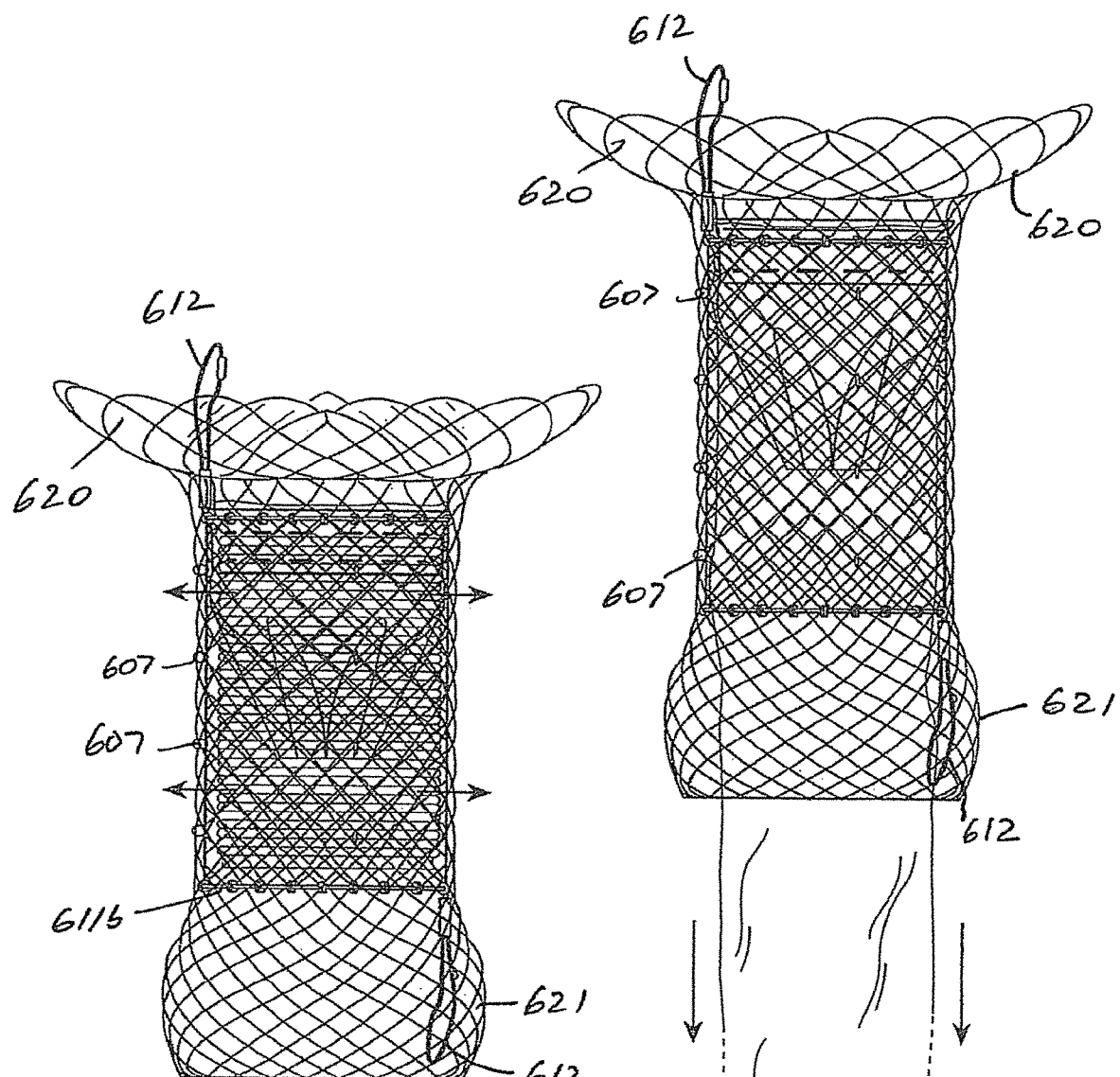
FIG. 75 is an elevational view of the device of FIG. 72 assembled.
Figure 76:
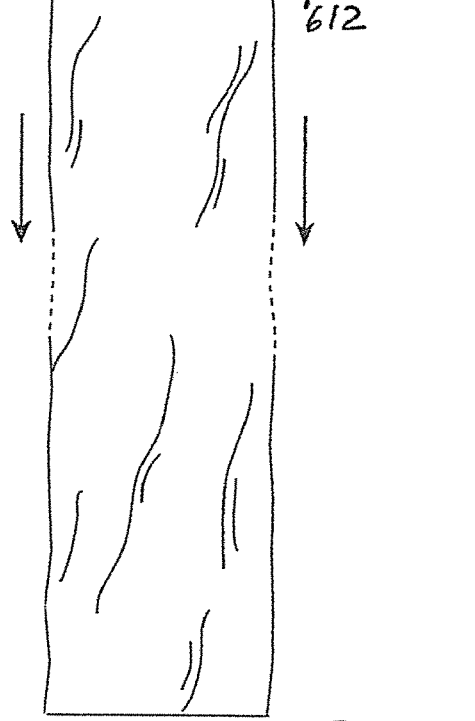
FIG. 76 is an elevational view of the device of FIG. 75 with the sleeve extended.
Figure 77:
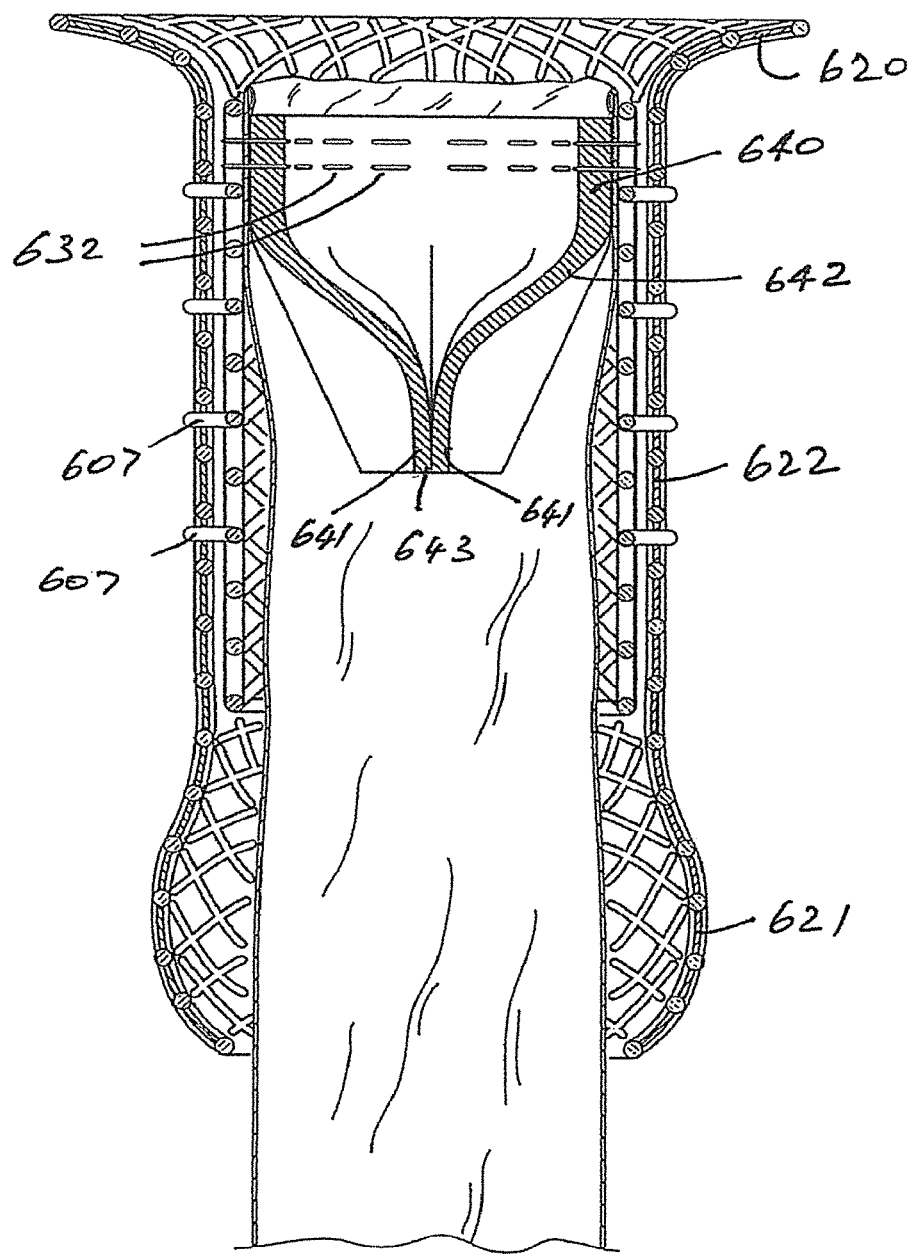
FIG. 77 is an elevational, partially cross sectional view of the device, in situ.

FIG. 72 shows the luminal prosthesis 606 in a relaxed, pre-loading configuration. FIG. 73 shows the scaffold 605, valve 602 and sleeve 601. The sleeve 601 is in a retracted configuration. FIG. 74 shows the prosthesis 606 deployed at the pylorus and the scaffold 605/valve 602/sleeve 601 being inserted into the prosthesis 606. FIG. 75 shows the scaffold 605/valve 602/sleeve 601 deployed in the prosthesis 606. FIG. 76 is a view similar to FIG. 75 with the sleeve 601 expanded into a deployed configuration extending through the duodenum. FIG. 77 is a cross sectional view showing the valve 602, support structure and sleeve 601 fully deployed.

Figure 78:
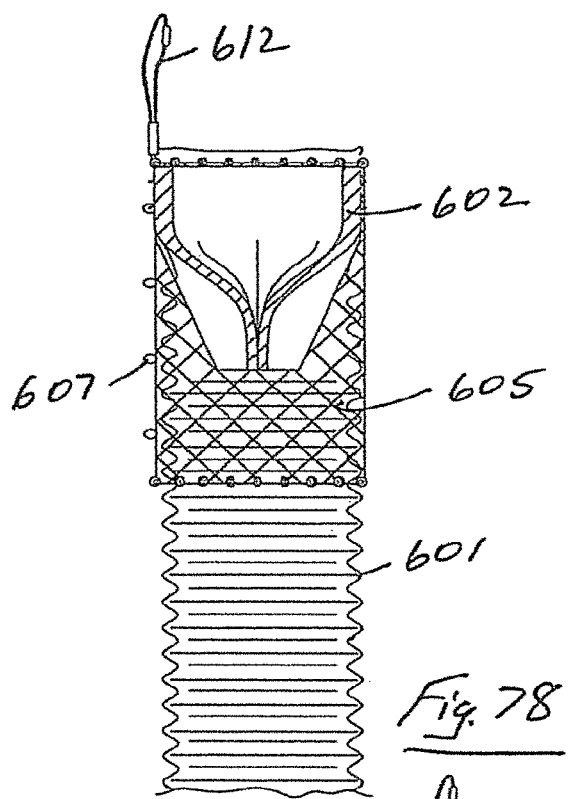
FIG. 78 is a view similar to FIG. 77 of an implant device with a sleeve in one folded delivery configuration.
Figure 79:
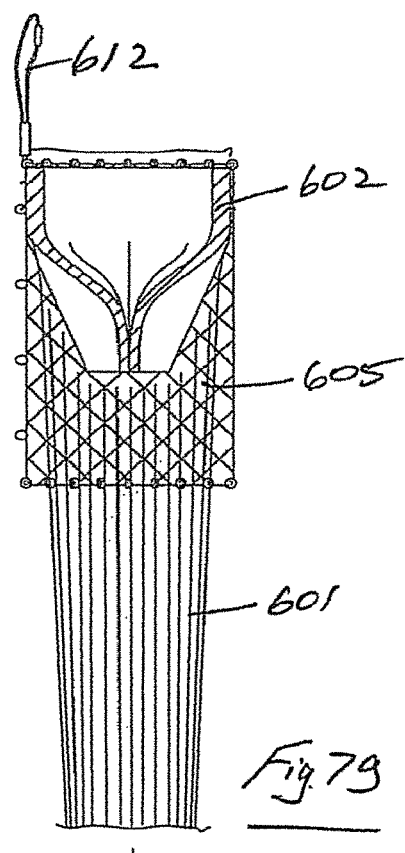
FIG. 79 is a view similar to FIG. 78 with the sleeve in another folded delivery configuration.
Figure 80:
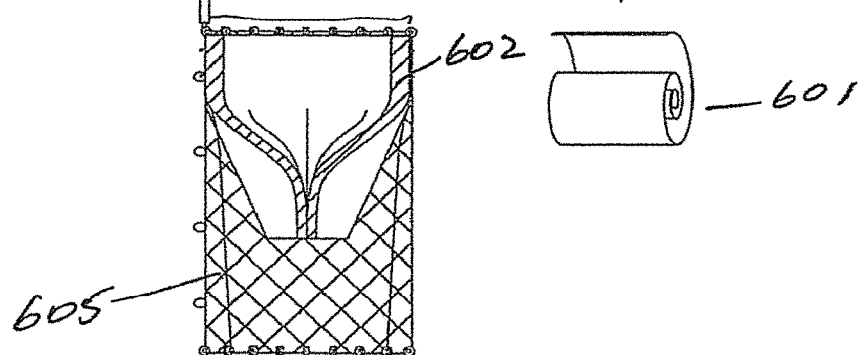
FIG. 80 is a view similar to FIG. 79 with the sleeve in a further folded delivery configuration.

It will be appreciated that the sleeve may be configured in different ways in a retracted delivery configuration. Some examples are shown in FIGS. 78 to 80. In FIG. 78 the sleeve 601 is folded somewhat like an accordion. In FIG. 79 the sleeve 601 may be folded longitudinally and may subsequently be spirally wound. In FIG. 80 the sleeve 601 has longitudinal pleats or folds and is also folded over transversely.

The sleeve 601 may be of constant diameter along the length thereof or may be tapered (FIGS. 81/83) or may have a narrowed proximal section and a constant diameter distal section (FIG. 82).

The sleeve 601 may have a retaining means to assist in retaining the sleeve at a desired location. For example, as illustrated in FIG. 81 the sleeve 601 may have a retaining ring 650 at or near the distal end of the sleeve. There may be a plurality of such retaining rings 650 which may be spaced-apart along the sleeve 601 as illustrated in FIG. 83. The rings 650 may be of different size and/or shape to suit the target anatomy. The retaining rings 650 may have a biasing means to bias them into an enlarged configuration. For example, the retaining ring 650 may be oversized with respect to the diameter of the sleeve 601. There may be a release means such as a drawstring or the like to release the retaining ring 650 from the expanded deployed configuration.

Figure 84:
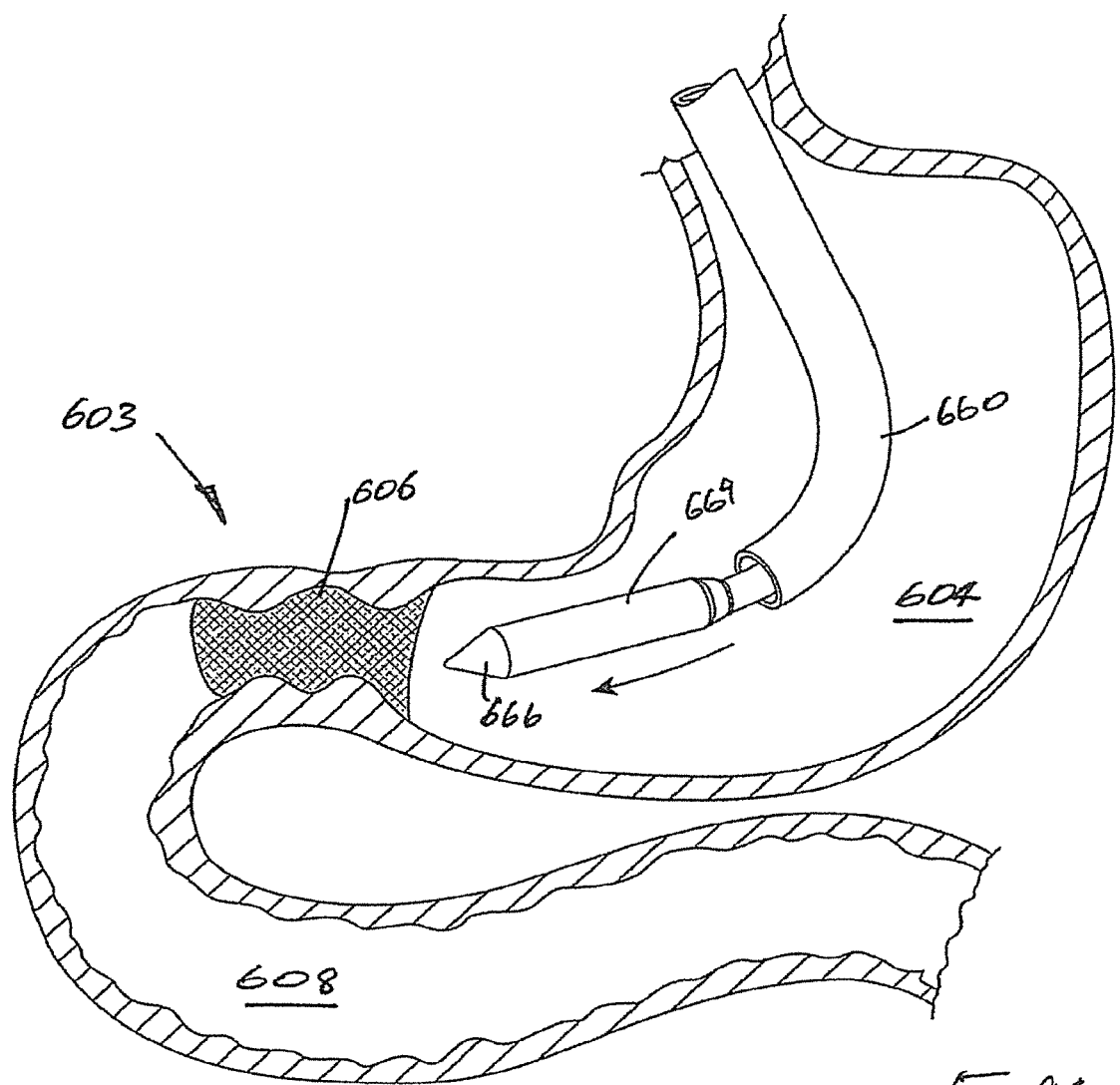
FIG. 84 is cross sectional view illustrating a first stage in the delivery of an implant device to the pylorus.
Figure 85:
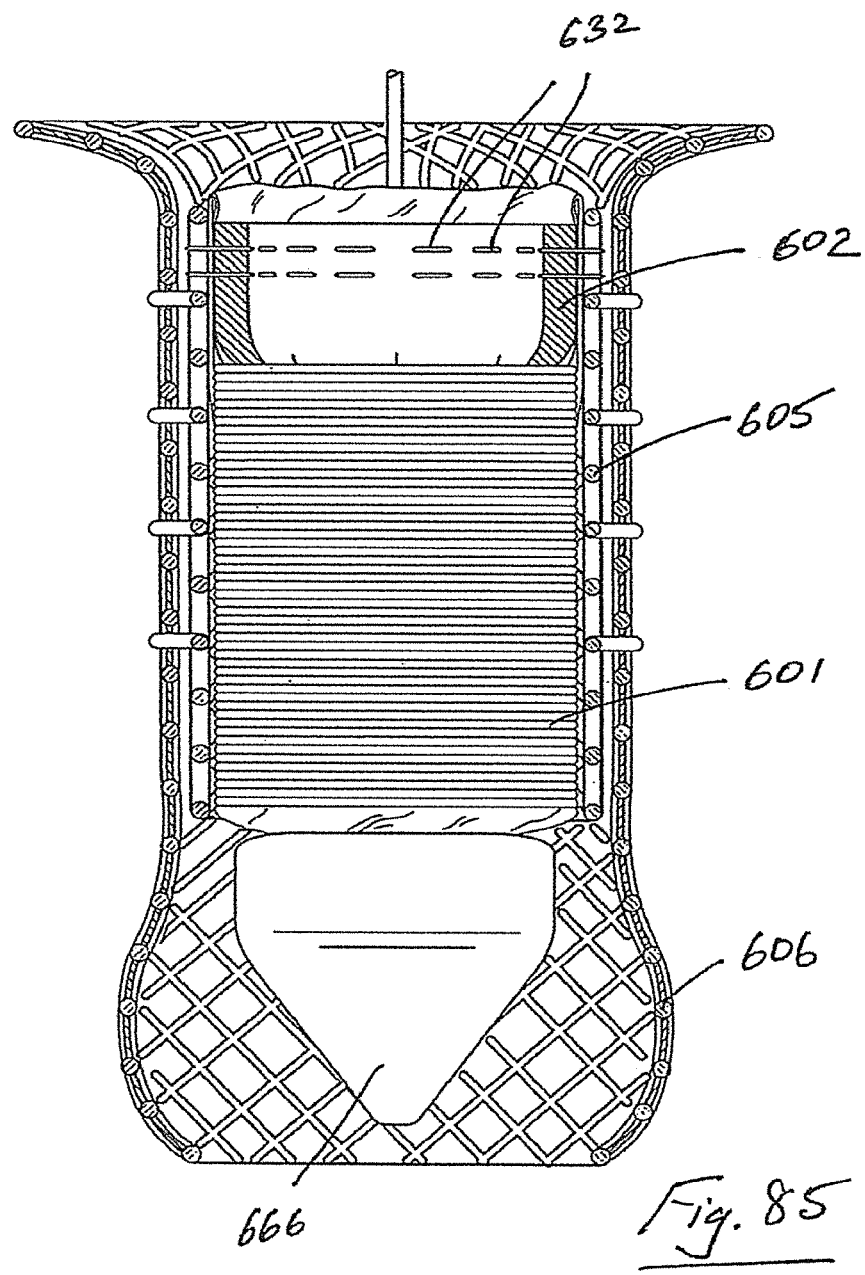
FIG. 85 is a cross sectional view of the implant device in position with the sleeve in a retracted configuration.

Referring to FIGS. 84 to 89 an implant device according to the invention and an associated delivery system are illustrated. The delivery system comprises a delivery catheter 660 with a distal capsule 669 which contains the scaffold 605, valve 602 and sleeve 601 in the retracted configuration. The delivery system includes a proximal expandable element provided by an inflatable proximal balloon 662 and a distal expandable element provided by a distal balloon 663. The proximal balloon 662 provides a temporary seal with the proximal end 664 of the sleeve 601 at the proximal side of the valve 602. The distal balloon 665 provides a temporary distal seal between a distal olive 666 and a distal end 667 of the sleeve 601. An inflation fluid is introduced into the sleeve 601 between the proximal and distal balloons 662, 665, the fluid causes the sleeve 601 to expand axially to the expanded deployed configuration. When the sleeve 601 is in the extended deployed configuration the distal balloon 665 is deflated, allowing the olive 666 to detach and travel distally. The rest of the delivery system can then be withdrawn proximally, leaving the implant device in situ. FIG. 84 illustrates the luminal prosthesis or stent 605 with a 30 mm wide proximal flare placed across the pylorus with the proximal flare resting against the pyloric antrum. An endoscope with a delivery system is advanced into the stomach. The delivery device is controlled through the shaft of the endoscope and comprises a capsule that is positioned proximal to the endoscope. The capsule is advanced to the pre-placed stent. FIG. 85 shows the stent, scaffold and valve with the sleeve in the retracted configuration. The distal olive 666 of the delivery system is also shown.

Figure 86:
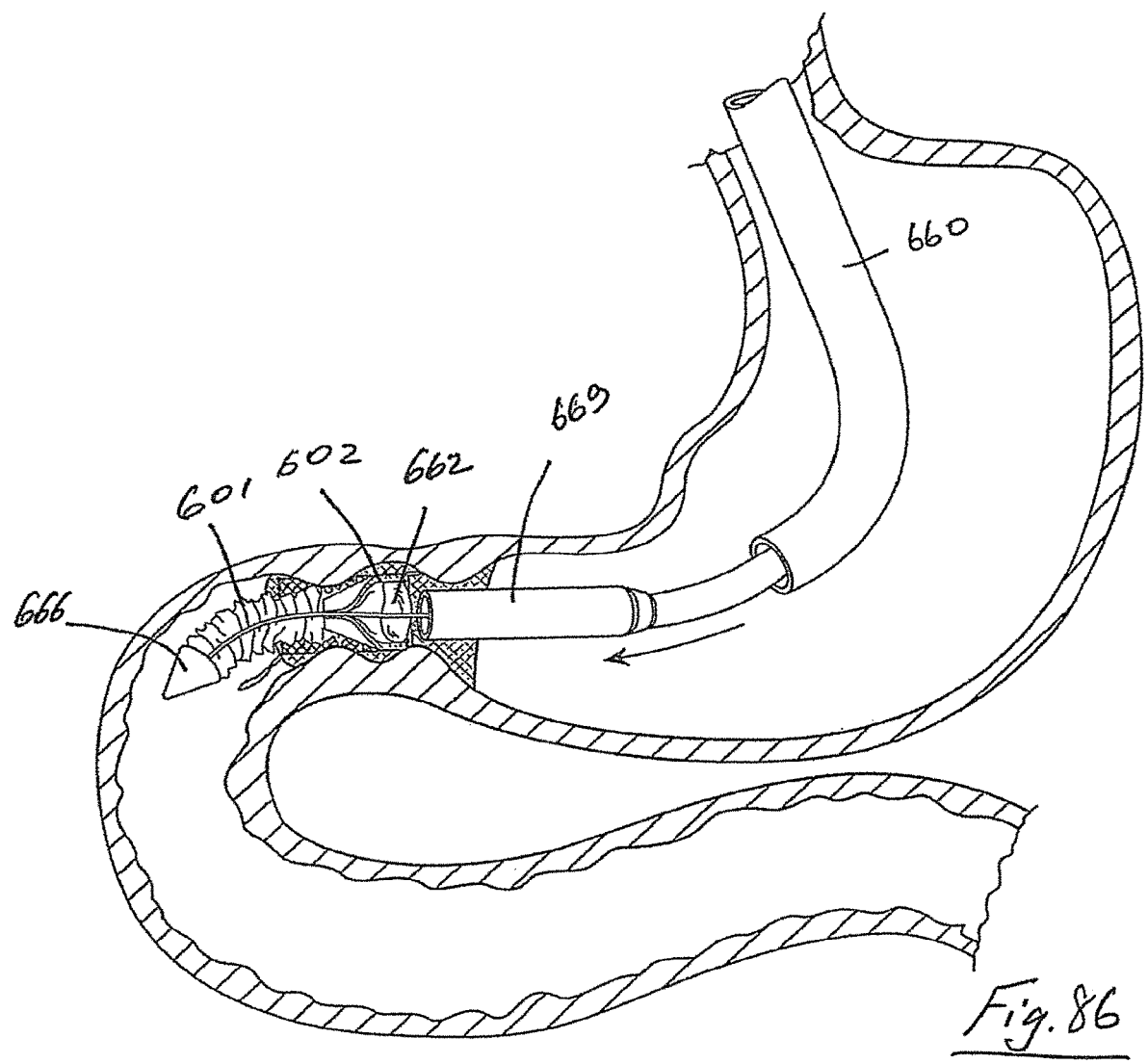
FIG. 86 is a cross sectional view of the implant device in situ, with the sleeve partially extended.

Referring to FIG. 86, water is flushed through the delivery system to elongate the plastic sleeve, which passes through the duodenum past the ligament of trietz.

Figure 87:
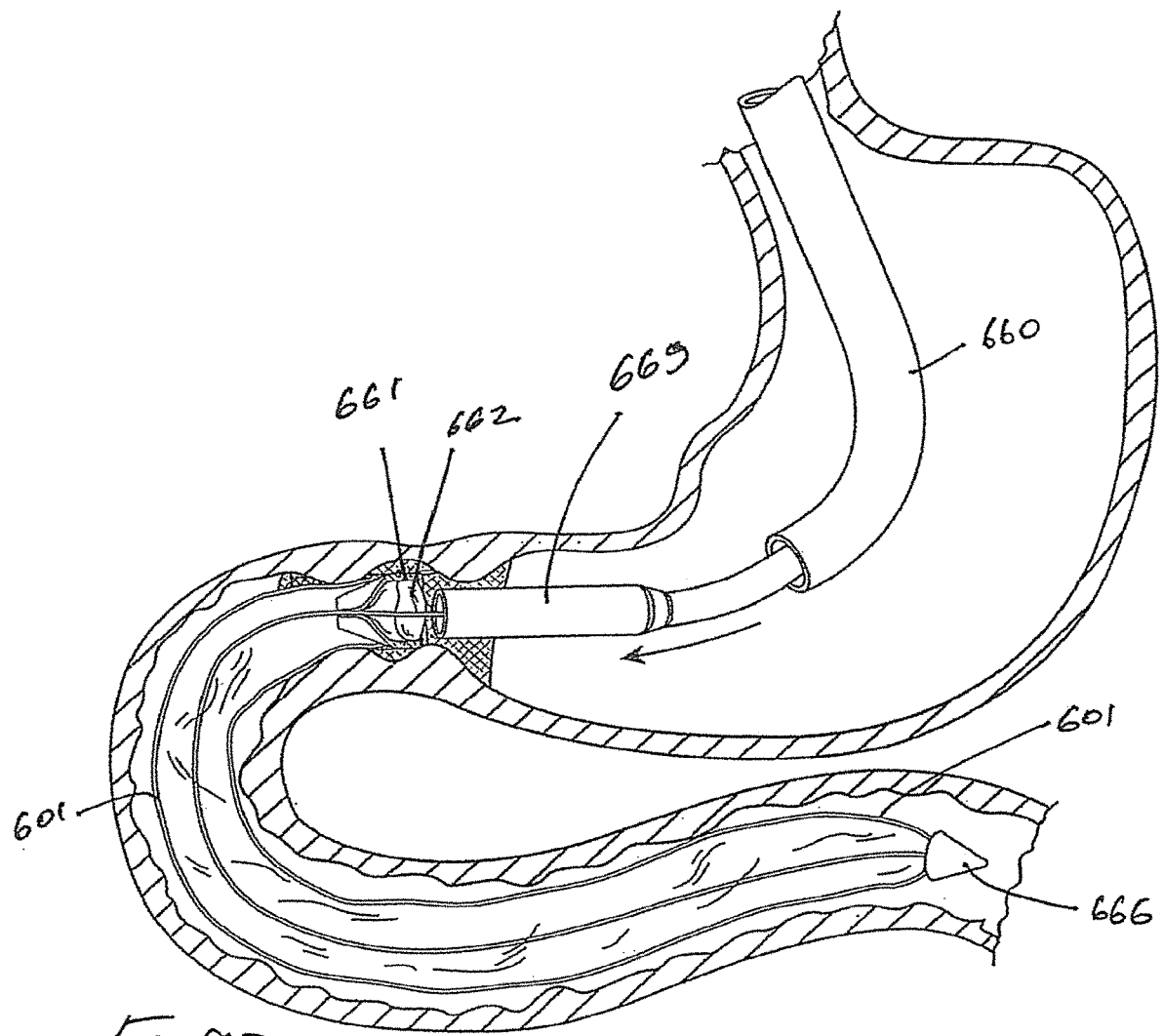
FIG. 87 is a cross sectional view similar to FIG. 86 with the sleeve further extended.

Referring to FIG. 87, when the implant device is deployed the delivery system is removed and the distal olive 666 passes through the intestine.

In the case of the delivery system of FIGS. 84 to 89 the valve and scaffold are deployed before the sleeve is deployed. In this arrangement the proximal seal is provided by the proximal balloon which seals against the valve as illustrated in FIG. 87.

Referring to FIGS. 90 to 97 there is illustrated another delivery system. In this case the valve and scaffold are deployed after deployment of the sleeve. In this arrangement the proximal seal is provided by the proximal balloon 662 which in this case seals against the inner wall of a distal capsule 669. The balloon 662 is not fully inflated in FIGS. 91, 92 and 94. A delivery catheter comprises an outer shaft 680 with a retraction hub 681 and an inner shaft 682. The shaft has various lumens and at the proximal end there are various ports connected with the lumens. There is a proximal sleeve inflation port 683, a distal tip balloon inflation port 684, a proximal seal or plunger balloon inflation port 685. There is also a guidewire port 686 (which is illustrated in FIG. 96) for a guidewire 687. FIG. 97 shows the various lumens,—a water injection lumen 690 for deployment of the sleeve,—a proximal balloon inflation lumen 691, a distal tip balloon inflation lumen 692 and a guidewire lumen 693. A flexible tube 688 extends through a lumen 689 in the inner shaft 682. The flexible tube 688 also extends through the proximal balloon 662 which in this case is of doughnut shape. The tube 688 has an outlet for inflation of balloon 665.

Figure 90:
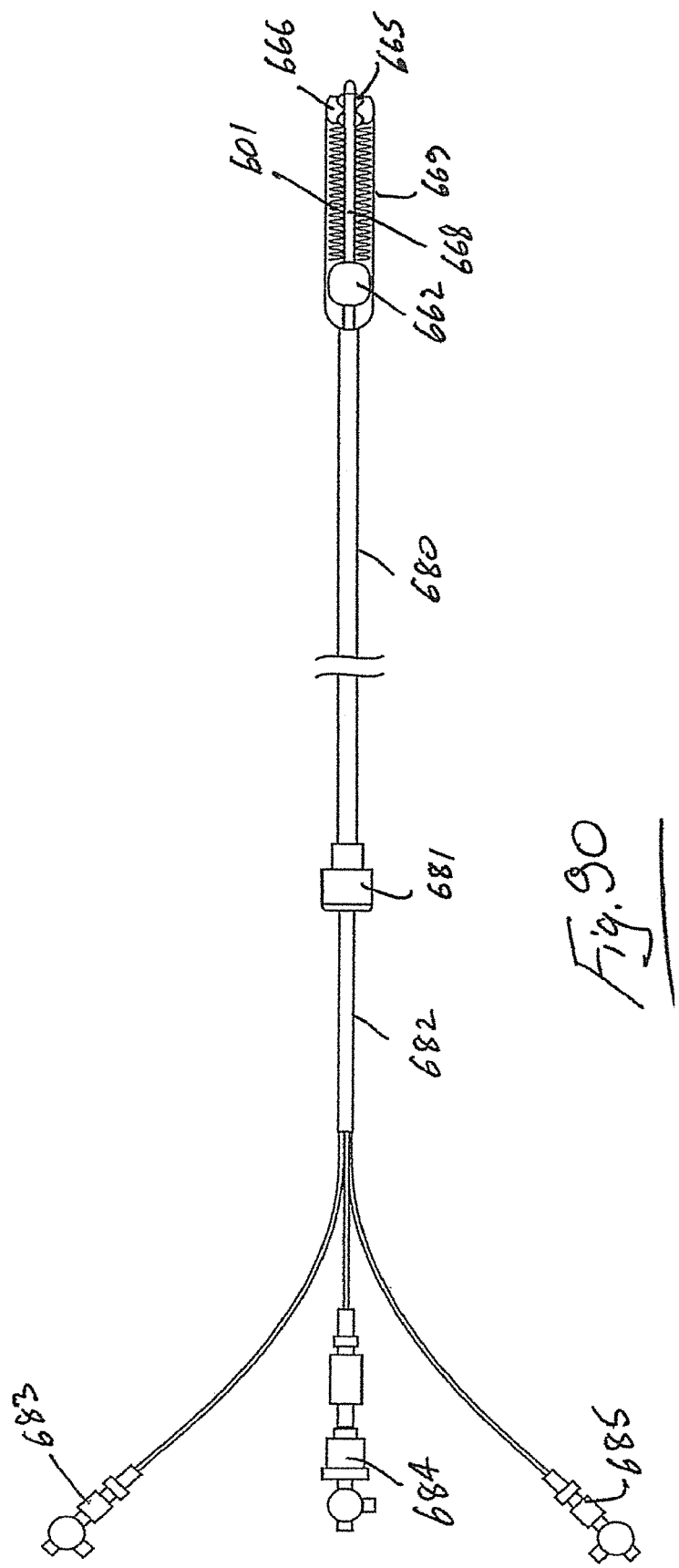
FIG. 90 is an elevational view of a delivery catheter for the implant device.
Figure 91:
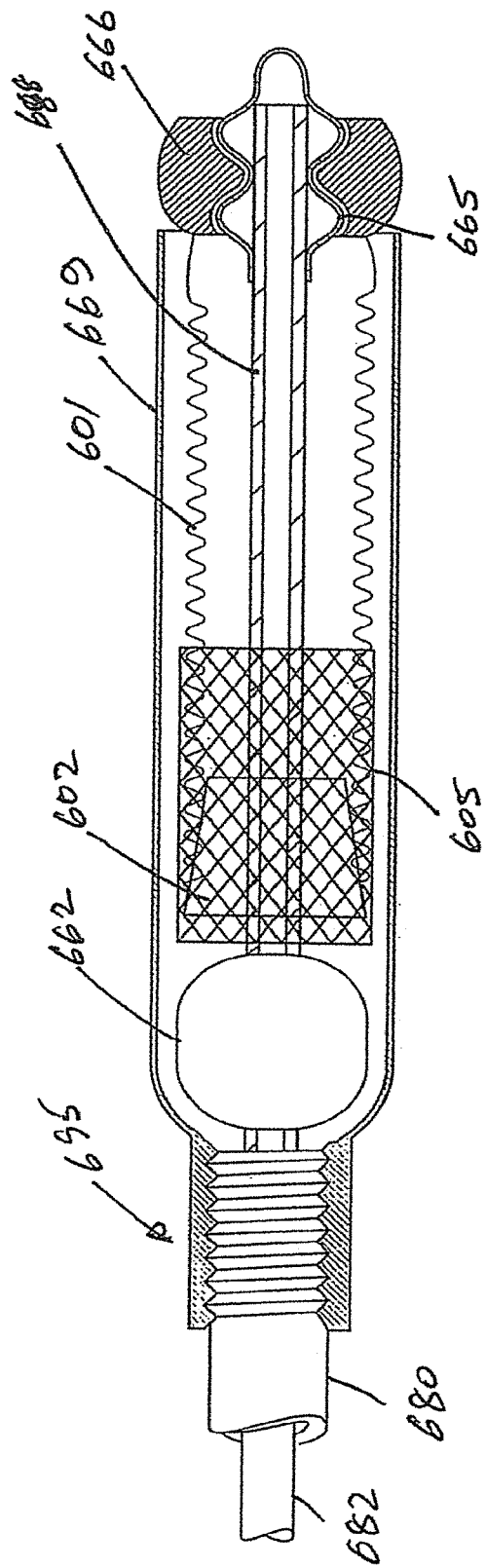
FIG. 91 is a cross sectional view of the delivery catheter of FIG. 90 with a capsule containing the implant device.

Referring to FIG. 90 the capsule 669 is mechanically releasable from the outer sheath, for example through a screw thread connection 695. In use, the shaft of the delivery system is inserted through the proximal end of a delivery channel of an endoscope. When the distal end of the shaft of the delivery shaft exits the distal end of the endoscope delivery channel the capsule is mounted to the distal end of the delivery shaft using the mechanical attachment which in this case is a screw-in attachment.

In FIG. 90 the sleeve/valve/scaffold implant device is in the retracted delivery configuration. The flexible tube 688 extends to the tip balloon 665 and has a hole through which air is delivered for inflation of the balloon 665. The tube 688 is of a suitable flexible material such as a plastics, for example nylon.

Referring to FIG. 92, the proximal balloon 662 is inflated to seal the sleeve 601 at the proximal end and the distal balloon 665 is inflated to seal the sleeve 601 at the distal end. Water is then flushed into the retracted sleeve 601 and by virtue of the seals 662, 665 at the proximal and distal ends, the water fills the sleeve 601, causing it to extend. The sleeve 601 is shown in a partially extended configuration in FIG. 92.

When the sleeve 601 has fully extended (FIG. 93) the distal balloon 665 is deflated, allowing the tip 666 to float into the intestine for discharge. The proximal balloon 662 remains inflated and acts as a plunger to deploy the scaffold from the capsule 669. The scaffold 605 engages with the stent 606 as described above and the delivery system is withdrawn as illustrated in FIG. 94.

Figure 95:
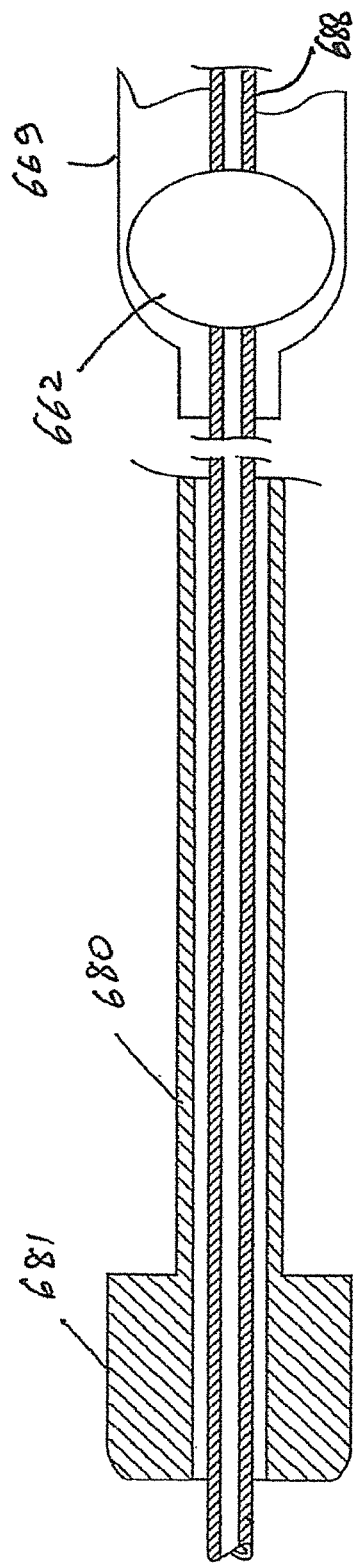
FIG. 95 is a cross sectional view of a proximal end of the delivery system capsule.

FIG. 95 illustrates the proximal delivery components. The retraction hub 681 is connected to the outer shaft to enable withdrawal of the outer shaft 680 over the inner shaft 682.

Figure 98:
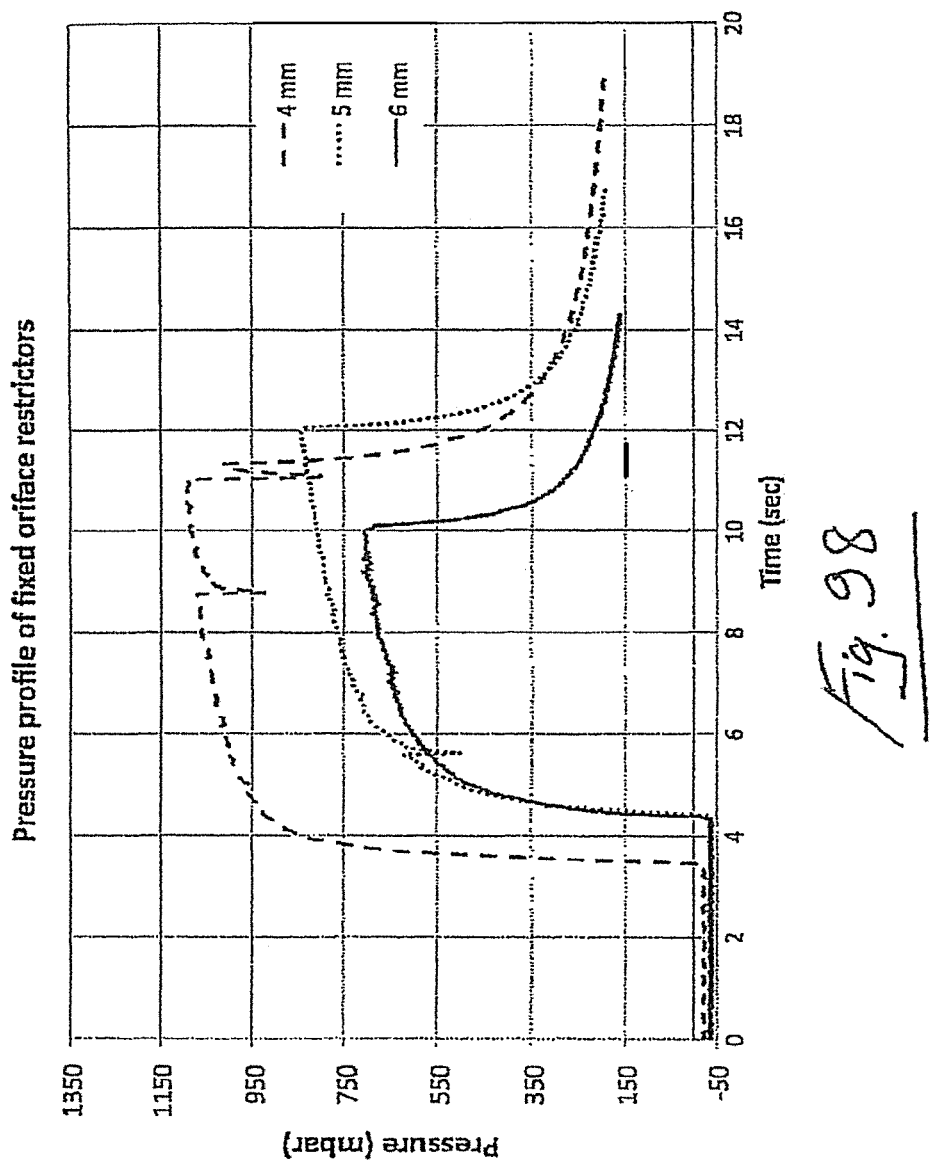
FIG. 98 is a graph of pressure profile over time with various fixed orifice restrictors.

FIG. 98 is a graph of the pressure profile of fixed orifice restrictors with various size orifices. The restrictions were created using a 1 mm thick polyethylene membrane. Each orifice was created by drilling out the desired hole size followed by verification using a Vernier calliper. The flowrate through the test fixture was controlled at 7.86 g/sec with a fluid having a viscosity of 39,000 Cps. It will be noted that when a series of fixed diameter orifice restrictors are used to impede fluid flow, the resulting back-pressures generated have a distinctive pattern. The back-pressure initially rises sharply followed by a sustained gradual pressure rise until flow is stopped. This behaviour is illustrated by FIG. 98 for 4 mm, 5 mm and 6 mm diameter restrictions. This is undesirable for use as a flow restrictor in the stomach because a constant rise in pressure as a function of flow might give rise to gastric distress and cramping.

Figure 99:
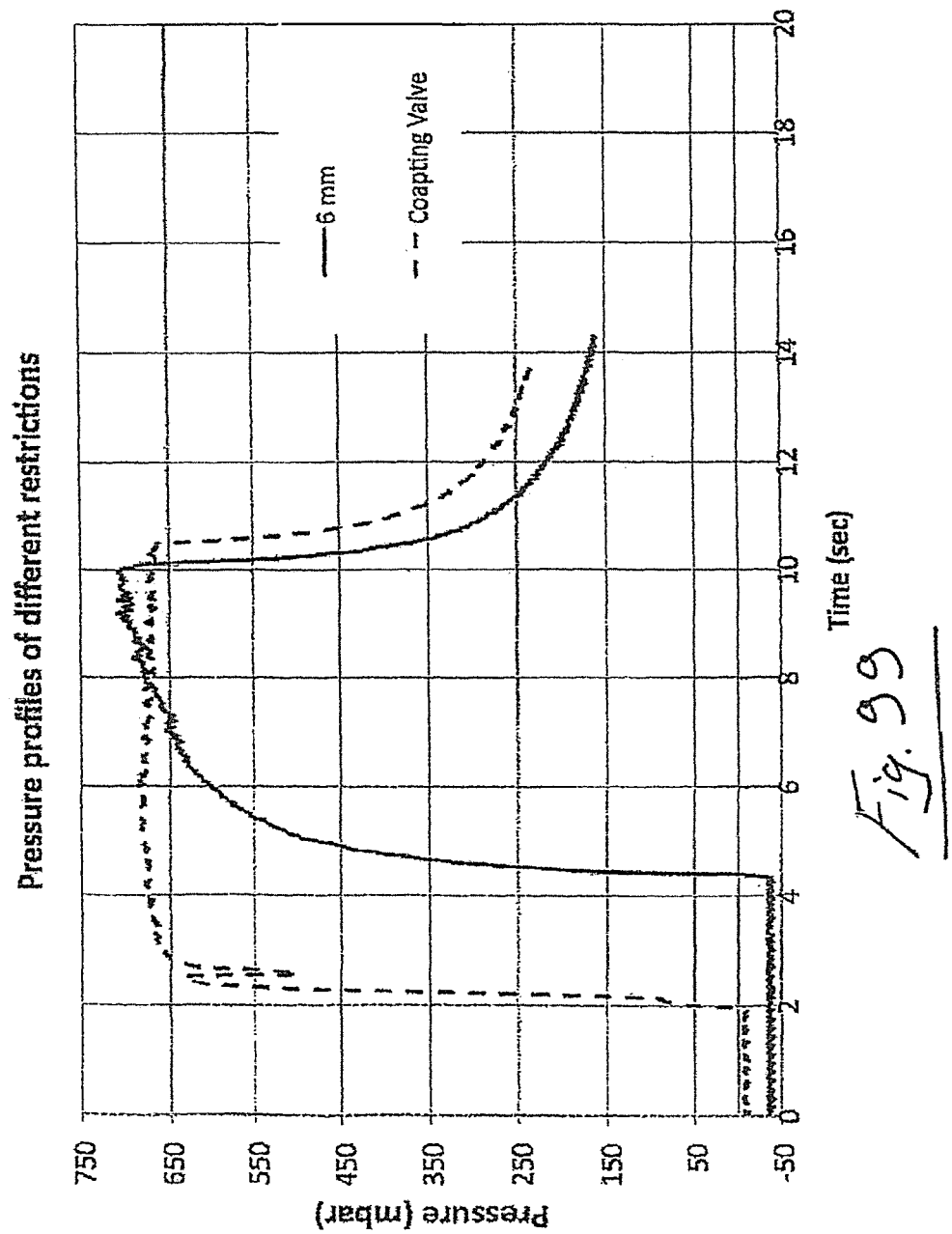
FIG. 99 is a graph of pressure profile over time with a fixed orifice restriction and an implant device comprising a valve of the invention.

FIG. 99 is a pressure profile of various different restrictions. The 6 mm orifice is made as described above for FIG. 98. The pressure profile represented by interrupted lines is generated using a leaflet valve as described above with reference to FIGS. 58-65. The valve is of a viscoelastic foam material. The foam material is in this case a material described in Example 5 of the Group 1 materials described below. The density of the material was 0.9 g/ml. It can be seen from FIG. 99 that a coapting valve of the above description enables the generation of a constant back-pressure over the duration of fluid flow. The valve is thus adapting to fluid flow to maintain a constant restrictive force independent of fluid flow therethrough.

Figure 100:
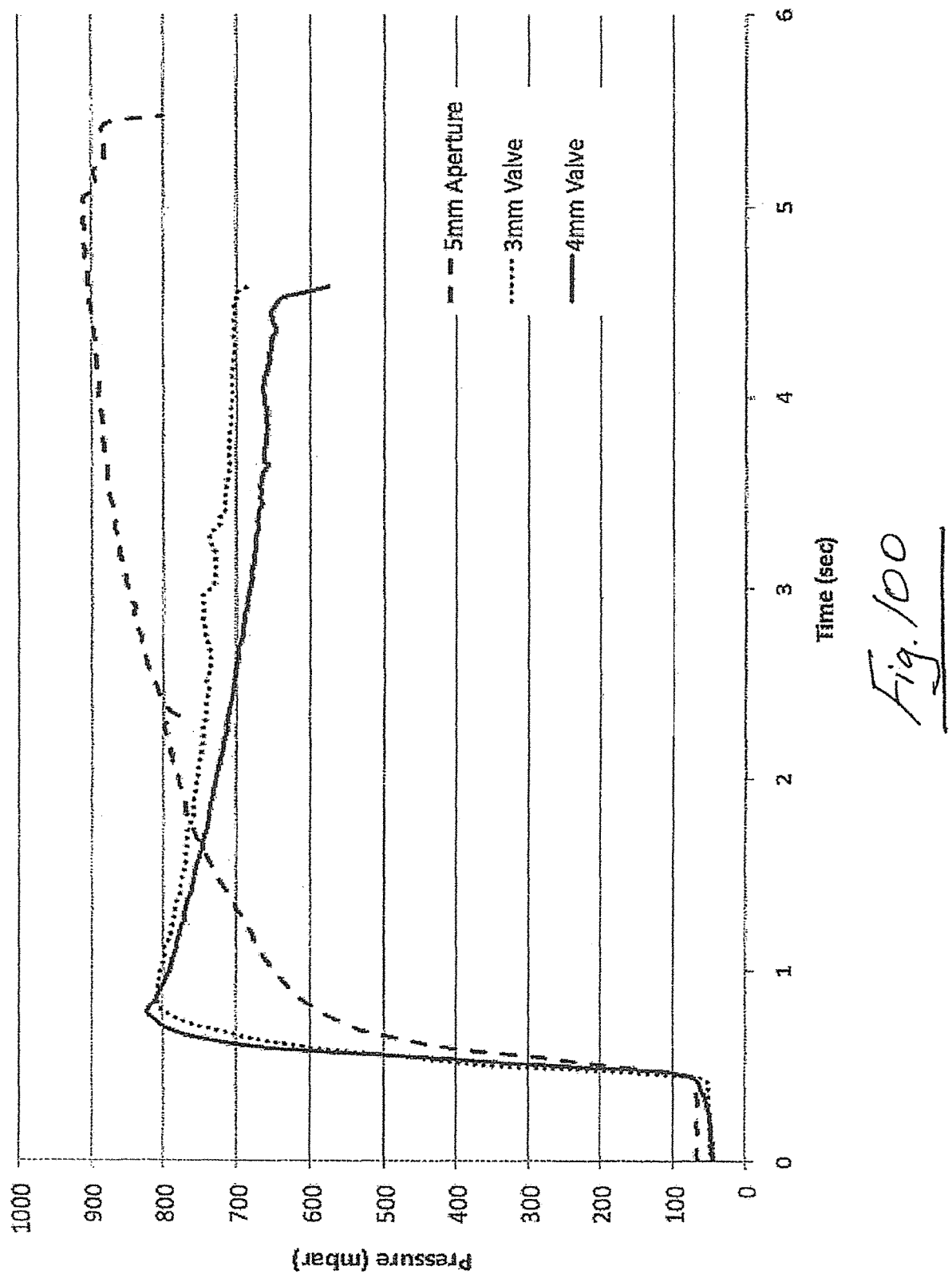
FIG. 100 is a graph of pressure profile over time with a fixed orifice restriction and implant devices comprising valves of the invention.

The performance of the valve can be tailored by adjusting the material density, this for example can be achieved by introducing more or less material into the valve forming mold, which subsequently expands to fill the cavity. Referring to FIG. 100, the valve was made using the same material as in FIG. 99 but in this case the density was changed to approximately 0.76 g/ml. Through this modification it was possible to produce a valve that generated an initially high back-pressure and subsequently adapted to the fluid flow thus lowering the back-pressure. Such a valve has an initial barrier function followed by a steady state restriction. The valve impedes flow until a pre-determined setpoint pressure after which the back pressure remains substantially constant thus providing a predictable stomach emptying rate.

Various materials can be used for fabrication of the sleeve portion of the device. These materials can be for example; polyethylene, PTFE or FEP due to their low friction thus not impeding fluid flow therethrough.

Figure 101:
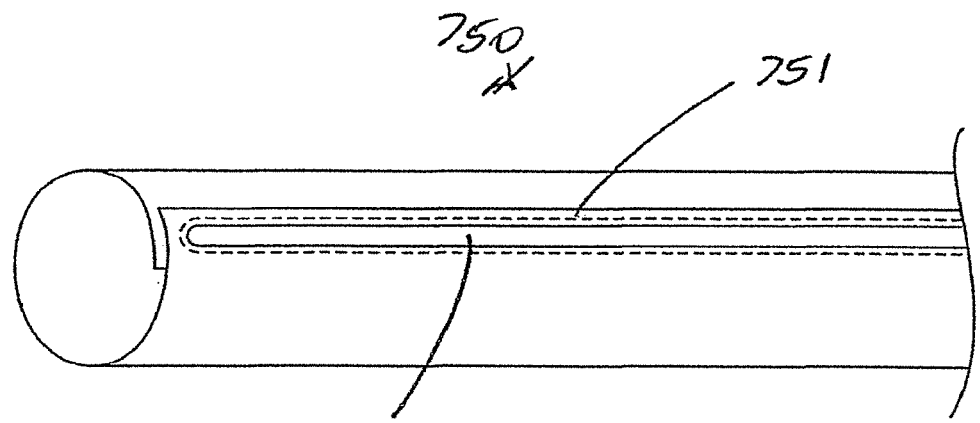
FIG. 101 is an isometric view of part of a sleeve according to the invention.
Figure 102:
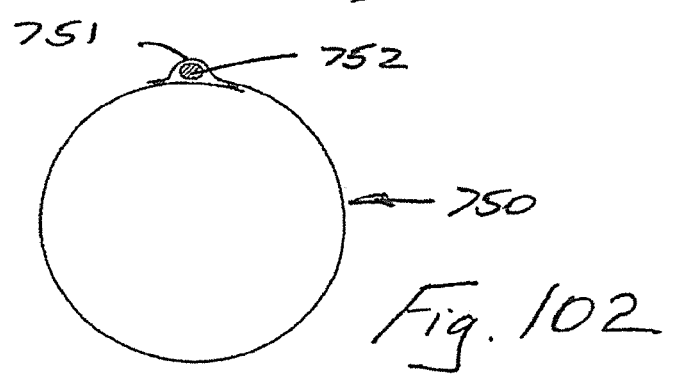
FIG. 102 is a cross sectional view of the sleeve of FIG. 93.
Figure 103:
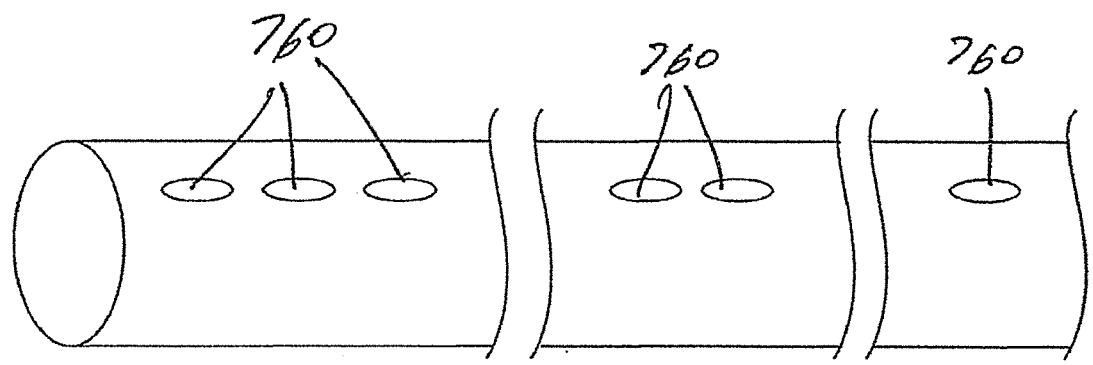
FIG. 103 is an isometric view of part of another sleeve according to the invention.

Referring to FIGS. 101 and 102 a sleeve 750 according to the invention has means to visualise the deployment of the sleeve using a radiopaque marker. A radiopague ink or paint is used. Because of the chemical nature of the sleeve materials the adhesion of a coating is very difficult. A longitudinal pocket 751 is provided which may be created by overlapping a portion of the sleeve material. Into this pocket 751 is deposited a radiopaque material 752 such as a liquid silicon resin filled with BaSO4, which is subsequently cured. This facilitates a low profile and a fluoroscopically distinguishable marker for visualisation in the body. Referring to FIG. 103 in this case the sleeve has a plurality of pockets 760 which may be arranged in any desired manner to facilitate visualisation, for example at particular locations.

The duodenum begins at the pylorus and forms a curved region immediately distal to the duodenal bulb. This region, known as the descending duodenum, is where chyme begins to mix with digestive secretions from the ampulla of Vater. As the chyme begins to digest it is absorbed by the luminal surface of the duodenum. The sleeve functions to bypass this absorption mechanism. The length of the sleeve liner can be sufficient to reach the distal duodenum coincident with the ligament of treitz, where the duodenum meets the Jejunum. Alternatively the sleeve can be shorter and the inhibition of absorption through the duodenal lumen will be proportional to the length of the sleeve. Given that most of the adsorption in the duodenum happens between the ampulla of Vater and Jejunum the sleeve should at least be long enough to traverse the ampulla. In addition, when the sleeve does not extend into the ligament of treitz, the sleeve is more easily delivered as it is not required to navigate through the tortuosity of the ligament of treitz. The typical length of the sleeve may be 40 cm to 45 cm.

Figure 104:
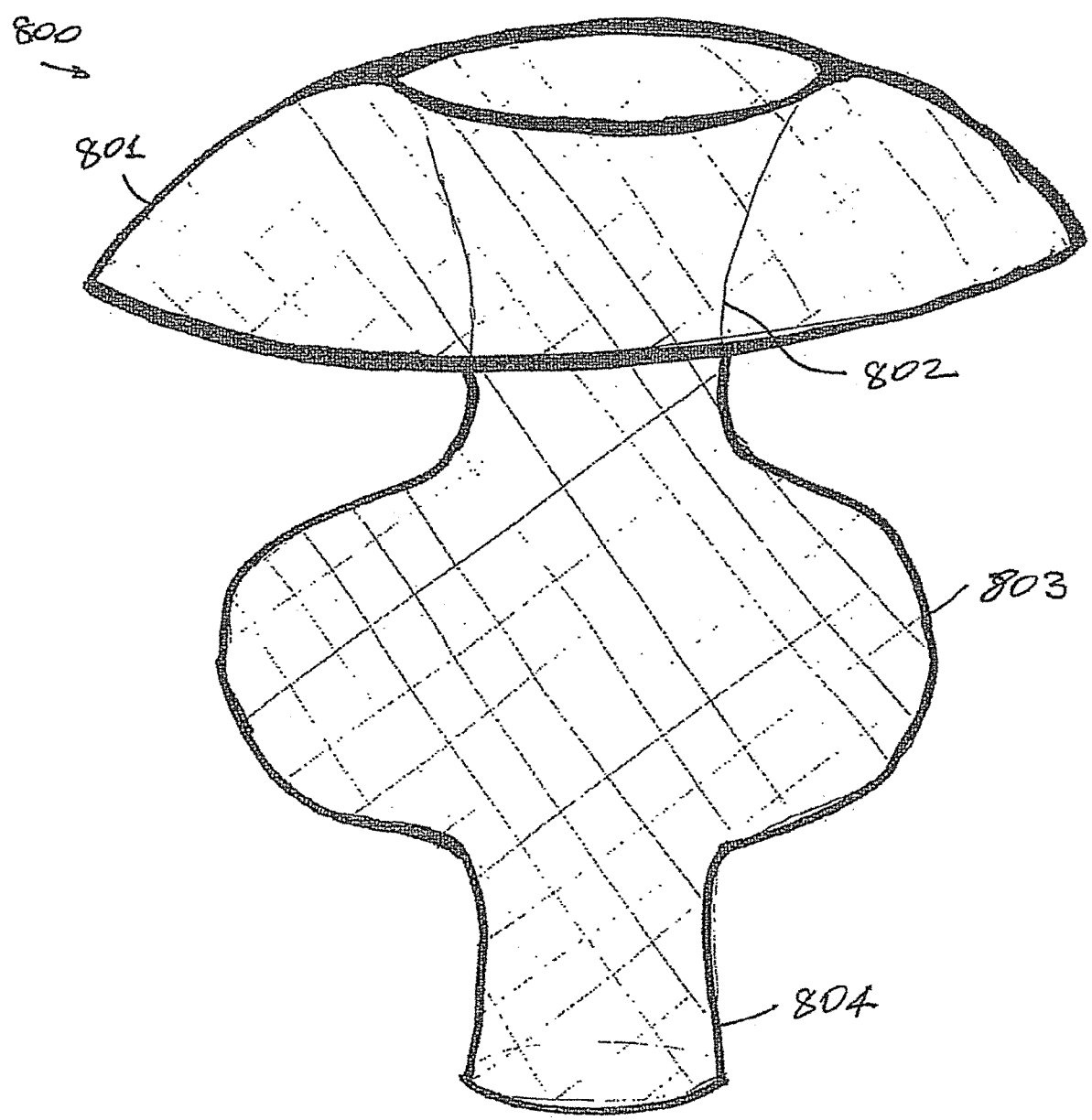
FIG. 104 is an isometric view of a luminal prosthesis according to the invention.

FIG. 104 is an illustration of a host luminal prostheseis or stent 800 according to the invention. The stent 800 comprises a funnel shaped region 801 to be placed in the antrun of the stomach. The host stent shown in FIG. 84 also has a funnel shaped region to be placed in the antrum of the stomach. Such a funnel shaped or flared region ensures that chyme flows through the lumen of the stent and not around the external surface of the stent. This is important as chyme being forced around the outside of the stent could cause compression and migration of the stent.

The funnel region 801 is connected to a softer narrower region 802 that is designed to traverse the pylorus. This region 802 is sufficiently compliant to allow the pylorus to close in response to physiological pressures.

This softer region 802 also has a means to allow coaxial connection of an obesity device such as a valve as shown in FIG. 77. The connection of an obesity device in the proximal part of the stent is important. By this methodology any drag force experienced by the obesity device due to food passage through the lumen can be transferred to other region(s) of the stent such as a distal bulbous region(s) 803 of the stent. The resulting compressive force can expand the bulbous region(s) 803 of the stent structure thus reinforcing the retention of the stent.

Connecting the bulbous region 803 to a trans-pyloric funnel 801 helps to locate the stent in the anatomy and prevent rotation of the bulb 803 perpendicular to the axis of the duodenal lumen.

The stent may also have a cylindrical region 804 that connects to the distal end of the bulbous region 803 for contacting with the tubular lumen of the duodenum.

The stent is a self expanding stent. The self expanding stent may be produced by knitting, braiding or weaving. In one case the stent is of a braided structure.

Self expanding braided or knitted stents can be made from either metal or synthetic polymers. If made from metal, a superelastic alloy is usually chosen because of the desired mechanical properties. These stents can be designed to exert significant radial force but at the same time be conformable and allow for the natural mechanical processes of digestion.

The technology might be most appropriately used in the gastro intestinal tract as described above.

One of the advantages of braided or knitted stents is that their radial diameter can be easily reduced to allow sheathing and delivery. This property is important when the stent is to be introduced into a narrow body lumen or even through the accessory channel of an endoscope.

However, because of the woven structure, the reduced diameter stent is often substantially longer than when its diameter is allowed to return to it's nominal state. This in turn causes a problem during deployment, whereby the stent foreshortens as it expands radially, making accurate placement a challenge. The user of such stents must always balance the advantages of their clinical benefit with the difficulty of delivery.

Because of the inter-relationship between the length and diameter of these stents, any force in the body that causes their elongation, will cause their diameter to shrink. This mechanical behaviour will ultimately result in loss of contact with the body lumen causing migration. Conversely, any force in the body that causes the stent to be longitudinally shortened will result in an axial expansion thus re-inforcing the stents position in the body lumen.

Such a stent may elongate when a relative tensile force is applied to either end and may shorten when a compressive force is applied to either end.

There are situations in which the use of a valve in a self expanding stent may be desirable and anatomical considerations may dictate that the valve be placed either at the proximal or distal end of the stent. A valve may experience a drag force from the flow of food through its lumen. If the valve is placed at the distal end of the stent, a tensile force may be created by the flow of food through the stent, whereas a compressive force could be created if the valve is placed at the proximal end of the stent.

Although the latter is more desirable from a retention standpoint it may not always be possible to position a valve in the proximal stent. It follows that valves placed at the distal end of the stent give rise to a heightened risk of migration.

The invention provides methodologies for the transfer of forces, experienced by distally placed valves, to the proximal region of a stent. Thus, a proximally placed valve could be made to exert a compressive force on the stent.

Figure 105:
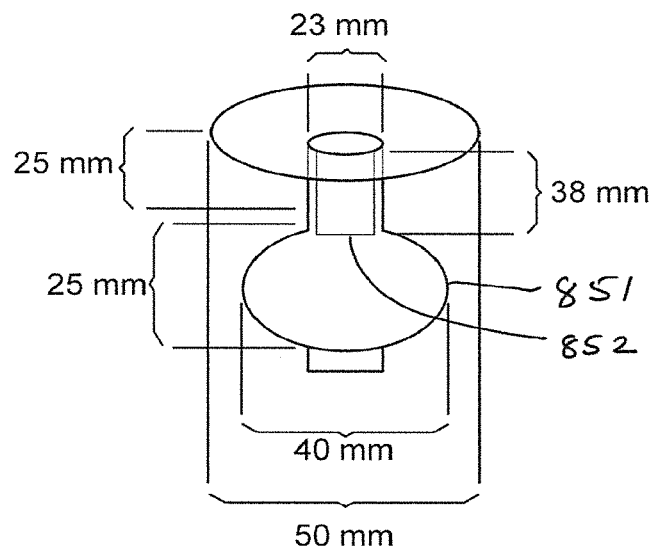
FIG. 105 is an isometric view of another luminal prosthesis according to the invention

The invention may be described broadly as follows: a stent that has an outer region 851 for contact with the body lumen, an inner region 852 for contacting with a valve (or such a prosthesis) and a connecting component for connecting the inner region to the proximal part of the outer region. One embodiment is illustrated by FIG. 105. The outer region may be contoured to fit the appropriate body lumen. The dimensions indicated in FIG. 105 are particularly appropriate for a prosthesis which is to be located in the antrum of the stomach and extend through the pylorus.

Figures 106, 108:
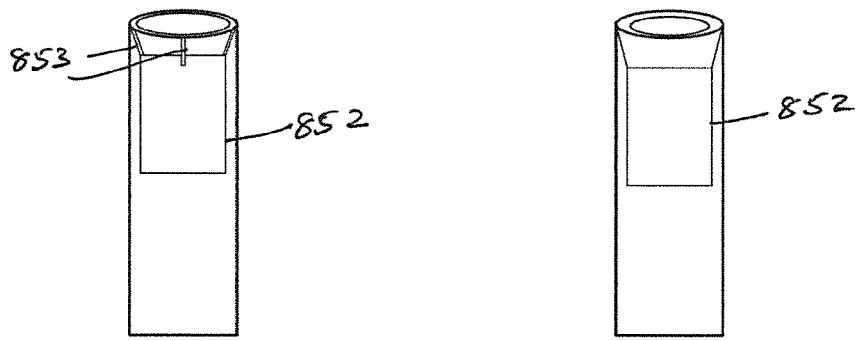
FIGS. 106 and 107 are views of a luminal prosthesis in which inner and outer regions are connected by struts or vines.
FIGS. 108 and 109 are views of a continuous stent which has been folded or partially inverted to generate two coaxial regions.
Figure 107:
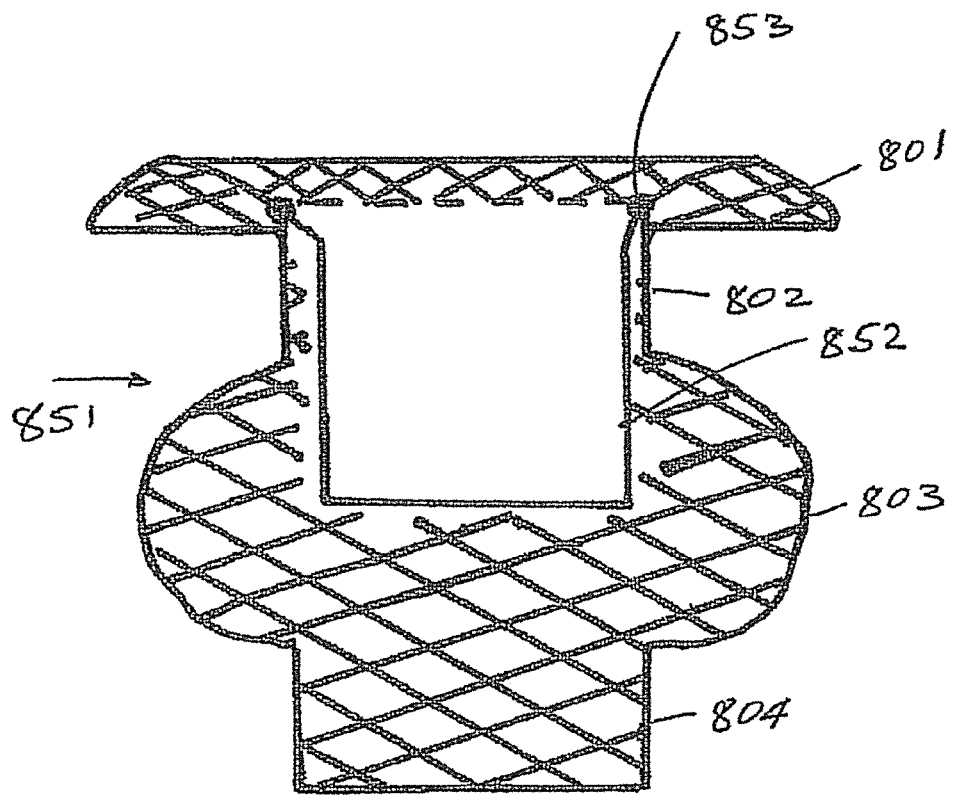

The connecting region may be formed by discrete struts, wires or other structures 853 as shown in FIGS. 106 and 107. Alternatively the inner and outer regions may be formed by one continuous stent folded so as to form coaxial inner and outer regions 851,852 FIGS. 108 and 109.

There are situations in which the placement of a valve and support structure in an already deployed self expanding stent (host stent) may be desirable. Such a valve component may anchor itself in the host stent by means of radial force, friction or by some mechanically interlocking mechanism.

Figure 110:
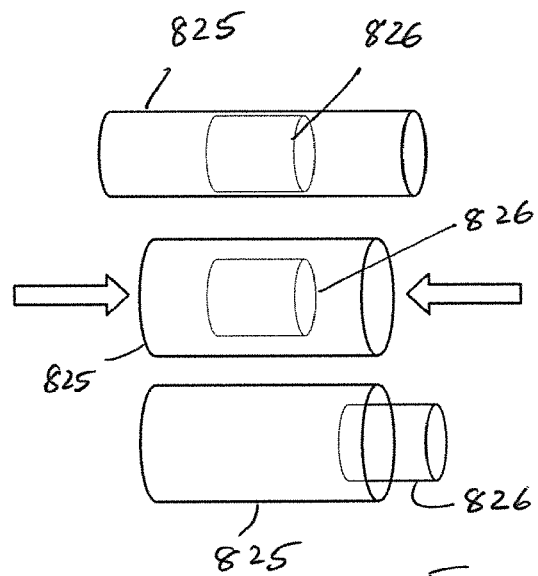
FIG. 110 is an illustration of the longitudinal shortening of a stent resulting in migration of a valve device.

Any forces exerted on the stent and valve system that cause the stent to foreshorten and compress will result in an expansion of it's diameter. This behaviour would likely cause any coaxially located valve component to loose engagement with the inner lumen of the stent and thus migration would occur as shown by FIG. 110. FIG. 110 illustrates longitudinal shortening of a stent 825 (such as a braided stent) resulting in migration of a valve device 826.

Figure 111:
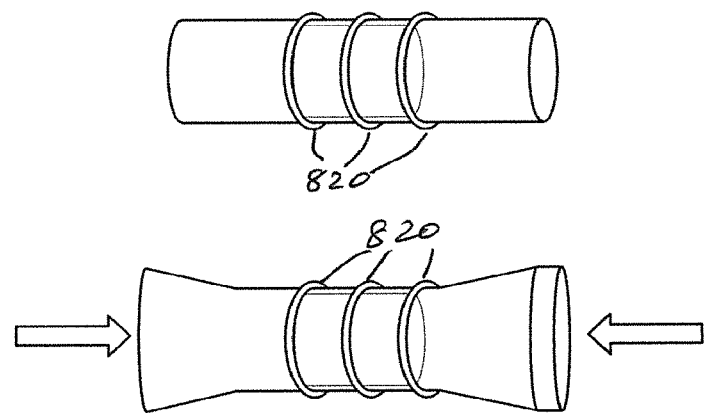
FIG. 111 are views of a stent with restricting loops for restricting expansion of a section of a self expanding stent.
Figure 112:
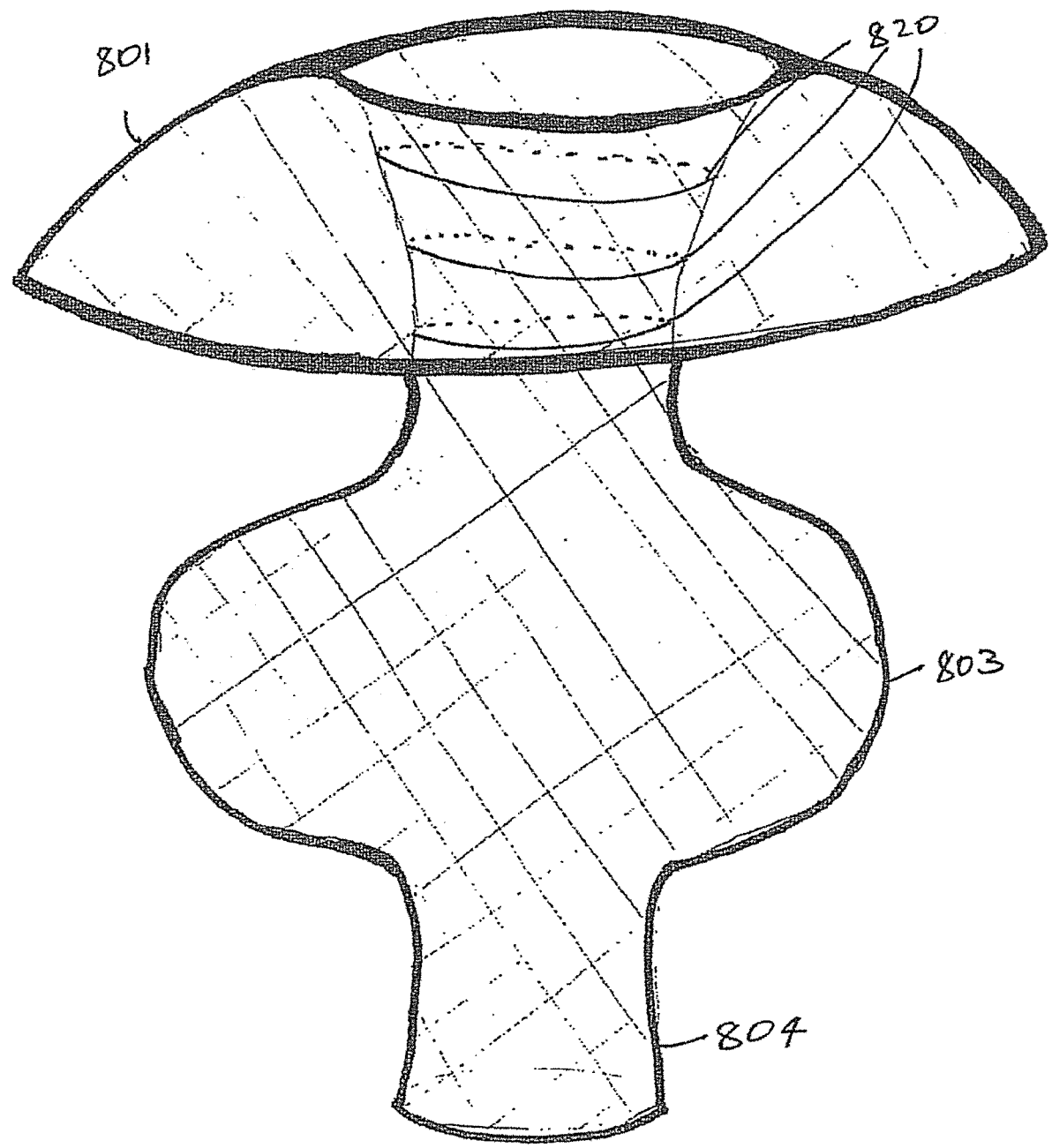
FIGS. 112 and 113 are views of stents with restricting loops.
Figure 113:
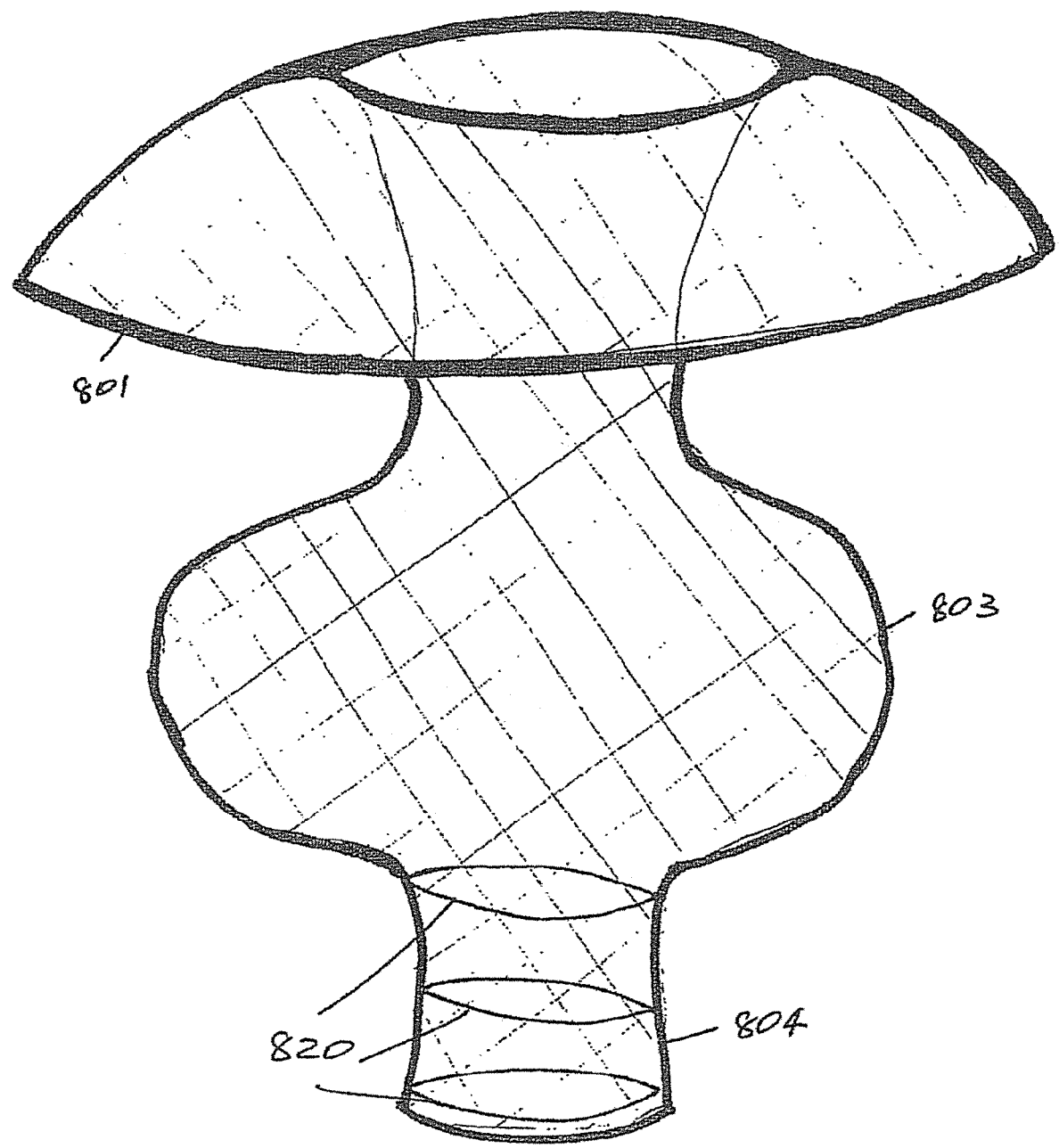

One aspect of the invention involves the addition of a non-distensible loop or series of loops 820 to the circumference of a self expanding stent restricting expansion of a section of a self expanding stent as shown by FIGS. 111, 112 and 113. The loops 820 which may be made from a flexible material such as a polymeric or metallic thread allow radial compression of the stent during loading but limit radial expansion to the pre-determined diameter of the loop. Exemplary materials are either monofilament or braided polypropylene suture or stainless steel wire.

By using this methodology the valve component, which may be placed within the region with added loops, will not be displaced by any longitudinal forces on the stent.

Figure 114:
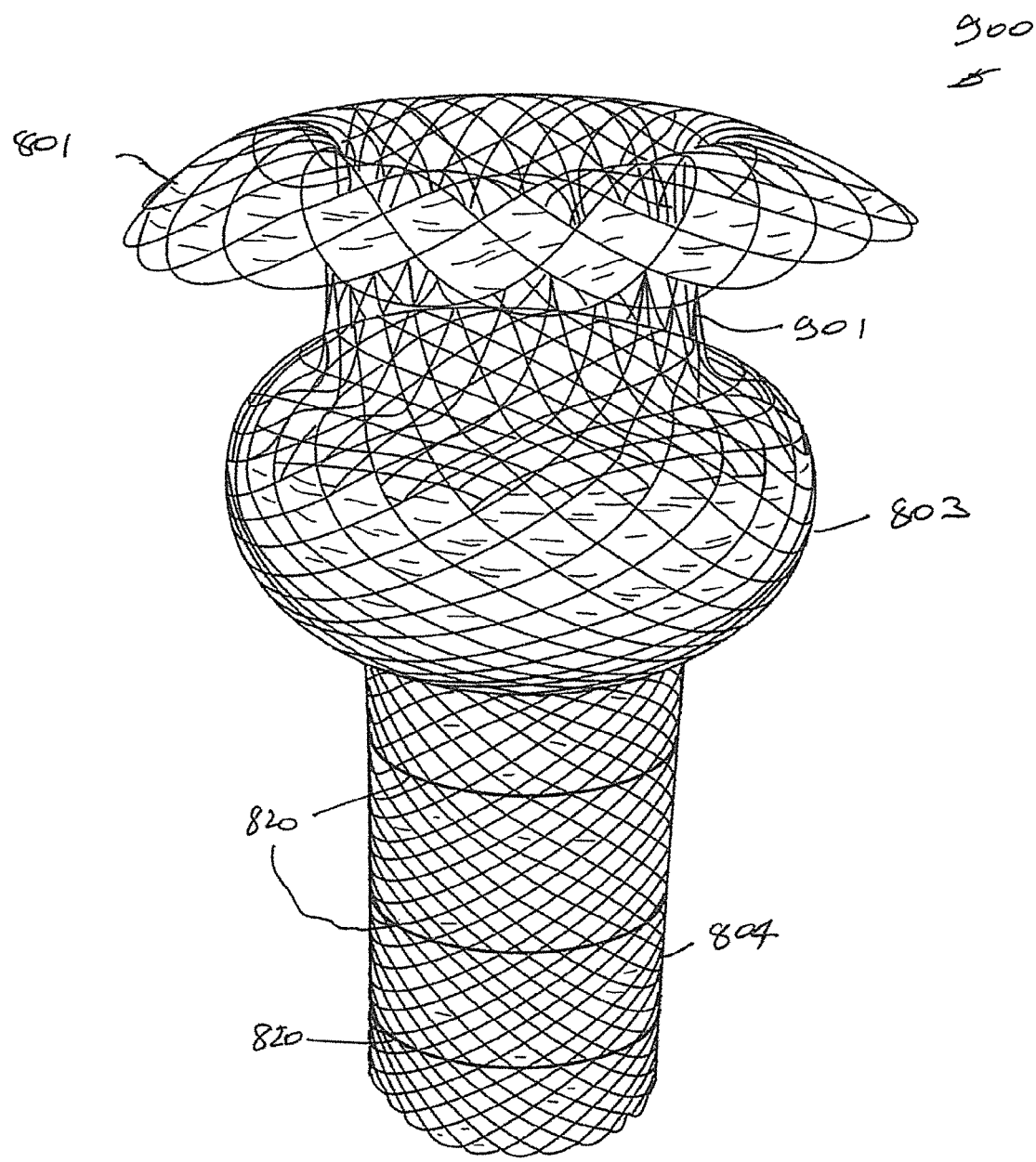
FIG. 114 is an isometric view of another luminal prosthesis according to the invention.

Referring to FIG. 114 there is illustrated another endoluminal prosthesis 900 according to the invention. The prosthesis is similar to the prosthesis of FIG. 113 and like parts are assigned the same reference numerals. The prosthesis is of braided mesh construction and comprises a proximal flare or umbrella region 801, a bulbous region 803 and a duodenal region 804. A transpyloric region 901 interconnects the proximal flare 801 around the bulbous region 803.

The proximal umbrella region 801 is of open mesh and is relatively soft to avoid tissue irritation. The periphery of the proximal flare is in this case at least partially coated with a suitable coating material. The coating in this region functions as a deployment aid as it prevents sticking between the adjacent regions when the stent is in a collapsed delivery configuration. The turning of the flare distally provides some axial drag which provides resistance against dislodgment in use, for example when located at the pylorus.

The transpyloric region 901 is very soft and pliable to resist force transmission from the proximal flare 801 to the bulbous region 803. The transpyloric region may be uncoated to allow some tissue ingrowth.

The bulbous region 803 acts to assist retention of the device by engaging in the duodenal bulb. The mesh is flexible in this region to adapt to the anatomy in which it is deployed. A lower part of the bulbous region 803 may be coated to prevent tissue ingrowth.

Figures 115, 116:
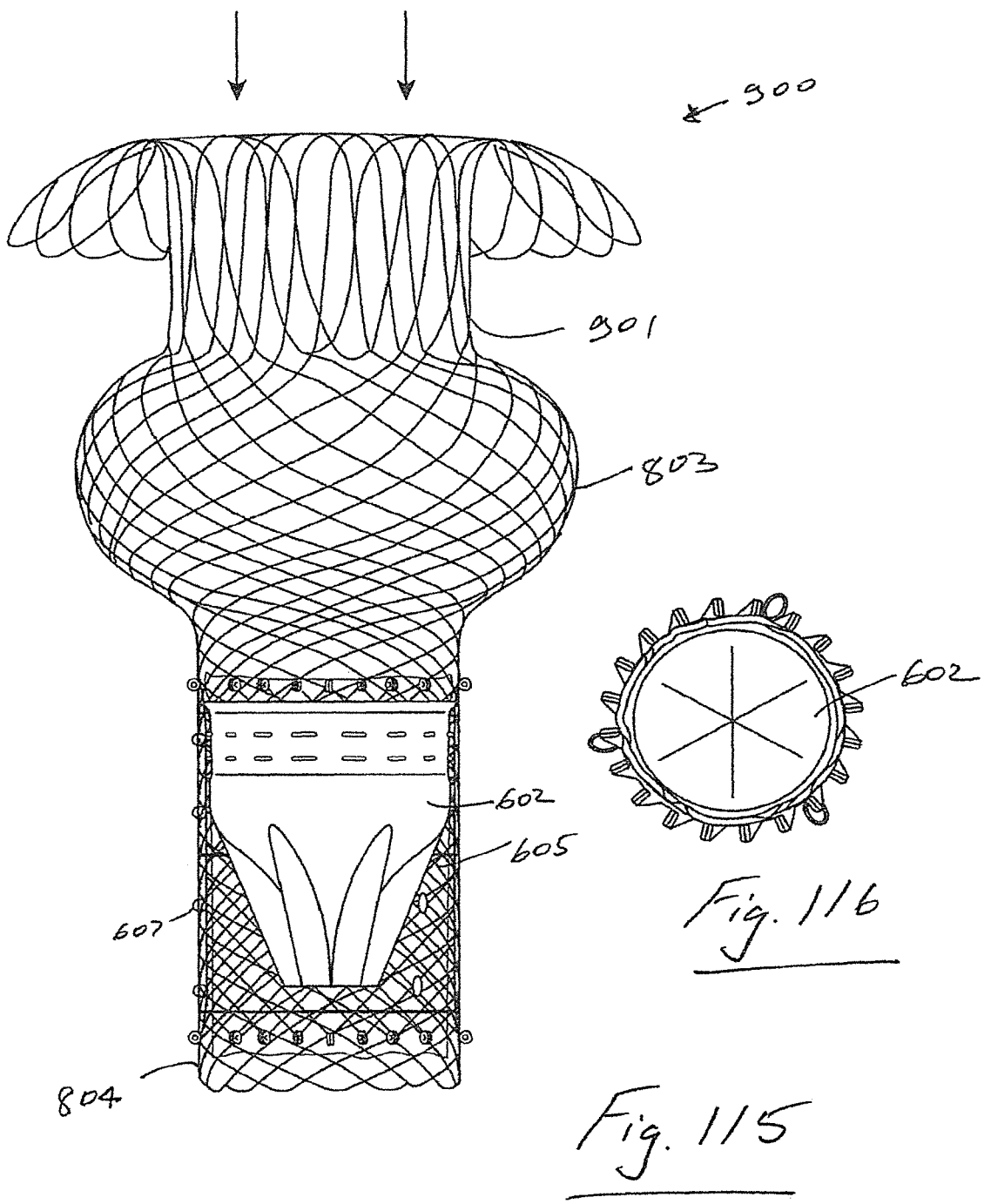
FIG. 115 is a view of the prosthesis of FIG. 114 with a valve and scaffold in position.
FIG. 116 is a plan view showing the valve in a closed configuration.
Figure 117:
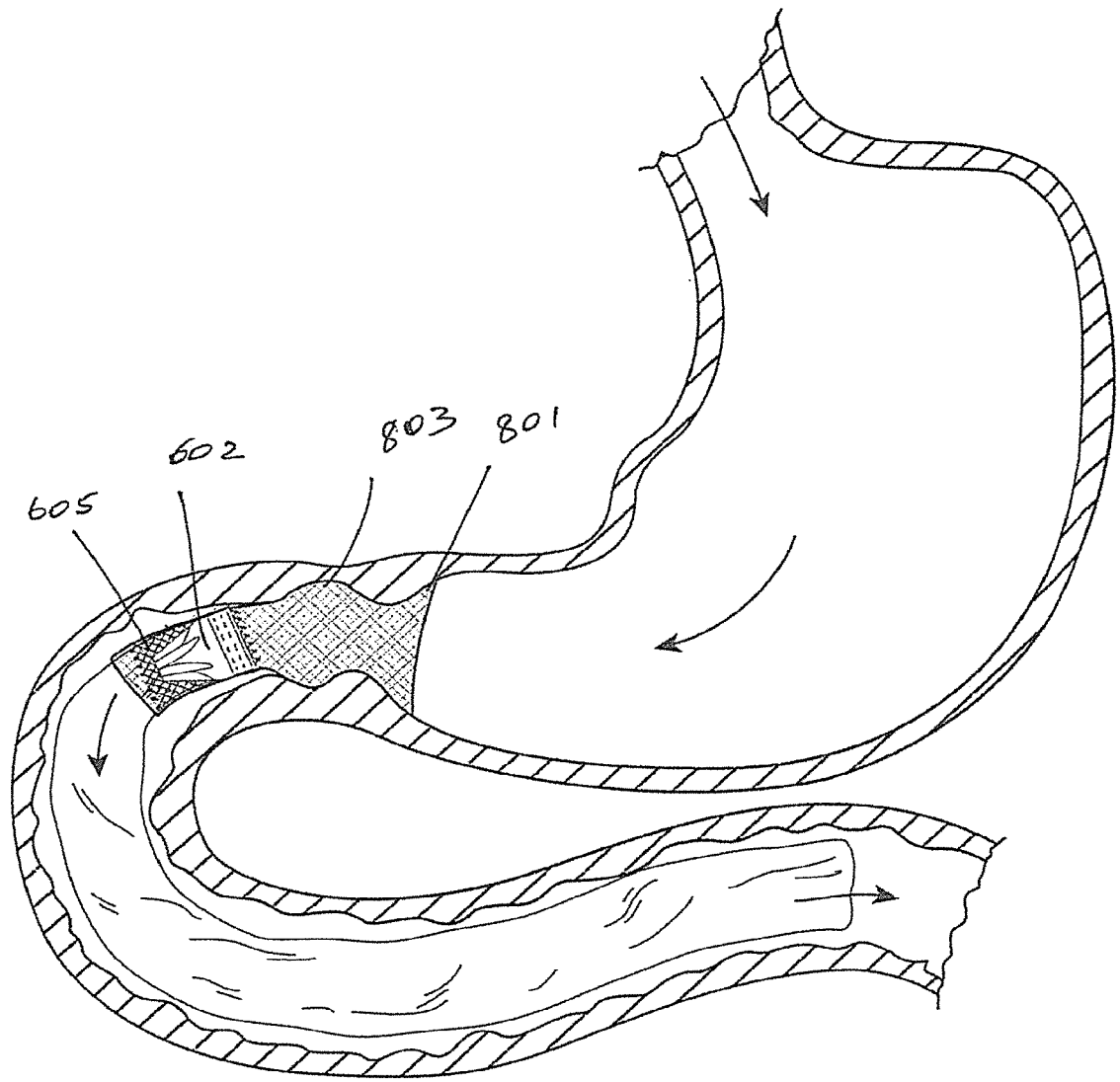
FIG. 117 is an isometric view of an obesity treatment device in situ incorporating the device of FIGS. 114 to 116.

The duodenal region 804 is designed such that its diameter will not expand beyond a pre-seat limit. The braid/mesh has a weave which is more dense than the other regions as the duodenal region in this case is the region in which a valve 602 and associated scaffold 605 are deployed—as illustrated in FIGS. 115 to 117. The valve and scaffold may, for example, be as described above—such as those described with reference to FIGS. 73 to 97.

Figure 109:
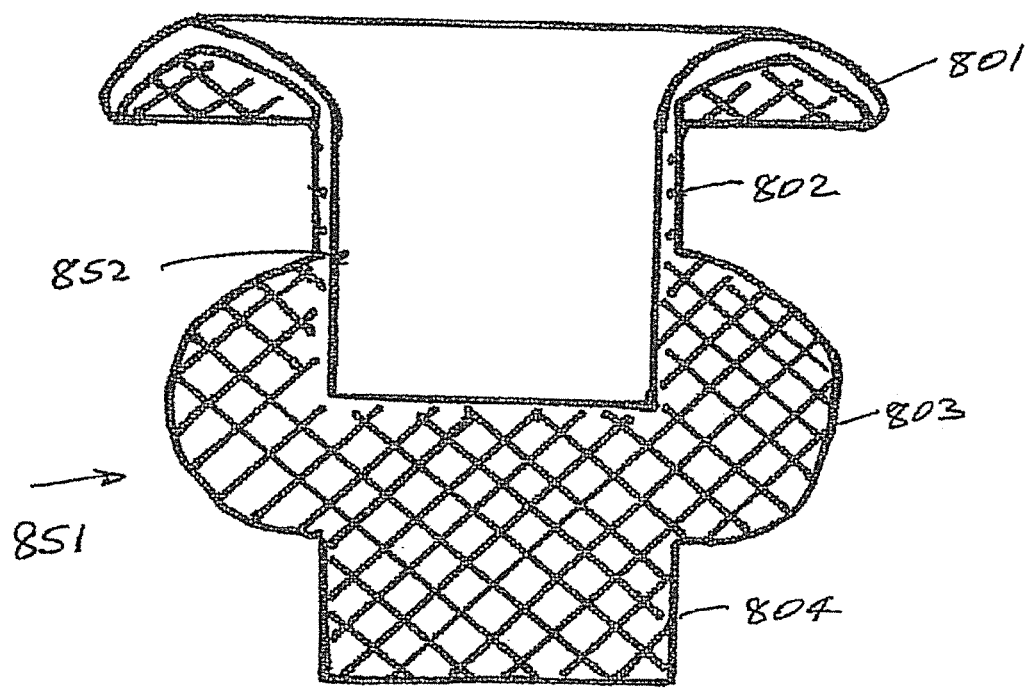
Figure 118:
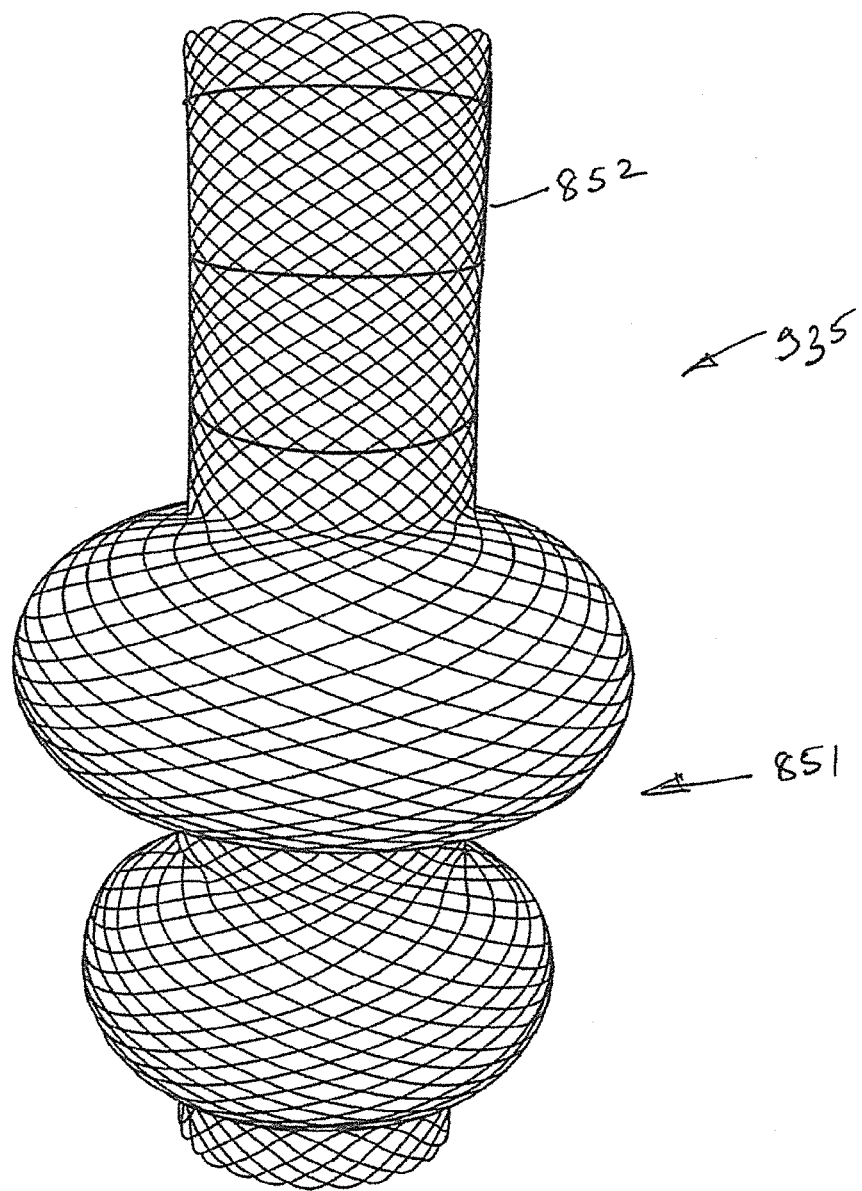
FIG. 118 is an isometric view of a precursor to another luminal prosthesis according to the invention.
Figure 119:
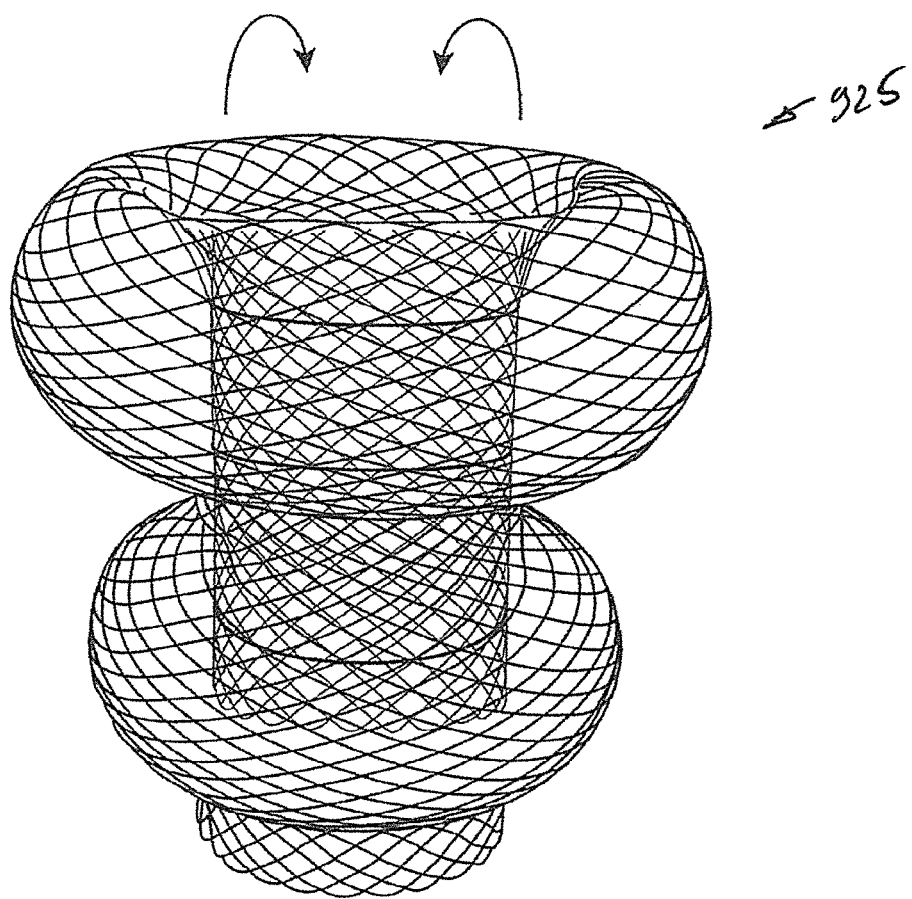
FIG. 119 is a view of the precursor of FIG. 118 being folded.
Figure 120:
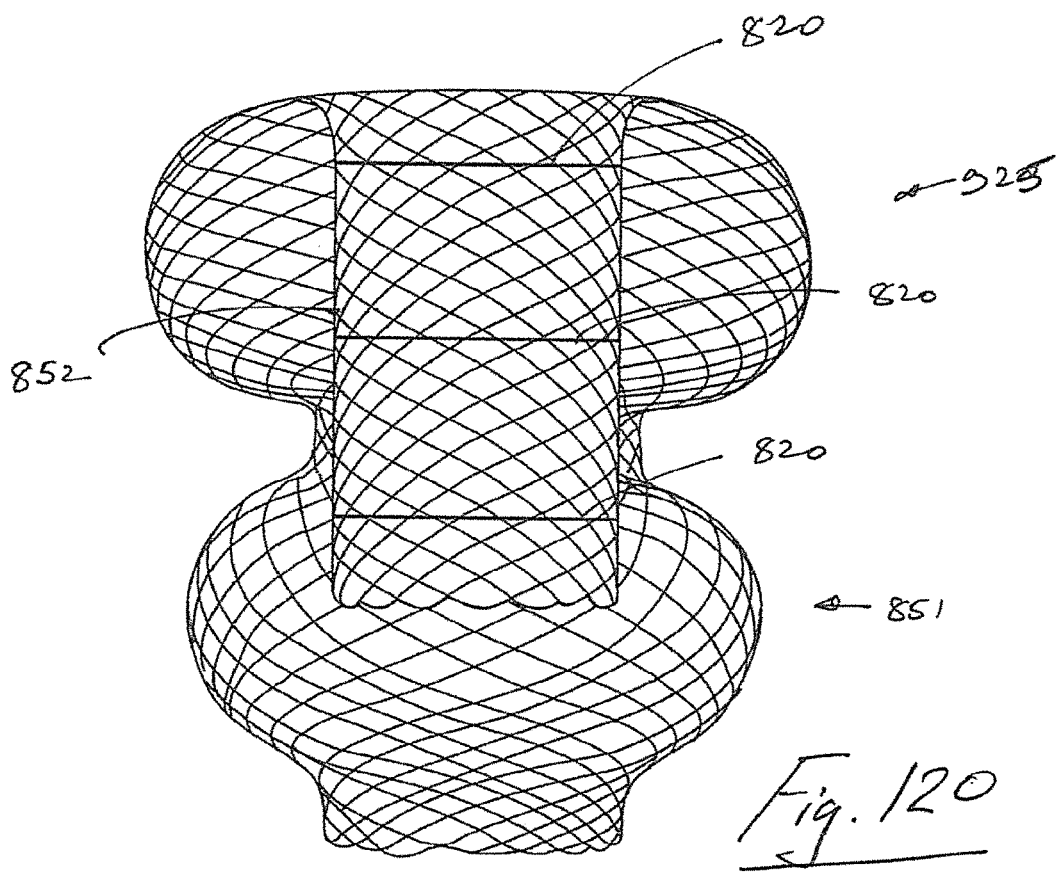
FIG. 120 is a view of a luminal prosthesis formed from the precursor of FIG. 118.
Figure 121:
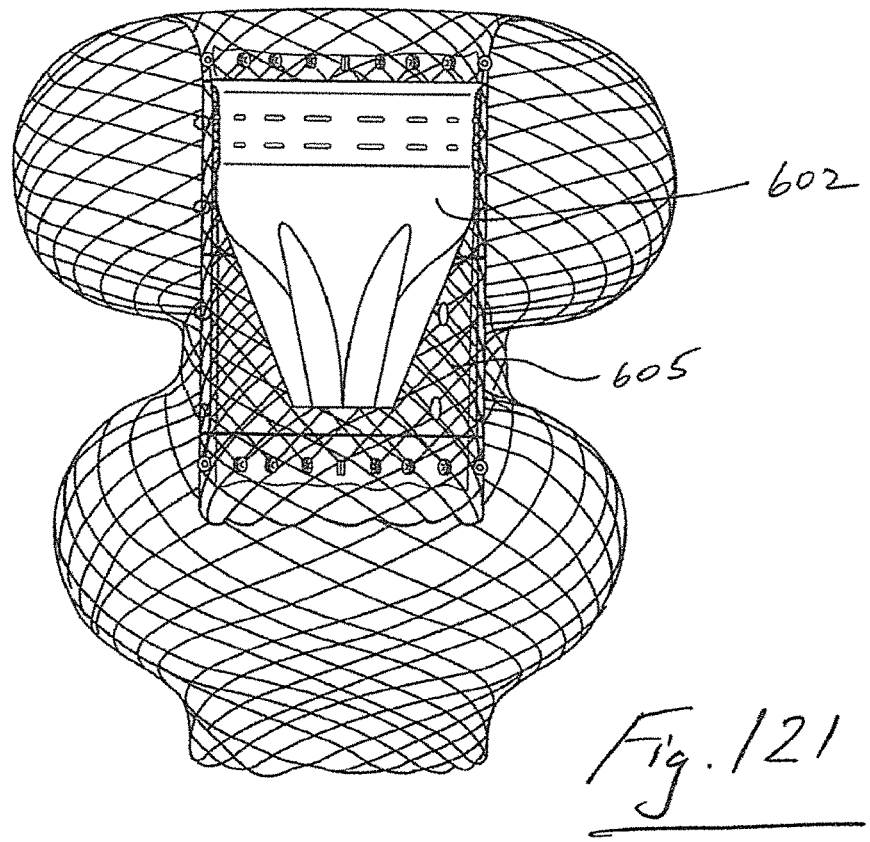
FIG. 121 is a view of the luminal prosthesis of FIG. 120 with a valve and scaffold in situ.
Figure 122:
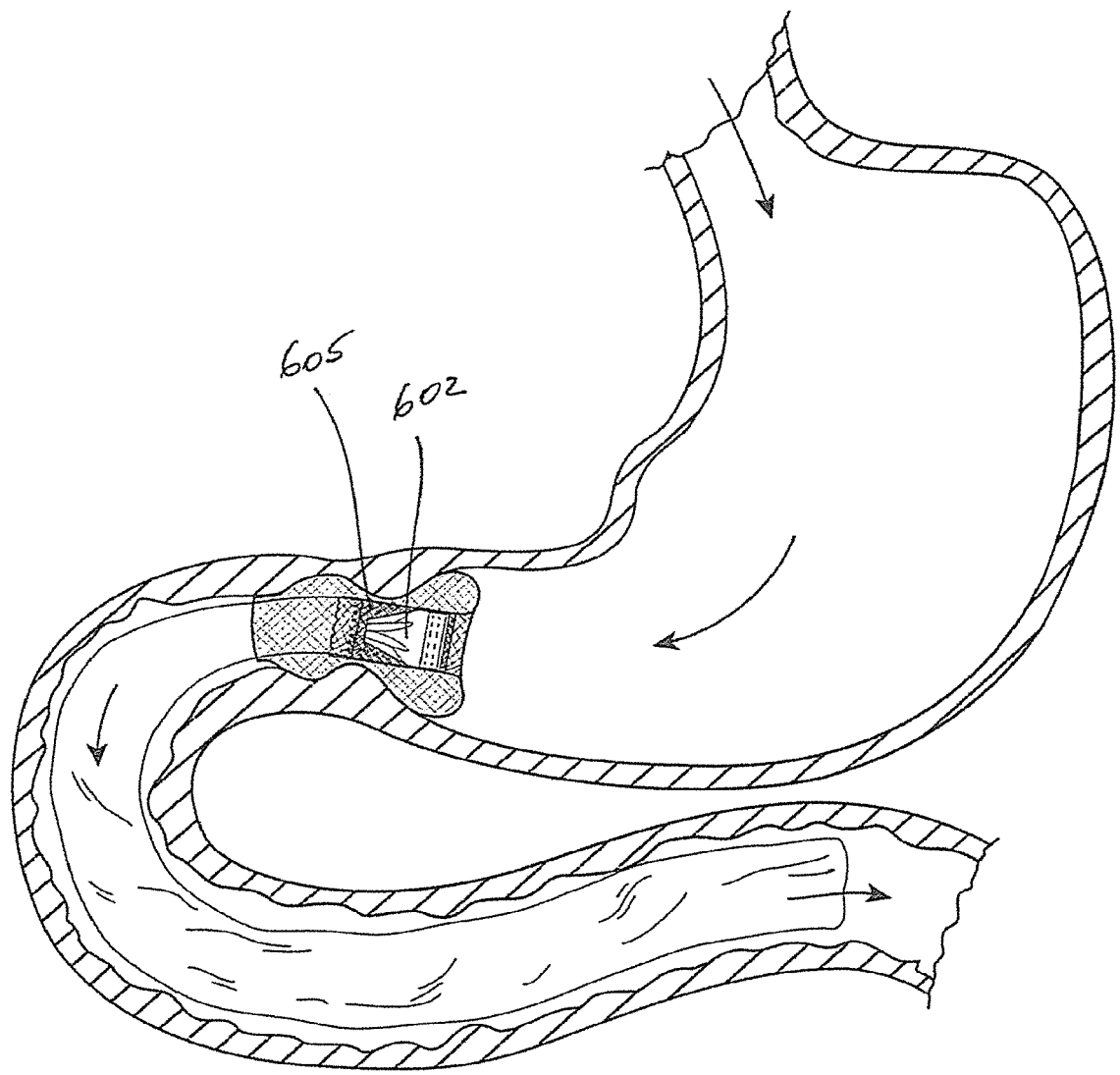
FIG. 122 is an isometric view of an obesity treatment device in situ incorporating the device of FIGS. 120 and 121.

FIG. 120 illustrates another luminal prosthesis 925 according to the invention which has some features similar to the prosthesis of FIG. 109 having coaxial inner and outer regions 851, 852. In this case the inner and outer regions 851, 852 are formed by one continuous precursor stent 935 (FIG. 118) which is folded as illustrated in FIG. 119. The inner region 852 is in this case adjacent to the proximal end of the prosthesis and a scaffold and valve of the type previously described can be readily deployed. FIG. 121 shows the luminal prosthesis of FIG. 120 with a valve and scaffold in situ. FIG. 122 illustrates an obesity treatment device according to the invention in situ which incorporate the device of FIGS. 120 and 121. The arrangement ensures that any movement of the valve is effectively isolated from any forshortening or otherwise of the outer region of the stent.

Another luminal prosthesis 928 according to the invention is illustrated in FIGS. 123 to 125. This prosthesis 928 is similar to the prosthesis of FIG. 107 and FIGS. 124 and 125 illustrate how the inner part of the prosthesis is at least partially isolated from the outer part by virtue of the connection 853 which may for example define a region of at least partial articulation/hinging/pivoting.

Figure 126:
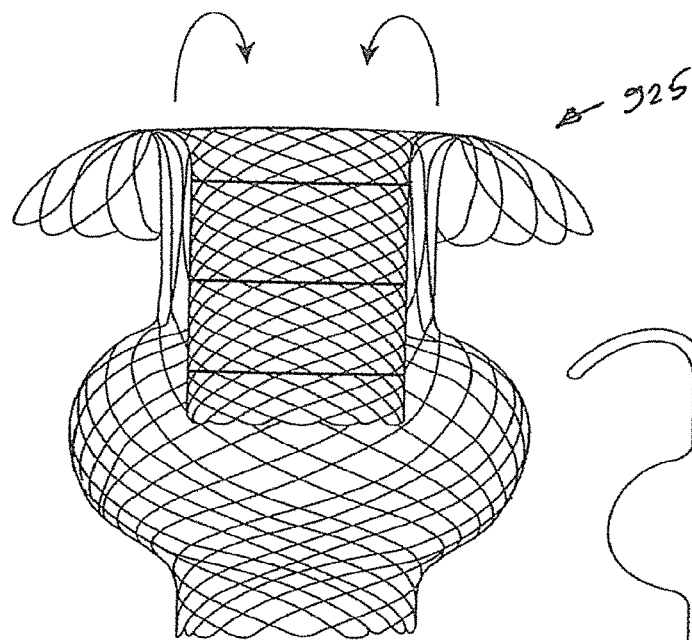
FIG. 126 is an isometric view of a still further luminal prosthesis according to the invention.

FIG. 126 illustrates another luminal prosthesis 925 according to the invention which is somewhat similar to the prosthesis of FIGS. 109. The functioning of the prosthesis 925 is diagrammatically illustrated in FIGS. 127 to 129.

Figure 127:
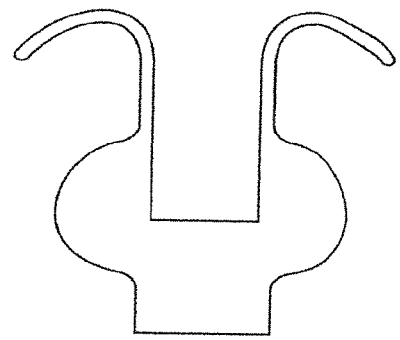
FIGS. 127 to 129 are diagrams illustrating different configurations of the prosthesis of FIG. 126.
Figure 128:
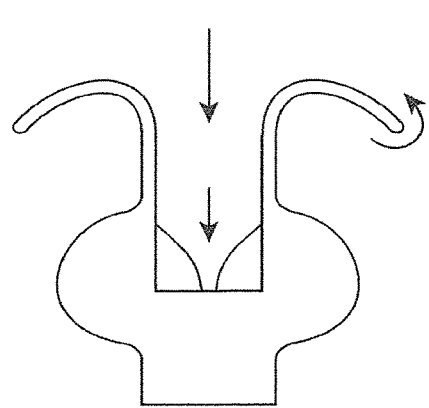
Figure 129:
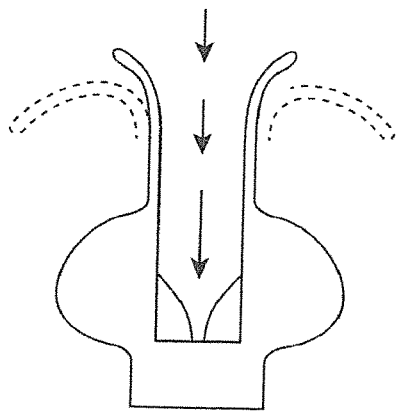

A similar prosthesis is illustrated in FIG. 126 and the functioning of the device is diagrammatically illustrated in FIGS. 127 to 129.

Figure 130:
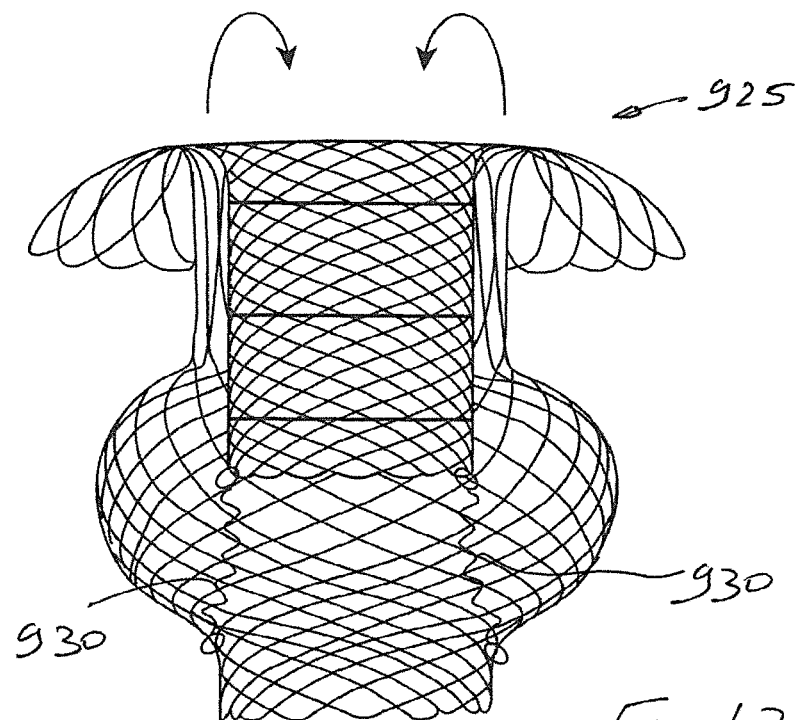
FIG. 130 is an isometric view of a further luminal prosthesis according to the invention.
Figure 131:
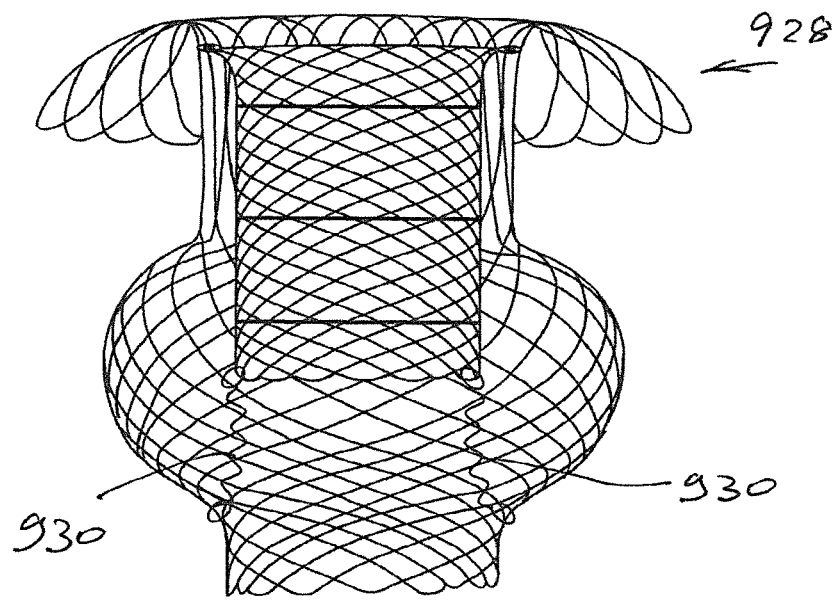
FIG. 131 is an isometric view of another luminal prosthesis according to the invention.

In some cases, as illustrated in FIGS. 130 and 131 there may be an additional axially flexible connector such as at least one tether 930 between the inner and outer parts.

Figure 132:
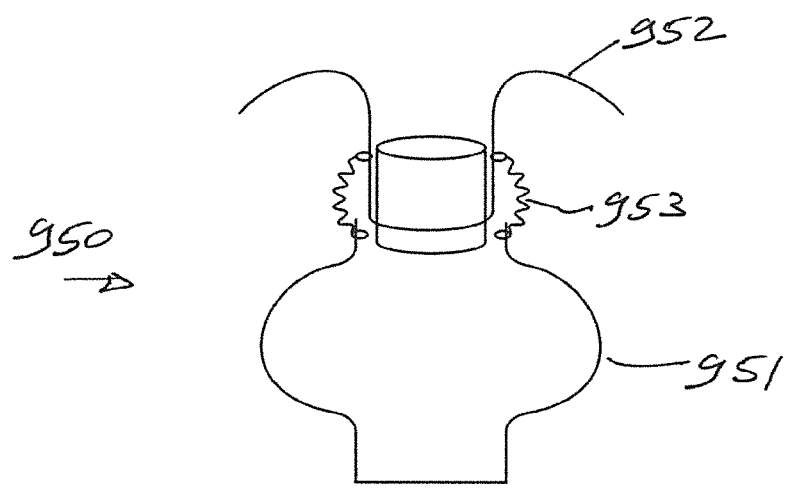
FIG. 132 is an isometric view of a still further luminal prosthesis of the invention.

Referring to FIG. 132, in this case a prosthesis 950 comprises a bulbous part 951 which is separate from a proximal flare part 952. The parts 951, 952 may be interconnected by any suitable connector(s) 953 such as at least one tether. The proximal flare may have a partial transpyloric region to which a valve/scaffold may be mounted.

Referring to digs 133 to 139, there is illustrated another obesity treatment device 960 according to the invention. The device 960 comprises an external support 961, a valve 962 mounted to an internal support 963 and a sleeve 964 which extends in use into the duodenum as described above.

The external support 961 has a proximal flare portion 970 and a distal bulbous region 971. The distal bulbous region and the proximal flare region are connected view a transpyloric cylindrical region. The radial force of the cylindrical legion is low to allow normal functioning of the pyloric sphincter. The proximal flare portion 970 is of open mesh construction and does not require a coating. It engages with the antrum of the stomach which retains it in place. At least a distal portion of the bulbous region 971 of the external support 961 is coated.

The valve 962 is mounted to the internal support 963 and the internal support 963 in turn is engaged with the coated distal portion of the bulbous region 971 of the external support 961. The internal support 963 has integral hoops 972 which engage in the mesh of the external support 961 to assist in retaining the scaffold 963 in situ. The internal support 963 is free to move relative to the external support 961 but does not impinge upon the tissue of the duodenal bulb.

In use, when food is passing from the stomach through the valve 962 a proximal portion of the internal scaffold 963 moves relative to the external support 961 which causes axial force to be translated both distally and radially. The resultant force vector augments the radial force on the external support 961 and absorbs axial force. The proximal portion of the internal support 963 can move axially distally because it is not coupled to the external support 961. The distal portion of the internal support 963 only interacts with the external support 961 and does not extend through the external support 961. The inner support 961 does not engage with the wall of the duodenal bulb.

The obesity treatment device does not interfere with the functioning of the pyloric sphincter. The pylorus functions normally whilst ensuring that the device is anchored in place. When food is passing through the valve the force applied is translated into a radial force on the duodenal bulb which is sufficiently pliant to distend and absorb this force. The device functions to retard the emptying of the stomach to give the user a prolonged feeling of saiety.

In recent years there has been a significant upsurge in commercial activity related to implantable devices to treat obesity. Some of these devices are intended for use in the pylorus and duodenum and thus require some form of retention. Current retention modalities include the use of tissue penetrating barbs, which create ulceration and pain. This gastrointestinal implant device avoids the use of such barbs.

This technology will find commercial application in the emerging area of obesity treatment for improving the retention of devices that will be exposed to the high forces associated with food flow through the GI tract.

Various technologies which may be suitable for use in or in association with the device of the invention are described in the following US patent applications:
U.S. Ser. No. 12/488,037 (published as US2010-0121462A);
U.S. Ser. No. 12/488,016 (now U.S. Pat. No. 8,029,557);
U.S. Ser. No. 12/487,991 (published as US2010-0121461A);
U.S. Ser. No. 12/971,458 (published as US2011-0190905A);
U.S. Ser. No. 13/493,904 (published as US2012-0310138A); and
U.S. Ser. No. 13/329,728 (published as US2012-0158026A)
the entire contents of all of which are herein incorporated by reference.

A first Group of biomaterials that are suitable for manufacturing a valve of the invention is described in our U.S. Ser. No. 12/488,047 (now U.S. Pat. No. 7,932,343) and WO2009/153769, the entire contents of which are herein incorporated by reference. A second Group of biomaterials that are suitable for manufacturing a valve of the invention is described in our U.S. Ser. No. 12/971,384 (published as US2011-0152395A) and WO2011/073967A, the entire contents of which are herein incorporated by reference.

Various features of the invention are described in detail and illustrated herein. Appropriate features described with reference to one embodiment may be utilised in addition to and/or as a substitute for features described in other embodiments.

The invention is not limited to the embodiments hereinbefore described, with reference to the accompanying drawings, which may be varied in construction and detail.

What is claimed is:

1. A valve device comprising:
a valve having a proximal rim, three leaflets extending inward from the proximal rim, with each of the three leaflets having a leg portion that is adapted to contact an adjacent leg portion of an adjacent one of the three leaflets to provide the valve with a closed position;
a scaffold connected coaxially to an external surface of the valve;
a luminal prosthesis that is adapted to be implanted into a lumen of a patient, with the scaffold and the valve removably attachable inside of the luminal prosthesis; and
means for releasing the scaffold and the valve from the luminal prosthesis;
wherein the luminal prosthesis includes a bulbous region, a first region formed on a distal side of the bulbous region, a second region formed on a proximal side of the bulbous region, and a flared part that extends a radial distance from a proximal end of the second region to form an outermost flare diameter that defines a maximum width of the luminal prosthesis;
wherein the flared part is movable between a pre-loading configuration, in which an outermost edge of the flared part is located distal to the proximal end of the second region, and a deployed configuration, in which the outermost edge of the flared part is located proximal to the proximal end of the second region.

2. The valve device of claim 1, further comprising:
a coating applied to the luminal prosthesis as a deployment aid to facilitate placement into the lumen of the patient.

3. The valve device of claim 1, wherein the luminal prosthesis is radially collapsible to first diameter and self-expanding to a larger second diameter.

4. The valve device of claim 1, wherein the luminal prosthesis is formed from a braided mesh.

5. The valve device of claim 1, wherein the first region formed on the distal side of the bulbous region is coated to prevent tissue ingrowth.

6. The valve device of claim 1, wherein the luminal prosthesis is a woven mesh, and the scaffold and the valve are located at a region inside of the luminal prosthesis where the region of the luminal prosthesis has a more dense weave than other portions of the woven mesh of the luminal prosthesis.

7. The valve device of claim 1, wherein the luminal prosthesis is a braided mesh, and a weave of the braided mesh of the first region is more dense than a weave of the of the braided mesh of the second region.

8. The valve device of claim 1, wherein the flared part is connected to the proximal end of the second region by a connector.

9. The valve device of claim 1, wherein the scaffold and the valve are removably attachable inside of the first region of the luminal prosthesis distal from the bulbous region.

10. The valve device of claim 1, wherein the scaffold is a mesh formed from a shape memory metal.

* * * * *

UNITED STATES PATENT AND TRADEMARK OFFICE
CERTIFICATE OF CORRECTION

PATENT NO. : 10,973,668 B2  
APPLICATION NO. : 16/052614  
DATED : April 13, 2021  
INVENTOR(S) : Niall Behan Page 1 of 2

It is certified that error appears in the above-identified patent and that said Letters Patent is hereby corrected as shown below:

In the Drawings

Figure 88:
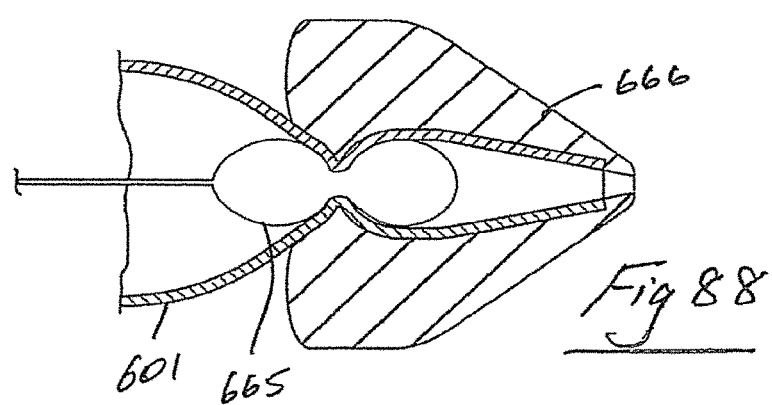
FIG. 88 is an enlarged cross sectional view of a distal end of the delivery system.
Figure 89:
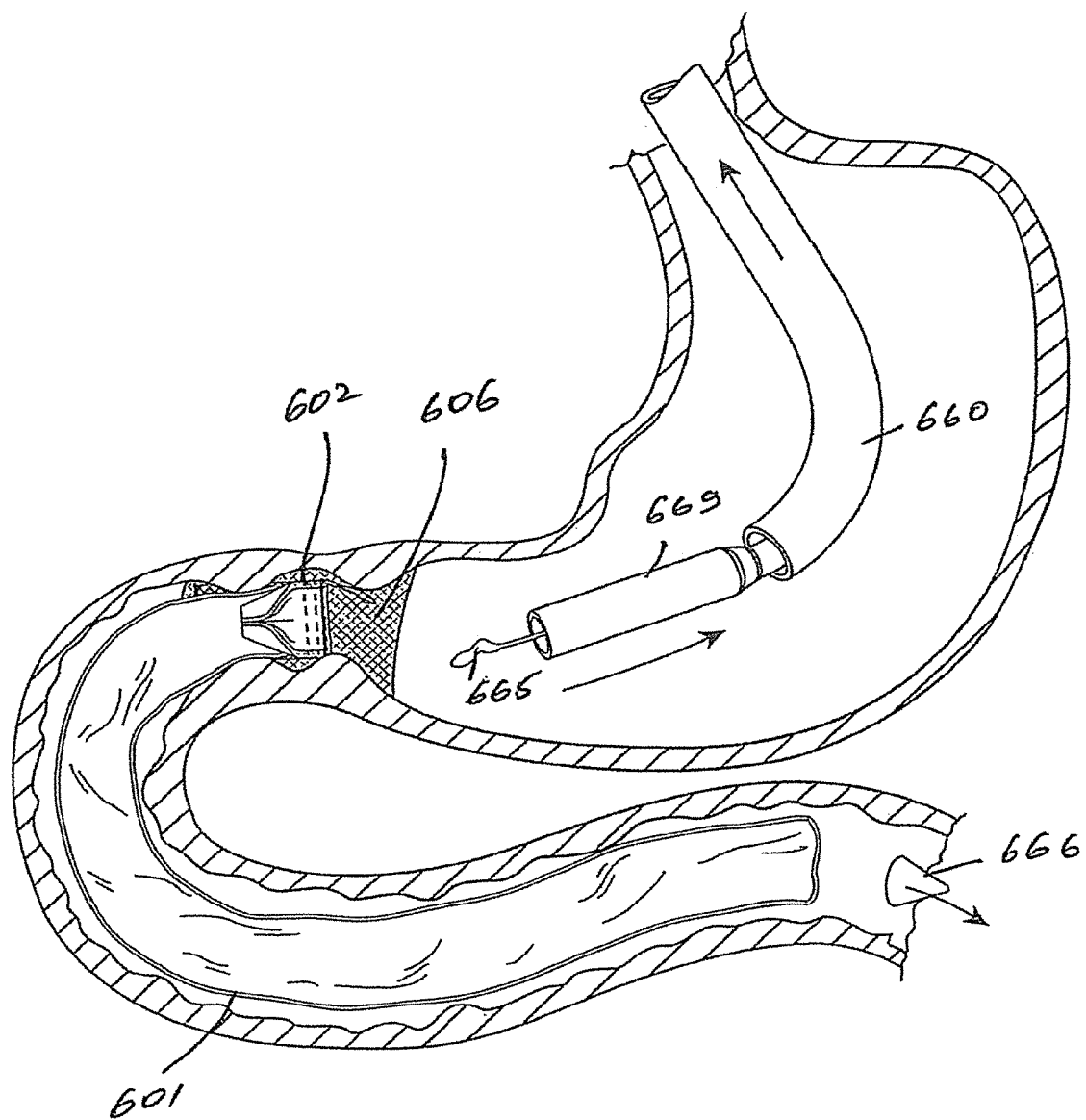
FIG. 89 is a cross sectional view of the implant device in situ with the sleeve extended and the delivery system being removed.

In Fig. 88, Sheet 35 of 70, delete "Fig 88" and insert -- Fig. 88 --, therefor.

Figure 133:
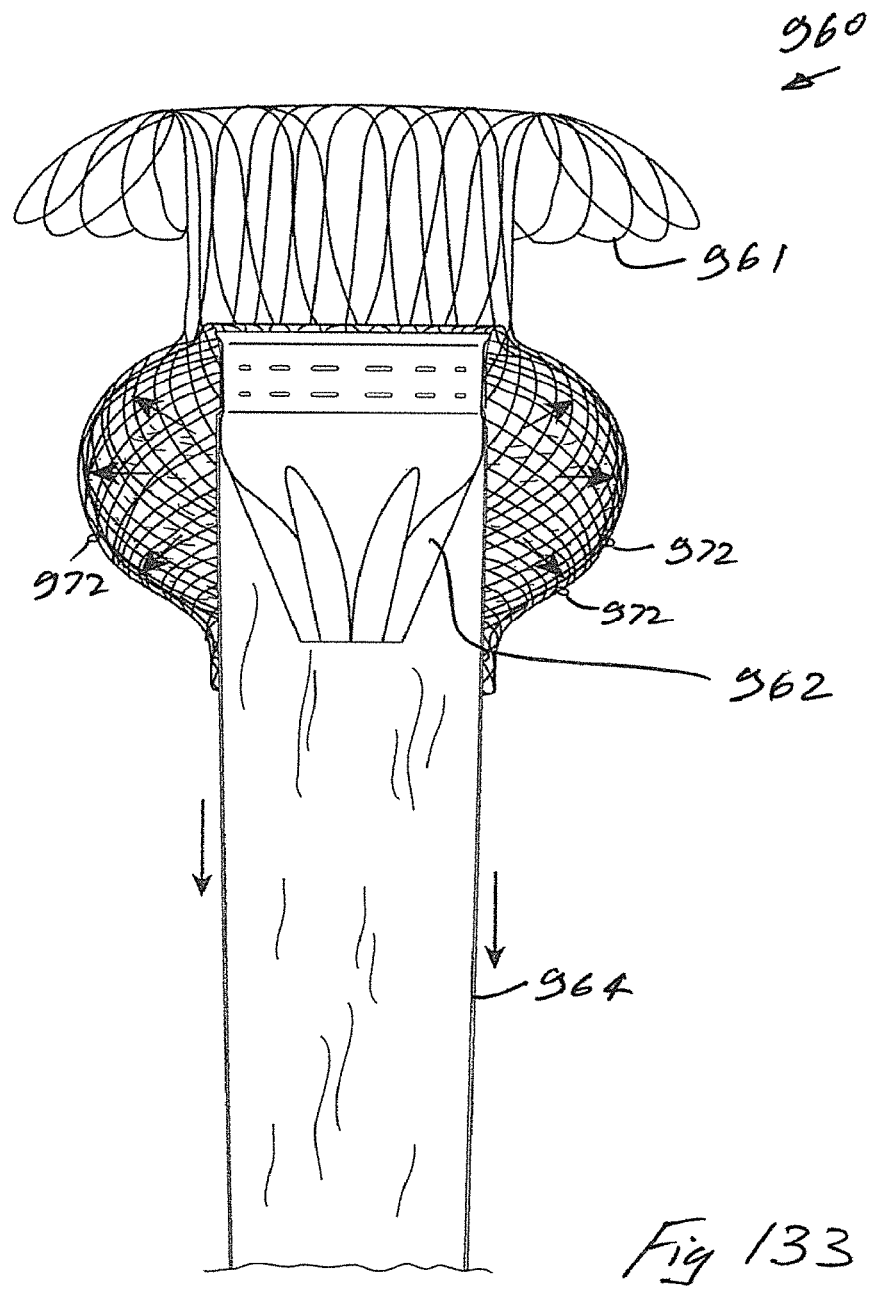
FIG. 133 is a side, partially cross sectional view of an obesity treatment device according to the invention.
Figure 134:
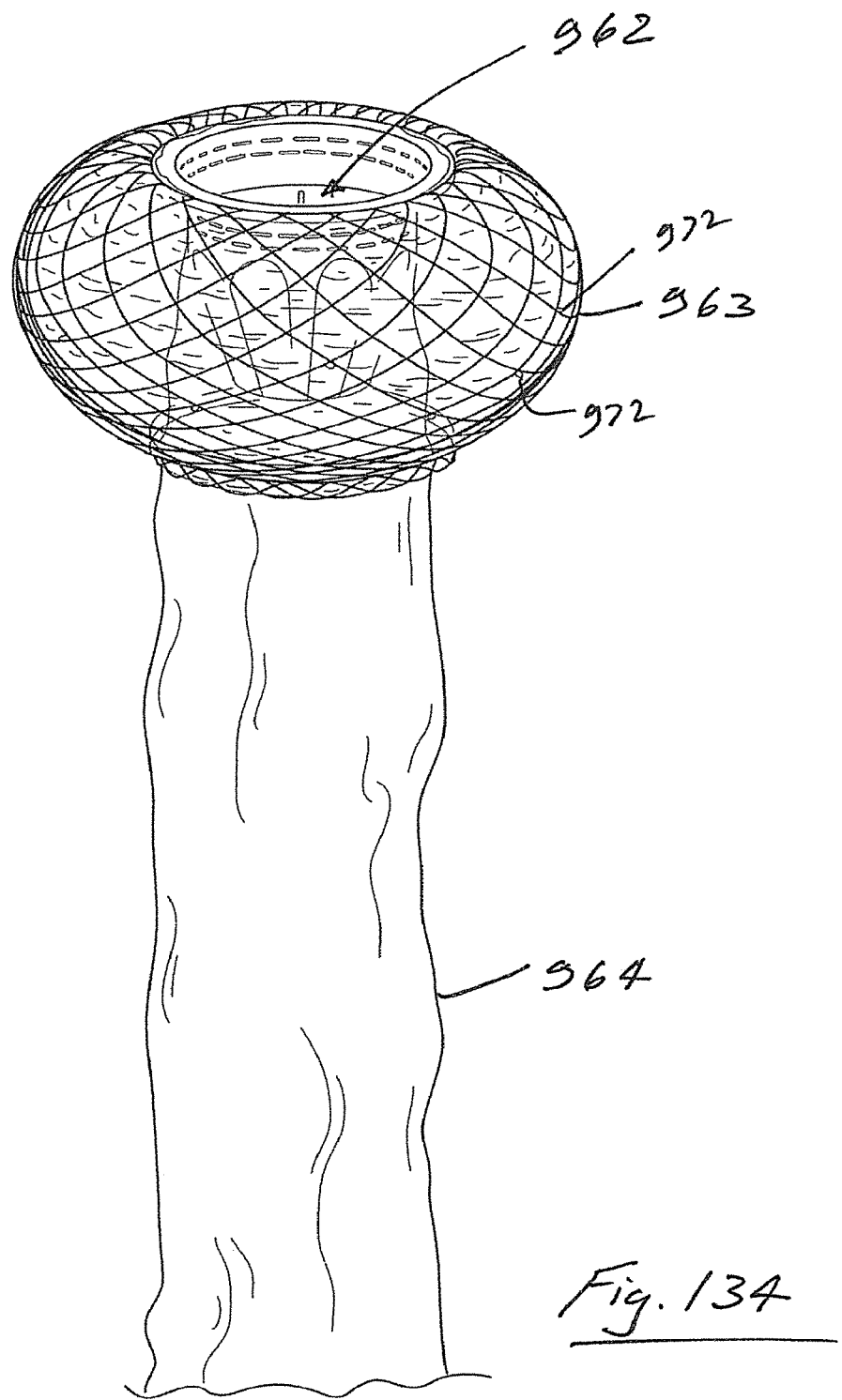
FIG. 134 is an isometric view of a valve, internal support and sleeve of the device of FIG. 33.
Figure 135:
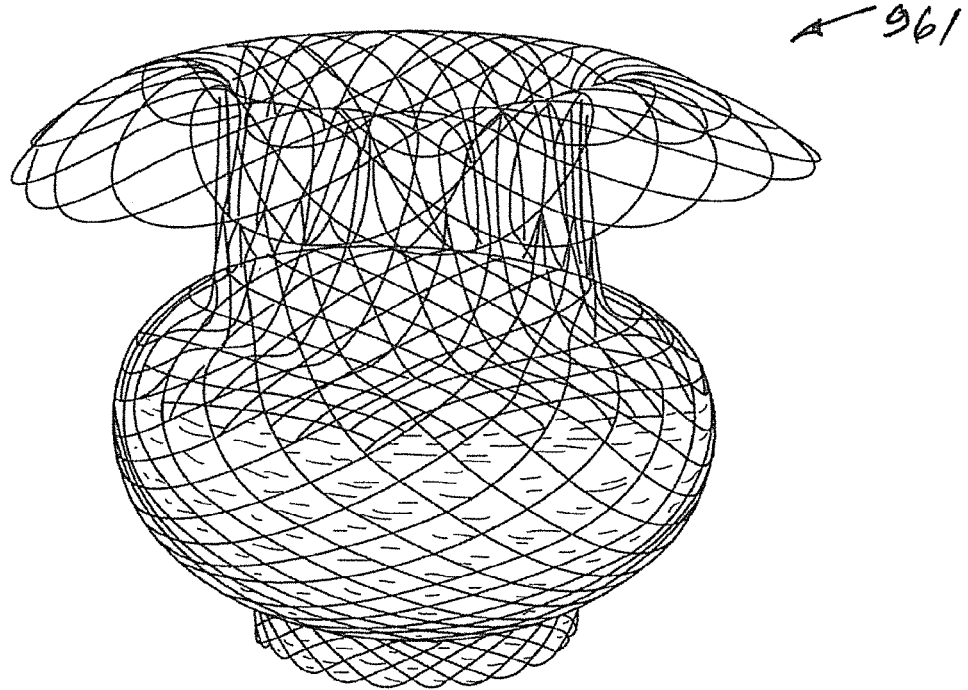
FIG. 135 is an isometric view of an external support of the device of FIG. 133.
Figure 136:
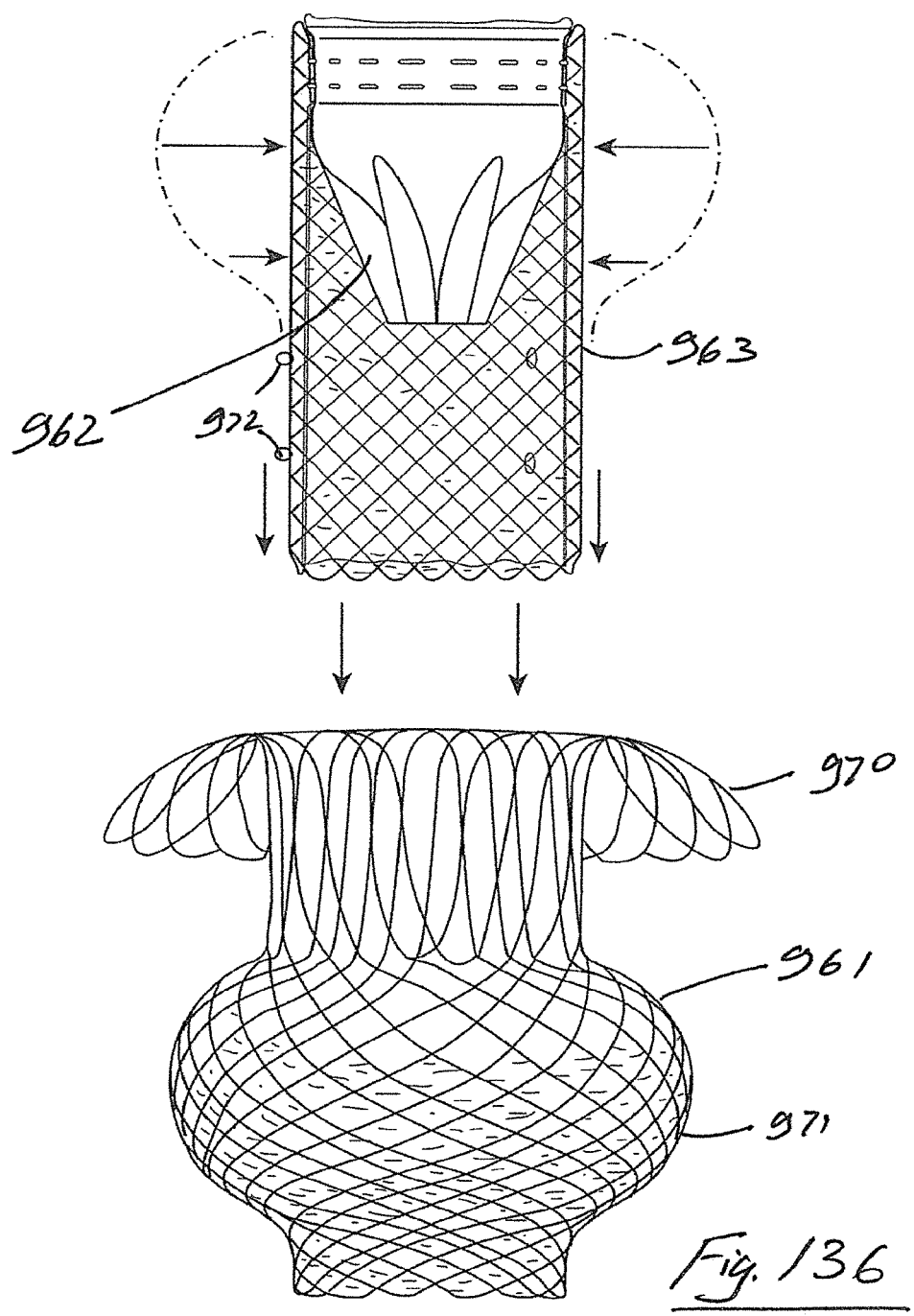
FIG. 136 is an exploded view illustrating the mounting of the valve, internal support and sleeve of FIG. 134 to the external support of FIG. 135.
Figure 137:
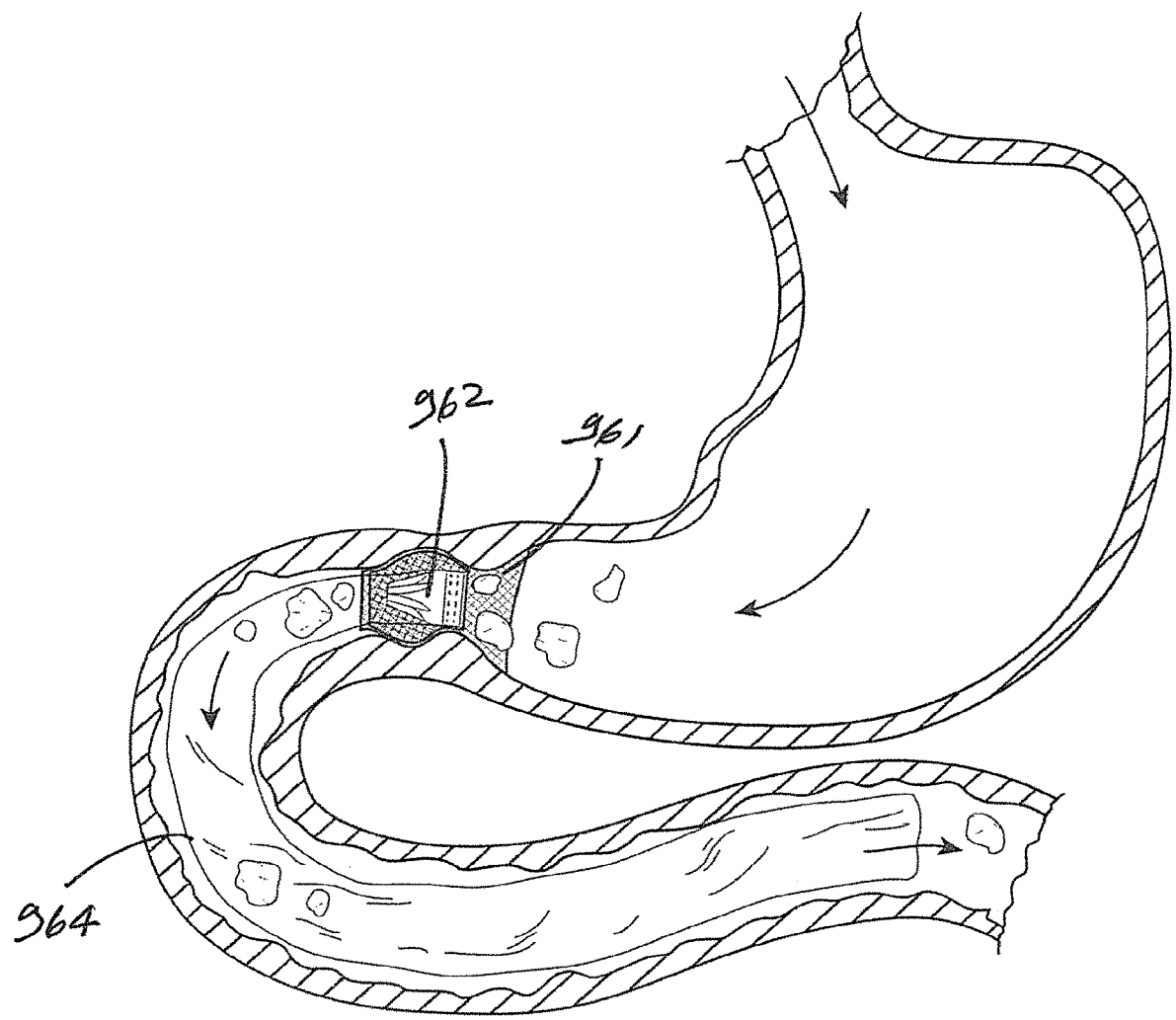
FIG. 137 is a cross sectional view of the obesity treatment device of the invention, in use.
Figure 138:
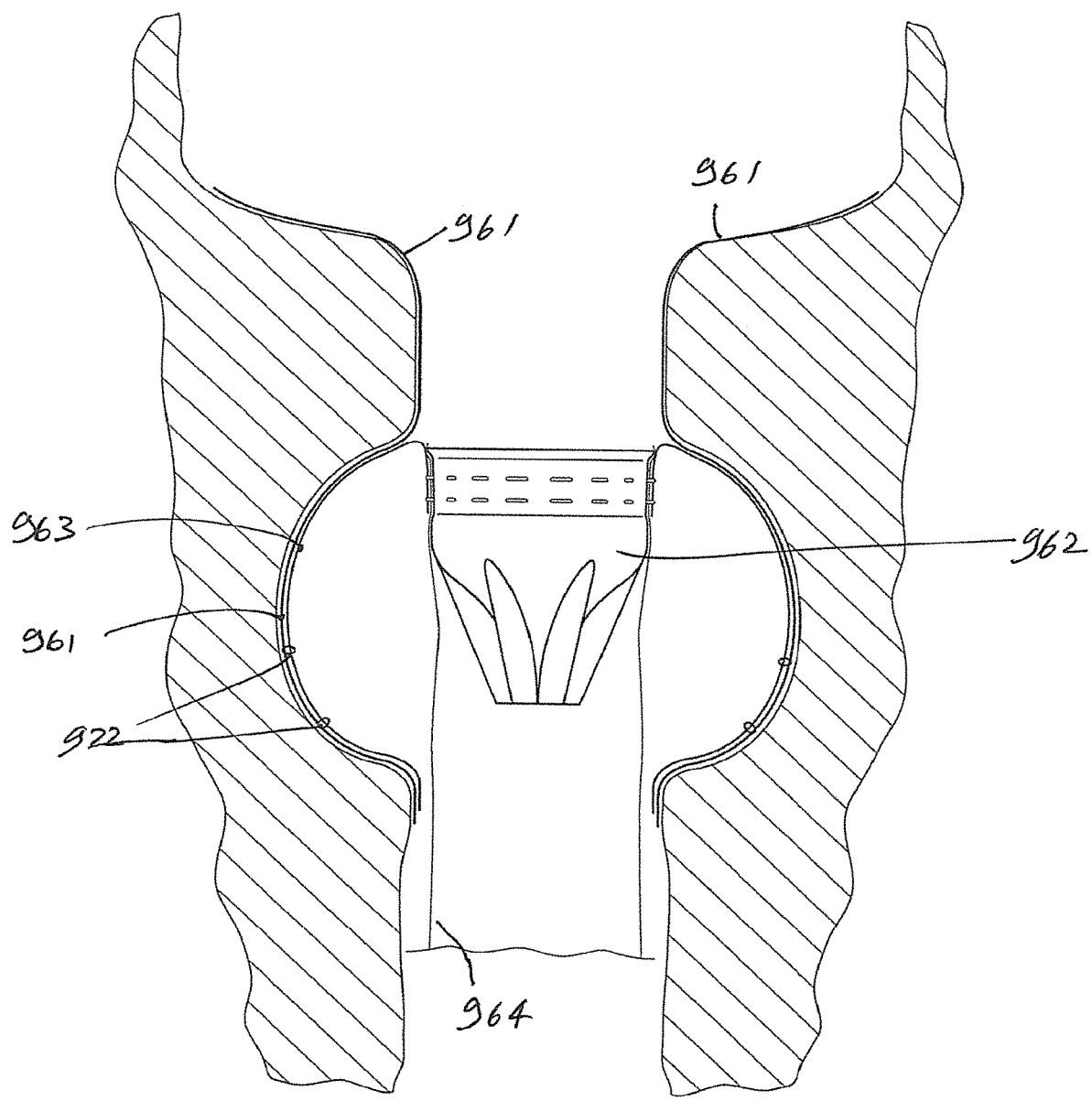
FIG. 138 is am enlarged cross sectional view of the obesity treatment device in situ, in one configuration.
Figure 139:
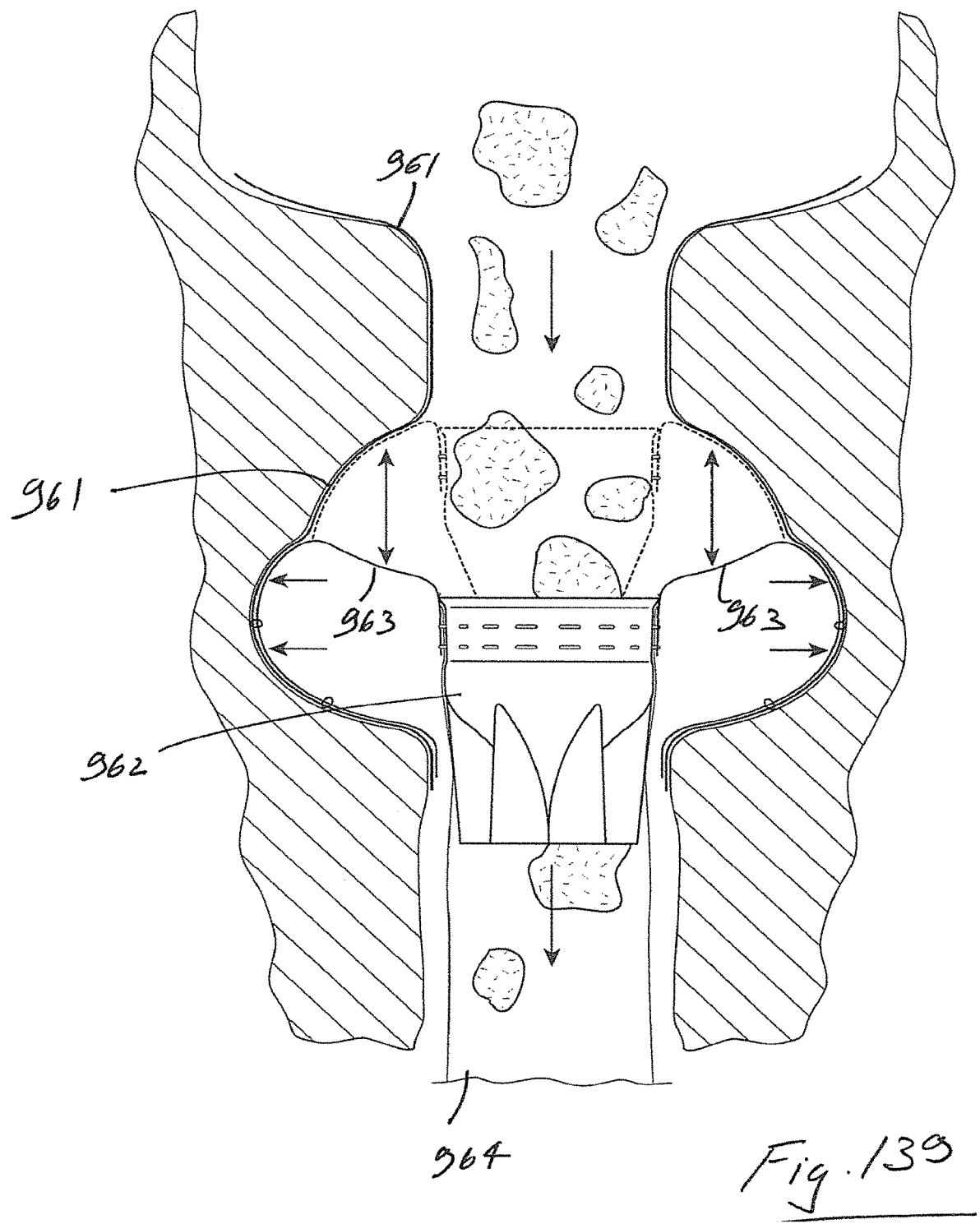
FIG. 139 is a view similar to FIG. 140 with the device in another configuration of use.

In Fig. 133, Sheet 64 of 70, delete "Fig 133" and insert -- Fig. 133 --, therefor.

In the Specification

In Column 1, Line 25, delete "trout" and insert -- from --, therefor.

In Column 2, Line 38, delete "region" and insert -- region. --, therefor.

In Column 3, Line 14, delete "case The" and insert -- case the --, therefor.

In Column 6, Line 49, delete "hereof." and insert -- thereof. --, therefor.

In Column 7, Line 4, delete "in the one direction." and insert -- in one direction. --, therefor.

In Column 10, Line 46, delete "prosthesis." and insert -- prosthesis; --, therefor.

In Column 12, Line 21, delete "invention" and insert -- invention; --, therefor.

In Column 12, Line 57, delete "FIG. 123;" and insert the same at Line 56, after "prosthesis of" as a continuation paragraph.

In Column 15, Line 29, delete "expensile" and insert -- expansile --, therefor.

In Column 17, Line 25, delete "device 300" and insert -- device 200 --, therefor.

In Column 20, Line 61, delete "stent 605" and insert -- stent 606 --, therefor.

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*

In Column 21, Line 62, delete "tip 666" and insert -- tip 665 --, therefor.

In Column 23, Line 18, delete "prostheseis" and insert -- prosthesis --, therefor.

In Column 23, Line 20, delete "antrun" and insert -- antrum --, therefor.